United States Patent
Bigi et al.

(10) Patent No.: US 9,994,547 B2
(45) Date of Patent: Jun. 12, 2018

(54) HETEROARYLAMIDE INHIBITORS OF TBK1

(71) Applicant: Takeda Pharmaceutical Company Limited, Osaka (JP)

(72) Inventors: Simone Bigi, San Diego, CA (US); Walter Keung, San Diego, CA (US); Steve Swann, San Diego, CA (US); Phong H. Vu, San Diego, CA (US); Steven John Woodhead, San Diego, CA (US); Anthony R. Gangloff, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days. days.

(21) Appl. No.: 15/517,473

(22) PCT Filed: Oct. 2, 2015

(86) PCT No.: PCT/US2015/053801
§ 371 (c)(1),
(2) Date: Apr. 6, 2017

(87) PCT Pub. No.: WO2016/057338
PCT Pub. Date: Apr. 14, 2016

(65) Prior Publication Data
US 2017/0313675 A1   Nov. 2, 2017

Related U.S. Application Data

(60) Provisional application No. 62/060,134, filed on Oct. 6, 2014.

(51) Int. Cl.
| | | |
|---|---|---|
| *A61K 31/497* | (2006.01) |
| *C07D 401/14* | (2006.01) |
| *C07D 403/12* | (2006.01) |
| *C07D 413/14* | (2006.01) |
| *C07D 491/10* | (2006.01) |
| *C07D 401/04* | (2006.01) |
| *C07D 241/20* | (2006.01) |
| *C07D 401/00* | (2006.01) |

(52) U.S. Cl.
CPC .......... *C07D 401/04* (2013.01); *A61K 31/497* (2013.01); *C07D 241/20* (2013.01); *C07D 401/14* (2013.01); *C07D 403/12* (2013.01); *C07D 413/14* (2013.01); *C07D 491/10* (2013.01); *C07D 401/00* (2013.01)

(58) Field of Classification Search
CPC .. A61K 31/497; C07D 241/20; C07D 401/14; C07D 403/12; C07D 413/14; C07D 491/10
See application file for complete search history.

(56) References Cited

U.S. PATENT DOCUMENTS

2014/0228340 A1   8/2014   Hoelzemann et al.

FOREIGN PATENT DOCUMENTS

| WO | WO 2004/043926 A1 | 5/2004 |
| WO | WO 2006/081391 A2 | 8/2006 |
| WO | WO 2012/161877 A1 | 11/2012 |
| WO | WO 2013/034238 A1 | 3/2013 |
| WO | WO 2014/128486 A1 | 8/2014 |

*Primary Examiner* — Rebecca L Anderson
(74) *Attorney, Agent, or Firm* — Matthew J. Russo; David M. Stemerick

(57) ABSTRACT

Disclosed are compounds of formula 1:

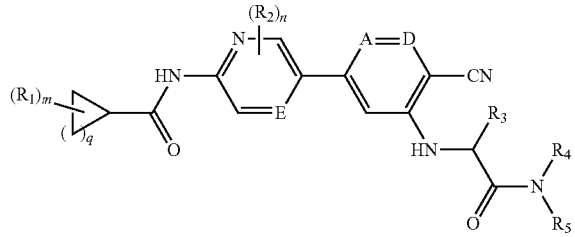

which are useful as inhibitors of TBK1. Also disclosed are pharmaceutical compositions which contain the compounds, methods for treatment of conditions associated with TBK1, and processes for making the compounds and intermediates thereof.

18 Claims, No Drawings

HETEROARYLAMIDE INHIBITORS OF TBK1

CROSS-REFERENCE TO RELATED APPLICATIONS

This application is the U.S. National Stage entry under 35 U.S.C. § 371(c) of International Application PCT/US2015/053801, filed Oct. 2, 2015, which claims the benefit of U.S. Provisional Application No. 62/060,134, filed Oct. 6, 2014.

FIELD OF THE INVENTION

The present invention relates to medicinal chemistry, pharmacology, and medicine.

BACKGROUND OF THE INVENTION

TANK-binding kinase 1 (TBK1), also known NAK and T2K, has a role in innate immunity. TBK1 serves as an integrator of multiple signals induced by receptor-mediated pathogen detection and as a modulator of the levels of type I interferons. TBK1 is also activated by various growth factors.

Due to its central role in immunologic and inflammatory responses inhibitors of TBK1 are expected to provide benefit to patients suffering from septic shock, autoimmune diseases, chronic inflammation, and rejection of transplanted tissues. There is a need for treatment of such conditions and others described herein with compounds that are TBK1 inhibitors. The present invention provides inhibitors of TBK1.

Certain inhibitors of CRAC ion channels are described in WO 2006/081391 and certain IP receptor antagonists are disclosed in WO 2004/043926.

SUMMARY OF THE INVENTION

The present invention provides compounds of formula 1:

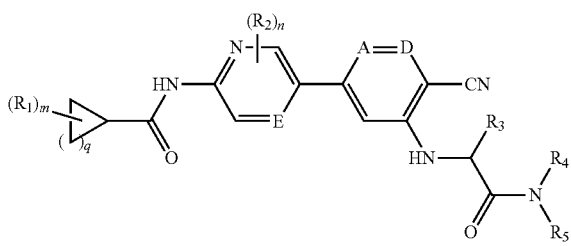

m is selected from 0, 1, and 2;
n is selected from 0, 1, and 2;
q is selected from 1, 2, and 3;
$R_1$, each time taken, is independently selected from the group consisting of fluoro, hydroxymethyl, and $C_{1-4}$ alkyl;
$R_2$, each time taken, is independently selected from the group consisting of cyano, halo, hydroxy, amino, $C_{1-4}$ alkyl, $C_{1-4}$ alkoxy, hydroxymethyl, and trifluoromethyl;
$R_3$ is selected from the group consisting of hydrogen and optionally substituted $C_{1-4}$ alkyl;
$R_4$ is selected from the group consisting of hydrogen and optionally substituted $C_{1-4}$ alkyl;
$R_5$ is selected from the group consisting of hydrogen, optionally substituted $C_{1-6}$ alkyl, optionally substituted $C_{3-8}$ cycloalkyl, optionally substituted $C_{1-10}$ heteroaryl, and optionally substituted $C_{3-6}$ heterocyclyl;
or
$R_4$ and $R_5$ together with the nitrogen to which they are attached form a 4 to 8 membered, saturated, monocyclic or bicyclic ring optionally having an additional ring heteroatom selected from the group N, O, and $S(O)_p$ wherein p is selective from 0, 1, and 2 and optionally substituted on ring carbons with 1 to 5 substituents independently selected from the group consisting of cyano, halo, hydroxy, amino, $C_{1-9}$ amide, $C_{1-4}$ alkyl, $C_{1-4}$ alkoxy, hydroxymethyl, fluoromethyl, difluoromethyl, and trifluoromethyl and any additional ring nitrogen is optionally substituted with a substituent selected from the group consisting of hydrogen, —C(O)—$C_{1-4}$ alkyl and optionally substituted $C_{1-4}$ alkyl;
E is selected from the group consisting of N and $CR_2$;
A is selected from the group consisting of N and $CR_6$;
D is selected from the group consisting of N and $CR_7$;
$R_6$ is selected from the group consisting of hydrogen, cyano, halo, $C_{1-4}$ alkyl, $C_{1-4}$ alkoxy, and trifluoromethyl;
$R_7$ is selected from the group consisting of hydrogen, cyano, halo, $C_{1-4}$ alkyl, $C_{1-4}$ alkoxy, and trifluoromethyl;
or a pharmaceutically acceptable salt thereof.

The present invention also provides pharmaceutical compositions, comprising: a compound of formula 1 or a pharmaceutically acceptable salt thereof and a pharmaceutically acceptable excipient.

The compounds of the invention are inhibitors of TBK1 they are useful for the treatment of conditions associated with TBK1, including immunological disorders, such as autoimmune disorders, inflammatory disorders, fibrotic conditions, cancer, sepsis, and other disorders mentioned herein. Thus, the present invention provides for the use of the compounds of the invention as a medicament, including for the manufacture of a medicament. The present invention also provides methods of treating the conditions associated with TBK1, comprising: administering to a patient in need thereof an effective amount of the compounds of the invention.

The present invention also provides processes from making TBK1 inhibitors and intermediates thereof.

DETAILED DESCRIPTION OF THE INVENTION

The term "$C_{1-4}$ alkyl" refers to a straight or branched alkyl chain of one to four carbon atoms.

The term "optionally substituted $C_{1-4}$ alkyl" refers to a $C_{1-4}$ alkyl optionally substituted with 1 to 6 substituents independently selected from the group consisting of optionally substituted $C_{1-4}$ alkoxy, $C_{1-4}$ thioalkoxy, $C_{1-9}$ amide, $C_{1-7}$ amido, amino, $C_{1-8}$ alkylamino, $C_{1-5}$ oxycarbonyl, $C_{1-5}$ carbonyloxy, $C_{1-8}$ sulfonyl, cyano, optionally substituted $C_{3-8}$ cycloalkyl, $C_{3-8}$ cycloalkoxy, halo, hydroxy, nitro, oxo, optionally substituted $C_{3-6}$ heterocyclyl, optionally substituted $C_{1-10}$ heteroaryl, and optionally substituted $C_{5-10}$ aryl.

More particularly "optionally substituted $C_{1-4}$ alkyl" refers to a $C_{1-4}$ alkyl optionally substituted with 1 to 6 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

The term "$C_{1-6}$ alkyl" refers to a straight or branched alkyl chain of one to six carbon atoms.

The term "optionally substituted $C_{1-6}$ alkyl" refers to a $C_{1-6}$ alkyl optionally substituted with 1 to 7 substituents independently selected from the group consisting of amino, $C_{1-8}$ alkylamino, optionally substituted $C_{1-4}$ alkoxy, $C_{1-4}$ thioalkoxy, $C_{1-9}$ amide, $C_{1-7}$ amido, $C_{1-5}$ oxycarbonyl, $C_{1-5}$ carbonyloxy, $C_{1-8}$ sulfonyl, cyano, optionally substituted $C_{3-8}$ cycloalkyl, halo, hydroxy, oxo, optionally substituted $C_{1-10}$ heteroaryl, optionally substituted $C_{3-6}$ heterocyclyl, and optionally substituted $C_{5-10}$ aryl.

More particularly "optionally substituted $C_{1-6}$ alkyl" refers to a $C_{1-6}$ alkyl optionally substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally substituted with 1 to 6 substituents independently selected from the group consisting of $C_{1-4}$ alkoxy, $C_{1-9}$ amide, $C_{1-5}$ oxycarbonyl, cyano, optionally substituted $C_{3-8}$ cycloalkyl, halo, hydroxy, optionally substituted $C_{1-10}$ heteroaryl, and optionally substituted $C_{5-10}$ aryl. While it is understood that where the optional substituent is $C_{1-4}$ alkoxy or hydroxy then the substituent is generally not alpha to the alkoxy attachment point, the term "optionally substituted $C_{1-4}$ alkoxy" includes stable moieties and specifically includes trifluoromethoxy, difluoromethoxy, and fluoromethoxy.

More particularly "optionally substituted $C_{1-4}$ alkoxy" refers to a $C_{1-4}$ alkoxy optionally substituted with 1 to 6 substituents independently selected from the group consisting of $C_{1-4}$ alkoxy, cyano, $C_{3-8}$ cycloalkyl, halo, hydroxy, and optionally substituted phenyl. Even more particularly "optionally substituted $C_{1-4}$ alkoxy" refers to trifluoromethoxy, difluoromethoxy, and fluoromethoxy.

The term "$C_{1-9}$ amide" refers to a —C(O)NR$_a$R$_b$ group in which R$_a$ is selected from the group consisting of hydrogen and $C_{1-4}$ alkyl, and R$_b$ is selected from the group consisting of hydrogen, $C_{1-3}$ alkyl, and optionally substituted phenyl.

The term "$C_{1-7}$ amido" refers to a —NHC(O)R$_c$ group in which R$_c$ is selected from the group consisting of hydrogen, $C_{1-6}$ alkyl, and optionally substituted phenyl.

The term "$C_{1-5}$ carbamoyl" refers to an O- or N-linked carbamate substituted with a terminal $C_{1-4}$ alkyl.

The term "$C_{1-5}$ ureido" refers to a urea optionally substituted with a $C_{1-4}$ alkyl.

The term "$C_{1-8}$ alkylamino" refers to a —NR$_d$R$_e$ group in which R$_d$ is a $C_{1-4}$ alkyl and R$_e$ is selected from the group consisting of hydrogen and $C_{1-4}$ alkyl.

The term "$C_{5-10}$ aryl" refers to a monocyclic and polycyclic unsaturated, conjugated hydrocarbon having five to ten carbon atoms, and includes cyclopentyldienyl, phenyl, and naphthyl.

More particularly "$C_{5-10}$ aryl" refers to phenyl.

The term "optionally substituted $C_{5-10}$ aryl" refers to a $C_{5-10}$ aryl optionally substituted with 1 to 5 substituents independently selected from the group consisting of optionally substituted $C_{1-4}$ alkyl, optionally substituted $C_{1-4}$ alkoxy, $C_{1-4}$ thioalkoxy, amino, $C_{1-8}$ alkylamino, $C_{1-9}$ amide, $C_{1-7}$ amido, $C_{1-5}$ oxycarbonyl, $C_{1-5}$ carbonyloxy, $C_{1-8}$ sulfonyl, $C_{1-5}$ carbamoyl, $C_{1-6}$ sulfonylamido, aminosulfonyl, $C_{1-10}$ aminosulfonyl, $C_{1-5}$ ureido, cyano, halo, and hydroxyl.

More particularly "optionally substituted $C_{5-10}$ aryl" refers to a $C_{5-10}$ aryl optionally substituted with 1 to 5 substituents independently selected from the group consisting of $C_{1-4}$ alkyl, $C_{1-4}$ alkoxy, cyano, halo, hydroxy, amino, trifluoromethyl, and trifluoromethoxy.

Even more particularly "optionally substituted $C_{5-10}$ aryl" refers to phenyl optionally substituted with 1 to 5 substituents independently selected from the group consisting of $C_{1-4}$ alkyl, $C_{1-4}$ alkoxy, cyano, halo, trifluoromethyl, and trifluoromethoxy.

The term "$C_{1-5}$ oxycarbonyl" refers to an oxycarbonyl group (—CO$_2$H) and $C_{1-4}$ alkyl ester thereof.

The term "$C_{1-5}$ carbonyloxy" refers to a carbonyloxy group (—O$_2$CR$_f$), in which R$_f$ is selected from the group consisting of hydrogen and $C_{1-4}$ alkyl, for example, acetoxy.

The term "$C_{3-8}$ cycloalkyl" refers to an alkyl ring of three to eight carbon atoms, and includes cyclopropyl, cyclobutyl, cyclopentyl, cyclohexyl, and the like.

The term "optionally substituted $C_{3-8}$ cycloalkyl" refers to a $C_{3-8}$ cycloalkyl optionally substituted with 1 to 6 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl.

More particularly "optionally substituted $C_{3-8}$ cycloalkyl" refers to a $C_{3-8}$ cycloalkyl optionally substituted with 1 to 3 substituents independently selected from the group consisting of $C_{1-4}$ alkyl, $C_{1-4}$ alkoxy, halo, and hydroxy.

The term "$C_{3-8}$ cycloalkoxy" refers to a $C_{3-8}$ cycloalkyl attached through and oxygen.

The terms "halogen" and "halo" refers to a chloro, fluoro, bromo or iodo.

The term "$C_{3-6}$ heterocyclyl" refers to a 4 to 8 membered monocyclic saturated or partially (but not fully) unsaturated ring having one or two heteroatoms selected from the group consisting of nitrogen, oxygen, and sulfur and the ring optionally includes a carbonyl to form a lactam or lactone. It is understood that where sulfur is included that the sulfur may be either —S—, —SO—, and —SO$_2$—. For example, but not limiting, the term includes azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl, and the like. It is understood that a $C_{3-6}$ heterocyclyl can be attached as a substituent through a ring carbon or a ring nitrogen atom.

More particularly "$C_{3-6}$ heterocyclyl" is selected from the group consisting of pyrrolidinyl, piperidinyl, piperazinyl, morpholinyl, oxetanyl, tetrahydropyranyl, tetrahydrothiopyranyl, and tetrahydrofuryl.

The term "optionally substituted $C_{3-6}$ heterocyclyl" refers to a $C_{3-6}$ heterocyclyl optionally substituted on the ring carbons with 1 to 4 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, and optionally substituted phenyl; and optionally substituted on any ring nitrogen with a substituent independently selected from the group consisting of hydrogen, optionally substituted $C_{1-4}$ alkyl, $C_{3-8}$ cycloalkyl, optionally substituted $C_{3-6}$ heterocyclyl, optionally substituted $C_{1-10}$ heteroaryl, and optionally substituted phenyl.

More particularly "optionally substituted $C_{3-6}$ heterocyclyl" refers to a $C_{3-6}$ heterocyclyl optionally substituted on the ring carbons with 1 to 4 substituents independently selected from the group consisting of $C_{1-4}$ alkyl, $C_{1-4}$ alkoxy, halo, and hydroxy and optionally substituted on any ring nitrogen with a $C_{1-4}$ alkyl.

The term "$C_{1-10}$ heteroaryl" refers to a five to thirteen membered, monocyclic or polycyclic fully unsaturated, ring or ring system with one to ten carbon atoms and one or more, typically one to four, heteroatoms selected from the group consisting of nitrogen, oxygen, and sulfur. For example, but not limiting, the term includes furyl, thienyl, pyrrolyl, imidazolyl, isothiazolyl, isoxazolyl, oxadiazolyl, oxazolyl, thiazolyl, thiadiazolyl, triazolyl, tetrazolyl, pyrazinyl, pyrazolyl, pyridazinyl, pyridyl, pyrimidyl, azepinyl, diazepinyl, benzazepinyl, benzodiazepinyl, benzofuryl, benzothienyl, indolyl, isoindolyl, benzimidazolyl, benzisothiazolyl, benzisoxazolyl, benzoxadiazolyl, benzoxazolyl, benzopyrazinyl, benzopyrazolyl, imidazopyridyl, pyrazolopyridyl, pyrrolopyridyl, quinazolyl, thienopyridyl, imidazopyridyl, quinolyl, isoquinolyl benzothiazolyl, and the like. It is understood that a $C_{1-10}$ heteroaryl can be attached as a substituent through a ring carbon or a ring nitrogen atom where such an attachment mode is available, for example for a pyrrolyl, indolyl, imidazolyl, pyrazolyl, azepinyl, triazolyl, pyrazinyl, etc.

More particularly "$C_{1-10}$ heteroaryl" is selected from the group consisting of furyl, thienyl, pyrrolyl, imidazolyl, oxazolyl, thiazolyl, pyrazolyl, triazolyl, pyridyl, and pyrimidyl.

The term "optionally substituted $C_{1-10}$ heteroaryl" refers to a $C_{1-10}$ heteroaryl optionally substituted with 1 to 5 substituents on carbon independently selected from the group consisting of amino, $C_{1-8}$ alkylamino, $C_{1-9}$ amide, $C_{1-7}$ amido, $C_{1-5}$ carbamoyl, $C_{1-6}$ sulfonylamido, aminosulfonyl, $C_{1-10}$ aminosulfonyl, $C_{1-5}$ ureido, optionally substituted $C_{1-4}$ alkyl, optionally substituted $C_{1-4}$ alkoxy, cyano, halo, hydroxyl, oxo, nitro, $C_{1-5}$ carbonyloxy, $C_{1-5}$ oxycarbonyl, and $C_{1-8}$ sulfonyl and optionally substituted with a substituent on each nitrogen independently selected from the group consisting of optionally substituted $C_{1-4}$ alkyl, $C_{1-8}$ sulfonyl, optionally substituted $C_{3-6}$ heterocyclyl, and optionally substituted phenyl.

More particularly "optionally substituted $C_{1-10}$ heteroaryl" refers to a $C_{1-10}$ heteroaryl optionally substituted with 1 to 3 substituents on carbon independently selected from the group consisting of amino, $C_{1-8}$ alkylamino, $C_{1-9}$ amide, $C_{1-4}$ alkyl, $C_{1-4}$ alkoxy, cyano, halo, hydroxyl, oxo, trifluoromethyl, and trifluoromethoxy and optionally substituted on a ring nitrogen with a $C_{1-4}$ alkyl.

Even more particularly "optionally substituted $C_{1-10}$ heteroaryl" refers to a $C_{1-10}$ heteroaryl selected from the group consisting of furyl, thienyl, pyrrolyl, imidazolyl, oxazolyl, thiazolyl, pyrazolyl, diazolyl, pyridyl, pyrimidyl, and triazolyl each optionally substituted with 1 to 3 substituents independently selected from the group consisting of $C_{1-4}$ alkyl, $C_{1-4}$ alkoxy, cyano, halo, trifluoromethyl, and trifluoromethoxy and optionally substituted on a ring nitrogen with a methyl.

The term "oxo" refers to an oxygen atom doubly bonded to the carbon to which it is attached to form the carbonyl of a ketone or aldehyde. For example, a pryidone radical is contemplated as an oxo substituted $C_{1-10}$ heteroaryl.

The term "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amide, amino, $C_{1-8}$ alkylamino, $C_{1-5}$ oxycarbonyl, cyano, halo, hydroxyl, nitro, $C_{1-8}$ sulfonyl, and trifluoromethyl.

More particularly "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxyl, nitro, and trifluoromethyl.

The term "$C_{1-6}$ sulfonylamido" refers to a —NHS(O)$_2$—R$_g$ group wherein R$_g$ is selected from the group consisting of $C_{1-6}$ alkyl and optionally substituted phenyl.

The term "aminosulfonyl" refers to a —S(O)$_2$NH$_2$.

The term "$C_{1-10}$ aminosulfonyl" refers to a —S(O)$_2$NR$_h$R$_i$ group wherein R$_h$ is selected from the group consisting of hydrogen and $C_{1-4}$ alkyl and R$_i$ is selected from the group consisting of $C_{1-4}$ alkyl, and optionally substituted phenyl.

The term "$C_{1-8}$ sulfonyl" refers to a sulfonyl linked to a $C_{1-6}$ alkyl group, $C_{3-8}$ cycloalkyl, or an optionally substituted phenyl.

The term "$C_{1-4}$ thioalkoxy" refers to a $C_{1-4}$ alkyl attached through a sulfur atom.

The term "pharmaceutically acceptable salt" refers to salts of pharmaceutically acceptable organic acids and bases or inorganic acids and bases. Such salts are well known in the art and include those described in Journal of Pharmaceutical Science, 66, 2-19 (1977). An example is the hydrochloride salt.

The term "substituted," including when used in "optionally substituted" refers to one or more hydrogen radicals of a group are replaced with non-hydrogen radicals (substituent(s)). It is understood that the substituents may be either the same or different at every substituted position. Combinations of groups and substituents envisioned by this invention are those that are stable or chemically feasible.

The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

The term "substantially enantiomerically pure" refers to greater than 90%, preferably greater than 97%, and more preferably greater than 99% enantiomeric purity at the stereocenter. Thus, the "substantially enantiomerically pure" refers to greater than 80%, preferably greater than 94%, and more preferably greater than 98% ee.

It is understood that, where the terms defined herein mention a number of carbon atoms, that the mentioned number refers to the mentioned group and does not include any carbons that may be present in any optional substituent(s) thereon.

The skilled artisan will appreciate that certain of the compounds of the invention may exist as isomers. All stereoisomers of the compounds of the invention, including geometric isomers, enantiomers, and diastereomers, in any ratio, are contemplated to be within the scope of the present invention.

The skilled artisan will appreciate that certain of the compounds of the invention exist as tautomers. All tautomeric forms the compounds of the invention are contemplated to be within the scope of the present invention.

Compounds of the invention also include all isotopic variations, in which at least one atom is replaced by an atom having the same atomic number, but an atomic mass different from the atomic mass most commonly found in nature.

The terms "compounds of the invention" and "a compound of the invention" and the like include the embodiment of formula 1, the other more particular embodiments encompassed by formula 1 described herein, each of the exemplified compounds described herein, and a pharmaceutically acceptable salt of each of these embodiments.

It is understood that when R$_4$ and R$_5$ together with the nitrogen to which they are attached form a 4 to 8 membered, saturated, monocyclic or bicyclic ring it is understood that monocyclic rings include in particular azetidinyl, pyrrolidinyl, piperidinyl, piperazinyl, morpholinyl, thiomorpholinyl, hexahydropyrimidinyl, tetrahydropyrimidinyl, and dihydroimidazolyl; more particularly, pyrrolidinyl, piperidinyl, piperazinyl, morpholinyl; and even more particularly pyrrolidinyl and piperidinyl. To be completely clear, each of the specifically mentioned rings above are optionally substituted on any ring carbon as described above. It is further understood that when R$_4$ and R$_5$ together with the nitrogen to which they are attached form a bicyclic ring the bicyclic ring can be fused, bridged, or spirofused.

Further embodiments of compounds of the invention are provided below:

(a) One embodiment relates to compounds of formula 1 wherein m is 0.

(b) One embodiment relates to compounds of formula 1 wherein m is 1 and $R_1$ is methyl.

(c) One embodiment relates to compounds of formula 1 and embodiments (a) and (b) wherein n is 0.

(d) One embodiment relates to compounds of formula 1 and embodiments (a), (b), and (c) wherein $R_3$ is hydrogen.

(e) One embodiment relates to compounds of formula 1 and embodiments (a), (b), and (c) wherein $R_3$ is optionally substituted $C_{1-4}$ alkyl. In another embodiment of (e) $R_3$ is selected from the group consisting or 2-(thiomethyl)ethyl, hydroxymethyl, and 1-hydroxyethyl.

(f) One embodiment relates to compounds of formula 1 and embodiments (a), (b), (c), (d), and (e) wherein $R_4$ is $C_{1-4}$ alkyl. In another embodiment of (f) $R_3$ is selected from the group consisting of methyl, ethyl, isopropyl, and s-butyl.

(g) One embodiment relates to compounds of formula 1 and embodiments (a), (b), (c), (d), (e), and (f) wherein $R_5$ is $C_{1-6}$ alkyl.

(h) One embodiment relates to compounds of formula 1 and embodiments (a), (b), (c), (d), (e), (f), and (g) wherein q is 1.

(i) One embodiment relates to compounds of formula 1 and embodiments (a), (b), (c), (d), (e), (f), and (g) wherein q is 2.

(j) One embodiment relates to compounds of formula 1 and embodiments (a), (b), (c), (d), (e), (f), (g), (h), and (i) wherein E is N.

(k) One embodiment relates to compounds of formula 1 and embodiments (a), (b), (c), (e), (f), (g), (h), (i), and (j) wherein the compound has the substantially enantiomerically pure configuration below:

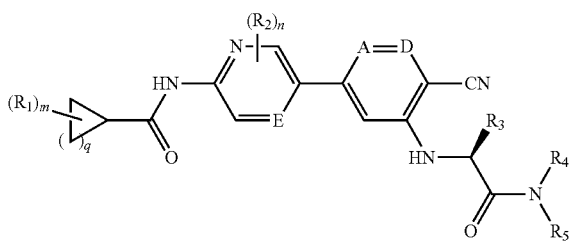

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991). It is also readily apparent that specific stereoisomers can be prepared by stereospecific synthesis using substantially enantiomerically pure starting materials or by separation of isomers by chromatography, recrystallization, either with or without auxiliaries, or other means.

Scheme A, step a, an amide forming reaction of an appropriate compound of formula (a) with an appropriate compound of formula (b) to give a compound of formula (c). An appropriate compound of formula (a) is one in which E, $R_2$, and n are as desired in the final compound of formula 1 and $X_1$ is a leaving group, such as halo. An appropriate compound of formula (b) is one in which $R_1$, q, and m are as desired in the final compound of formula 1 and $X_2$ is a group that participates in an amide forming reaction, such as hydroxyl or a leaving group, such as chloro, bromo, or imidazolyl, an activating moiety, a mixed anhydride of another carboxylic acid, such as formic acid, acetic acid, or represents the other part of a symmetrical anhydride formed from two compounds of formula (b).

For example, standard amide forming conditions can be used, such as those using coupling agents, including those used in peptide couplings, such as 2-(1H-7-azabenzotriazol-1-yl)-1,1,3,3-tetramethyluronium hexafluorophosphate methanaminium (HATU), dicyclohexylcarbodiimide (DCC), and 1-(3-dimethylaminopropyl)-3-ethylcarbodiimide hydrochloride. If necessary or desired, an additive such as 4-(dimethylamino)pyridine, 1-hydroxybenzotriazole, and the like may be used to facilitate the reaction. Such reactions are generally carried out using a base, such as N-methylmorpholine or triethylamine, in a wide variety of suitable solvents such as DCM, DMF, NMP, dimethylacetamide, THF, and the like. Such amide forming reactions are well understood and appreciated in the art.

Scheme A

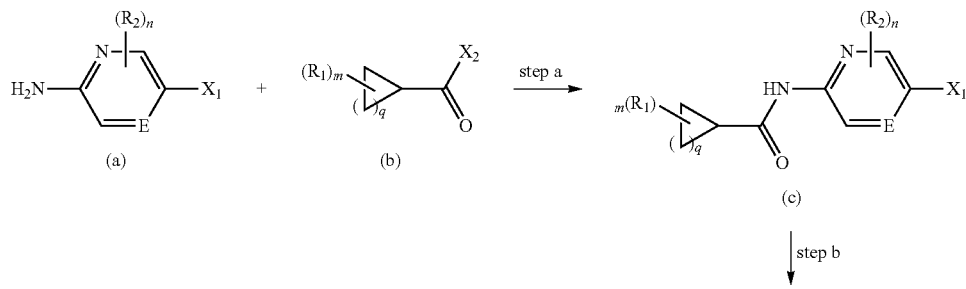

step b

-continued

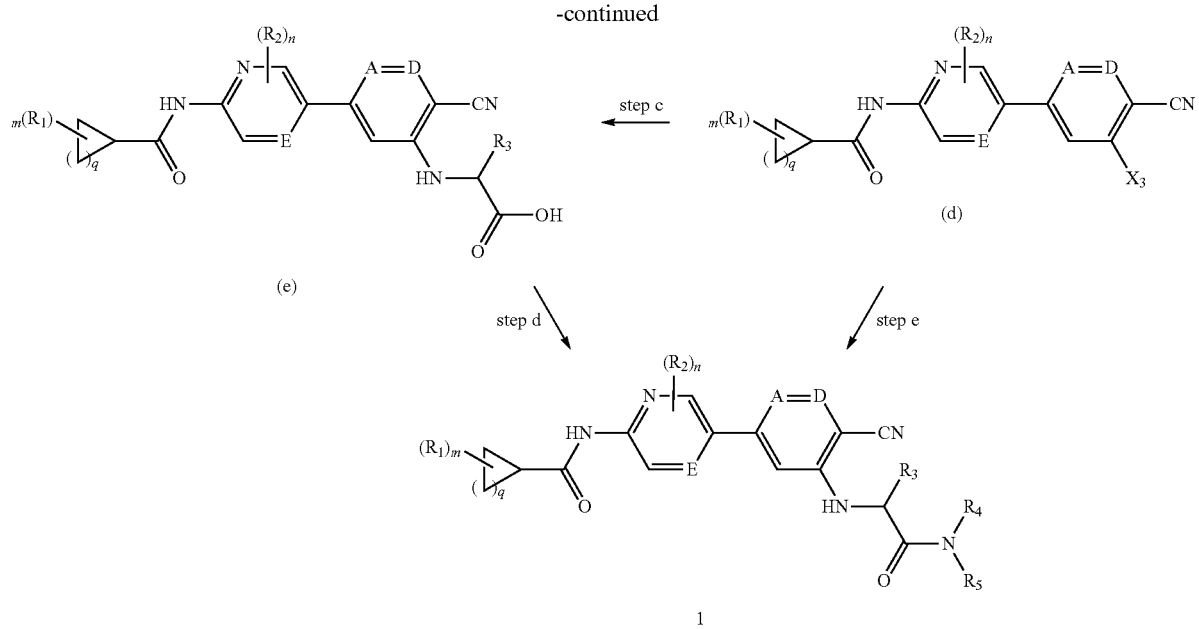

Scheme A, step b, depicts the coupling of an appropriate compound of formula (c) and an appropriate boronic acid or boronic ester of, the formula (f) below, to give a compound of formula (d).

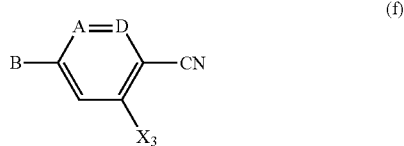

An appropriate compound of formula (c) is one in which $R_1$, $R_2$, E, q, m, and n are defined in formula 1 and $X_1$ is as described above. An appropriate boronic acid or boronic ester of formula (f) is one in which B is a boronic acid ($-B(OH)_2$)) or boronic ester, A and D are as defined in formula 1, and $X_3$ is a leaving group, such as halo, in particular fluoro. Such reactions are generally known as a Suzuki reaction and are well known in the art. While a Suzuki reaction is depicted in Scheme A it is understood that other carbon-carbon bond forming coupling reactions can be used to produce compounds of formula (d).

Scheme A, steps c, depicts the reaction of an appropriate compound of formula (d) and an appropriate compound of formula (g) to give a compound of formula (e).

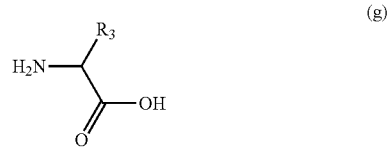

An appropriate compound of formula (d) is one in which $R_1$, $R_2$, m, q, n, E, A, and D are defined in formula 1 and $X_3$ is a leaving group, such as halo, in particular fluoro. An appropriate compound of (g) is one in which $R_3$ is as defined in formula 1 or gives rise to $R_3$ as desired in the final product of formula 1. It is understood that the reaction in step c is depicted with a carboxylic acid, but that the reaction can be carried out using a protected carboxylic acid, followed by deprotection, to give a compound of formula (e). It will be readily recognized that compounds of formula (g) include many of the common and uncommon amino acids, many of which are available as their protected versions. It will also be understood that an appropriate compound of formula (g) may have the stereochemistry desired in the final compound of formula 1.

For example, the reaction is generally carried out in a solvent (e.g., acetonitrile, DMSO, NMP, etc.) and in the presence of a base, (e.g., sodium carbonate or potassium carbonate) at elevated temperature (e.g., 75-150° C.).

Scheme A, step d, an amide forming reaction of an appropriate compound of formula (e) with an appropriate compound amine of formula (h), $HN(R_4)(R_5)$, to give a compound of formula 1. An appropriate compound of formula (e) is one in which $R_1$, $R_2$, m, q, n, E, A, D, and $R_3$ are defined in formula 1 or give rise to $R_3$ as defined in formula 1 and an appropriate compound of formula (h) is one in which $R_4$ and $R_5$ are as desired in the final compound of formula 1 or give rise to $R_4$ and $R_5$ as defined in formula 1. The amide forming reaction depicted in step d is carried out as discussed in step a and as is well known in the art.

Scheme A, step e, depicts the reaction of an appropriate compound of formula (d) with and appropriate compound of formula (i) to give a compound of formula 1.

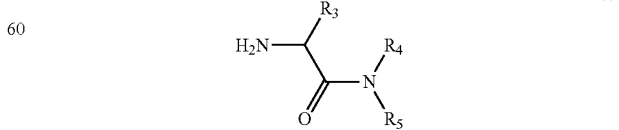

An appropriate compound of formula (d) is described above. An appropriate compound of formula (i) is one in which $R_3$, $R_4$, and $R_5$ are as desired in the final compound of formula 1 or give rise to $R_3$, $R_4$, and $R_5$ as defined in formula 1. It will also be understood that an appropriate compound of formula (i) may have the stereochemistry desired in the final compound of formula 1.

Such reactions are readily carried out as discussed in step c above and as is well known in the art.

It will be recognized by one of ordinary skill in the art that the compounds in Scheme A can be elaborated in a variety of ways to give compounds of formula 1. Such reactions include hydrolysis, oxidation, reduction, alkylation, amidations, sulfonations, and the like.

It will also be recognized that the order of the steps on Scheme A is not critical. For example, an amino protected compound of formula (a) can be used in Scheme A, step a, and carried through steps b and c and then d or e and then deprotected and amidated as described in step a.

Also, in an optional step, not shown, the compounds of formula 1 can be converted to pharmaceutically acceptable salts by methods well known and appreciated in the art.

The following examples are intended to be illustrative and non-limiting, and represent specific embodiments of the present invention.

Proton nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), and $CD_3OD$ (deuteromethanol or methanol-$d_4$). The mass spectra were recorded using either electrospray ionization (ESI) or atmospheric pressure chemical ionization.

The examples below were carried out in appropriate vessels and were typically stirred. Where indicated, products of certain preparations and examples are purified by mass-triggered HPLC (e.g., Pump: Waters™ 2525; MS: ZQ™; Software: MassLynx™), flash chromatography, or preparative thin layer chromatography (TLC). Reverse phase chromatography can be carried out using a variety of systems, including on a column (Gemini™ 5μ C18 110A, Axia™, ID30×75 mm, 5μ) under acidic conditions, eluting with acetonitrile (ACN) and water mobile phases containing 0.035% and 0.05% trifluoroacetic acid (TFA), respectively, or 0.1% formic acid (FA) in 20/80 (v/v) water/methanol or under basic conditions, eluting with water and 20/80 (v/v) water/acetonitrile mobile phases, both containing 10 mM $NH_4HCO_3$; or (XSelect™ C18, 5μ, ID30×75 mm) under acidic conditions, eluting with ACN and water mobile phases containing 0.1% FA or under basic conditions, eluting with 0.1% ammonium hydroxide in water (pH=9.5-10) and 0.1% ammonium hydroxide in ACN (pH=9.5-10). After isolation by chromatography, the solvent was removed and the product was obtained by evaporating product containing fractions (e.g., GeneVac™), rotary evaporator, evacuated flask, lyophilization, etc.

As used herein terms have their using conventional abbreviations, unless otherwise indicated, for example: methanol (MeOH), ethanol (EtOH), isopropanol (IPA), n-butanol (n-BuOH), acetonitrile (MeCN), tetrahydrofuran (THF), ethyl acetate (EtOAc), isopropyl acetate (IPAc), methyl ethyl ketone (MEK), methylisobutyl ketone (MIBK), dichloromethane (DCM), dimethyl sulfoxide (DMSO), dimethylformamide (DMF), N-methyl-2-pyrrolidone (NMP), hydrochloric acid (HCl), diisopropylethylamine (DIEA or DIPEA), and the like.

INTERMEDIATE 1

N-(5-bromopyrazin-2-yl)cyclopropanecarboxamide

A mixture of 5-bromopyrazin-2-amine (5 g, 28.7 mmol) was dissolved in anhydrous pyridine (47.9 mL) and cooled to 0° C., to which cyclopropanecarbonyl chloride (2.96 mL, 28.7 mmol) was added dropwise. After 15 minutes diluted in EtOAc and washed with 1N HCl solution (3×). Concentrated in vacuo to afford the title compound as a yellow solid (6.8716 g, 99% yield).

INTERMEDIATE 2

N-(5-(4-cyano-3-fluorophenyl)pyrazin-2-yl)cyclopropanecarboxamide

A mixture of Pd(dppf)$_2$CHCl$_3$ adduct (0.217 g, 0.266 mmol), aqueous cesium carbonate solution (2M, 10.62 mL, 21.25 mmol), N-(5-bromopyrazin-2-yl)cyclopropanecarboxamide (1.35 g, 5.58 mmol), and 2-fluoro-4-(4,4,5,5-tetramethyl-1,3,2-dioxaborolan-2-yl)benzonitrile (1.312 g, 5.31 mmol) was dissolved in anhydrous dioxane (26.6 mL). The reaction was heated at 95° C. for 12 hours. The cooled reaction was diluted in deionized water (200 mL) and triturated to give a solid which was collected by vacuum filtration, washed with deionized water, followed by hexanes. The residue was purified via normal phase column chromatography on (Thomson™ Single Step 80 g) using a gradient of 20-100% EtOAc/Heptanes on the Teledyne ISCO CombiFlash™ Purification system. The collected fractions were concentrated and dried in vacuo to afford the title compound (693.6 mg, 46.3% yield).

INTERMEDIATE 3

N-(5-(6-cyano-5-fluoropyridin-3-yl)pyrazin-2-yl)cyclopropanecarboxamide

The title intermediate was prepared in a manner similar to Intermediate 2, except 3-fluoro-5-(4,4,5,5-tetramethyl-1,3,2-dioxaborolan-2-yl)picolinonitrile was used to afford the title compound (797.8 mg, 71.6% yield).

INTERMEDIATE 4

(2-cyano-5-(5-(cyclopropanecarboxamido)pyrazin-2-yl)phenyl)glycine

A mixture of potassium carbonate (1.224 g, 8.86 mmol), N-(5-(4-cyano-3-fluorophenyl)pyrazin-2-yl)cyclopropanecarboxamide (500 mg, 1.771 mmol), and glycine (1.330 g, 17.71 mmol) were dissolved in anhydrous DMSO (5.90 mL). The reaction was heated at 120° C. for 12 hours. The reaction was then diluted in deionized water (250 mL) and extracted with EtOAc (5×). The acidified aqueous layer with 1N HCl solution. Extracted with DCM/Isopropanol mixture (9:1, 15×). Combined all organics, back-washed with deionized water, and concentrated in vacuo. The product was purified by preparative HPLC (Sunfire™ C18, 5 μM, ID TFA) using a gradient of 5-95% ACN (with 0.035% TFA) in water (with 0.05% TFA) to afford the title compound (453.4 mg, 76% yield).

INTERMEDIATE5

(2-cyano-5-(5-(cyclopropanecarboxamido)pyrazin-2-yl)phenyl)alanine

The title compound was prepared in a manner similar to Intermediate 4, except 2-aminopropanoic acid was used.

INTERMEDIATE6

N-(5-(4-cyano-3,5-difluorophenyl)pyrazin-2-1)cyclopropanecarboxamide

The title compound was prepared in a manner similar to Intermediate 2, except (4-cyano-3,5-difluorophenyl)boronic acid was used.

INTERMEDIATE7

N-(5-bromopyrazin-2-yl)-2-methylcyclopropanecarboxamide

A mixture of 2-methylcyclopropanecarboxylic acid (0.973 mL, 9.99 mmol) and 1-chloro-N,N,2-trimethylprop-1-en-1-amine (1.982 mL, 14.98 mmol) were diluted in anhydrous DCM (100 mL) and stirred at room temperature for 15 minutes. 5-Bromopyrazin-2-amine (1.738 g, 9.99 mmol) was then added, followed by DIEA (3.49 mL, 19.98 mmol) and the reaction was stirred at room temperature for 2 hours. The reaction was then dried in vacuo and the resulting brown oil was suspended in water (50 mL) and extracted with EtOAc (3×25 mL), the combined organic layers were then washed with saturated brine, dried over magnesium sulfate, filtered and concentrated in vacuo. The product was purified via normal phase column chromatography using an isocratic gradient of 25% EtOAc/Hexanes on the Teledyne ISCO CombiFlash™ Purification system to afford the title compound as a pale yellow solid (1.95 g, 76% yield). 1H NMR (500 MHz, DMSO-d6) δ ppm 0.70-0.88 (m, 1 H) 1.00-1.15 (m, 4 H) 1.24-1.39 (m, 1 H) 1.73-1.82 (m, 1 H) 8.56-8.61 (m, 1 H) 9.12 (d, J=1.46 Hz, 1 H) 11.14-11.20 (m, 1 H). ESI-MS: m/z [M+H]+ 256.5.

INTERMEDIATE8

N-(5-(6-cyano-5-fluoropyridin-3-yl)pyrazin-2-yl)-2-methylcyclopropanecarboxamide A mixture of N-(5-bromopyrazin-2-yl)-2-methylcyclopropanecarboxamide (0.300 g, 1.171 mmol), 3-fluoro-5-(4,4,5,5-tetramethyl-1,3,2-dioxaborolan-2-yl)picolinonitrile (0.291 g, 1.171 mmol), 1,1'-bis(diphenylphosphino)ferrocene-palladium(II)dichloride dichloromethane complex (0.096 g, 0.117 mmol), and 2M solution of sodium carbonate (2.34 mL, 4.69 mmol) were dissolved in anhydrous dioxane (5.86 mL). The reaction was subjected to microwave irradiation at 130° C. for 30 minutes, then diluted with deionized water (50 mL) to give a precipitate which was collected by vacuum filtration, rinsed with additional water and the resulting filter cake was dried in a vacuum oven overnight and taken forward without further purification (0.372 g, crude quantitative yield). 1H NMR (500 MHz, DMSO-d6) δ ppm 0.70-0.91 (m, 1 H) 1.00-1.19 (m, 4 H) 1.28-1.44 (m, 1 H) 1.78-2.14 (m, 1 H) 8.70 (dd, J=10.25, 1.46 Hz, 1 H) 9.24 (d, J=1.46 Hz, 1 H) 9.30-9.38 (m, 1 H) 9.43-9.52 (m, 1 H) 11.29-11.37 (m, 1 H). ESI-MS: m/z [M+H]+ 298.6.

INTERMEDIATE9

2-((benzyloxy)methyl)-N-(5-bromopyrazin-2-yl)cyclopropanecarboxamide

A mixture of 2-((benzyloxy)methyl)cyclopropanecarboxylic acid (1138 mg, 5.52 mmol), 5-bromopyrazin-2-amine (800 mg, 4.60 mmol), and pyridine (1125 µl, 13.79 mmol) were dissolved in anhydrous acetonitrile (6568 µl). The reaction stirred at room temperature for 5 minutes, followed by addition of propylphosphonic anhydride solution (50 wt % in EtOAc) (5469 µl, 9.20 mmol) over the course of 30 minutes. The reaction continued stirring for 24 hours, then was concentrated in vacuo to afford as residue which was purified via normal phase column chromatography using an isocratic gradient of 5% MeOH/DCM on the Teledyne ISCO CombiFlash™ Purification system to afford the title compound as a dark yellow/brown solid which was used without further purification. 1H NMR (400 MHz, DMSO-d6) δ ppm 0.85-0.98 (m, 1 H) 1.03-1.13 (m, 1 H) 1.52-1.70 (m, 1 H) 1.97-2.07 (m, 1 H) 3.43-3.63 (m, 2 H) 4.43-4.53 (m, 2 H) 7.24-7.40 (m, 5 H) 8.56-8.64 (m, 1 H) 9.12 (d, J=1.26 Hz, 1 H) 11.23-11.33 (m, 1 H). ESI-MS: m/z [M+H]+ 362.1.

INTERMEDIATE10

2-((benzyloxy)methyl)-N-(5-(6-cyano-5-fluoropyridin-3-yl)pyrazin-2-yl)cyclopropanecarboxamide A mixture of 2-((benzyloxy)methyl)-N-(5-bromopyrazin-2-yl)cyclopropanecarboxamide (0.600 g, 1.656 mmol), 3-fluoro-5-(4,4,5,5-tetramethyl-1,3,2-dioxaborolan-2-yl)picolinonitrile (0.411 g, 1.656 mmol), PdCl2(dppf) dichloromethane adduct (0.135 g, 0.166 mmol), and 2M sodium carbonate (3.31 mL, 6.63 mmol) were dissolved in anhydrous dioxane (8.28 mL). The reaction was subjected to microwave irradiation at 100° C. for 1 hour then diluted in DCM (30 mL), stirred at room temperature for 15 minutes and then passed through a medium fritted filter funnel and pad of Celite™. The remaining solids were dissolved in deionized water (30 mL) and the aqueous layer was also passed through the pad of Celite™. The aqueous layer was extracted with additional DCM (1×30 mL), the combined organic layer was washed with saturated brine (1×40 mL), dried over magnesium sulfate, filtered, and concentrated in vacuo and then dried under high vacuum to afford the title compound as a dark brown oil (0.668 g, crude quantitative yield). ESI-MS: m/z [M+H]+ 404.2.

EXAMPLE 1

(S)-N-(5-(4-cyano-3-((1-(dimethylamino)-1-oxopropan-2-yl)amino)phenyl)pyrazin-2-yl)cyclopropanecarboxamide

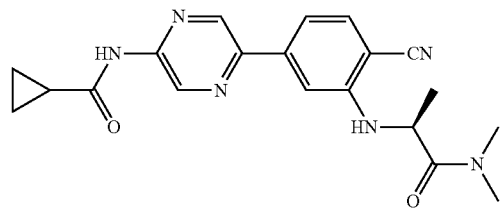 [SMILES: C[C@H](Nc1cc(-c2cnc(NC(=O)C3CC3)cn2)ccc1C#N)C(=O)N(C)C]

A mixture of 5-bromopyrazin-2-amine (1 g, 5.75 mmol) was dissolved in anhydrous pyridine (11.49 mL) and cooled to 0° C., to which cyclopropanecarbonyl chloride (0.661 g, 6.32 mmol) was added dropwise. After 15 minutes the reaction mixture was diluted with EtOAc (50 mL) and extracted with 1N HCl solution (3×20 mL). Then the organic layer was concentrated in vacuo to afford N-(5-bromopyrazin-2-yl)cyclopropanecarboxamide as a tan solid (1.1 g, 79% yield).

A mixture of Pd(dppf)2 CHCl3 adduct (0.340 g, 0.413 mmol), aqueous cesium carbonate solution (2M, 8.62 mL, 16.52 mmol), N-(5-bromopyrazin-2-yl)cyclopropanecarboxamide (1.0 g, 4.13 mmol), and (4-cyano-3-fluorophenyl)boronic acid (0.818 g, 4.96 mmol) were dissolved in anhydrous dioxane (14 mL). The reaction was subjected to microwave irradiation at 100° C. for one hour. Then the layers were separated and the organic layer was filtered through a pad of Celite™ and concentrated in vacuo to give a residue which was purified via normal phase column chromatography on (Thomson™ Single Step 25 g) using a gradient of 20-100% EtOAc/Heptanes on the Teledyne ISCO CombiFlash™ Purification system to afford N-(5-(4-cyano-3-fluorophenyl)pyrazin-2-yl)cyclopropanecarboxamide (566 mg, 48.5% yield).

A mixture of (S)-tert-butyl (1-(dimethylamino)-1-oxopropan-2-yl)carbamate (260.5 mg, 1.204 mmol) was dissolved in anhydrous DCM (1 mL) and then trifluoroacetic acid (3 mL, 38.9 mmol) was added dropwise. The reaction stirred at room temperature overnight. The reaction was concentrated in vacuo to afford (S)-2-amino-N,N-dimethylpropanamide as its trifluoroacetic acid salt which was used without further purification.

A mixture of N-(5-(4-cyano-3-fluorophenyl)pyrazin-2-yl)cyclopropanecarboxamide (50 mg, 0.177 mmol), potassium carbonate (122 mg, 0.886 mmol), and (S)-2-amino-N,N-dimethylpropanamide trifluoroacetic acid salt (335 mg) were dissolved in anhydrous DMSO (1000 µl). The reaction was heated at 120° C. for 12 hours, then purified by preparative HPLC (Sunfire™ C18, 5 µM, ID TFA) using a gradient of 5-95% ACN (with 0.035% TFA) in water (with 0.05% TFA). The pure fractions were combined and concentrated in vacuo to afford the title compound as a yellow solid (4.0 mg, 5.97%). 1H NMR (400 MHz, methanol-d4) δ ppm 0.89-0.97 (m, 2 H) 0.99-1.06 (m, 2 H) 1.29 (s, 2 H) 1.46 (d, J=6.57 Hz, 3 H) 1.93 (s, 1 H) 2.15 (s, 2 H) 2.99 (s, 3 H) 3.25 (s, 3 H) 7.36 (dd, J=8.08, 1.01 Hz, 1 H) 7.42 (s, 1 H) 7.55 (d, J=8.08 Hz, 1 H) 9.43 (br. s., 1 H) ESI-MS m/z [M+H]+ 379.0.

EXAMPLE 2 (R)-N-(5-(4-cyano-3-((1-(dimethylamino)-1-oxopropan-2-yl)amino)phenyl)pyrazin-2-yl)cyclopropanecarboxamide

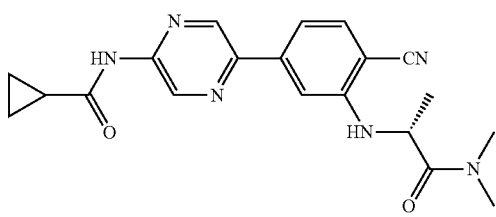

The title compound was prepared in a manner similar to Example 1, except (R)-2-amino-N,N-dimethylpropanamide was used to afford the title compound as a yellow semisolid (6.1 mg, 9.10%). 1H NMR (400 MHz, methanol-d4) δ ppm 0.90-0.98 (m, 2 H) 0.99-1.06 (m, 2 H) 1.29 (s, 3 H) 1.34-1.40 (m, 2 H) 1.46 (d, J=6.57 Hz, 3 H) 1.93 (s, 1 H) 2.02 (d, J=7.33 Hz, 1 H) 2.99 (s, 3 H) 3.25 (s, 3 H) 7.36 (dd, J=8.21, 1.39 Hz, 1 H) 7.40-7.43 (m, 1 H) 7.55 (d, J=8.34 Hz, 1H) 8.86 (br. s., 1 H) 9.43 (s, 1 H) ESI-MS m/z [M+H]+ 379.0.

EXAMPLE 3

N-(5-(4-cyano-3-((1-(dimethylamino)-1-oxopropan-2-yl)amino)phenyl)pyrazin-2-yl)cyclopropanecarboxamide

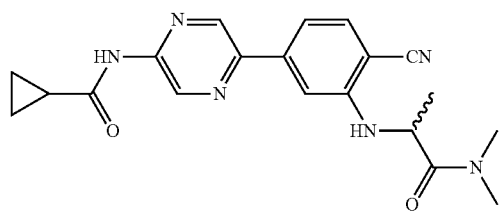

The title compound was prepared in a manner similar to Example 1, except 2-amino-N,N-dimethylpropanamide was used to afford the title compound as a light yellow solid (7.3 mg, 10.89% yield). 1H NMR (400 MHz, methanol-d4) δ ppm 0.91-0.97 (m, 2 H) 1.00-1.06 (m, 2 H) 1.25 (s, 1 H) 1.46 (d, J=6.57 Hz, 3 H) 1.93 (s, 1 H) 2.15 (s, 1 H) 2.66 (s, 3 H) 2.99 (s, 3 H) 3.25 (s, 3 H) 7.37 (dd, J=8.08, 1.52 Hz, 1 H) 7.43 (d, J=1.26 Hz, 1 H) 7.55 (d, J=8.08 Hz, 1 H) 8.87 (d, J=1.52 Hz, 1 H) 9.43 (d, J=1.26 Hz, 1 H). ESI-MS m/z [M+H]+ 379.0.

EXAMPLE 4

N-(5-(4-cyano-3-((2-(dimethylamino)-2-oxoethyl)amino)phenyl)pyrazin-2-yl)-2-methylcyclopropanecarboxamide

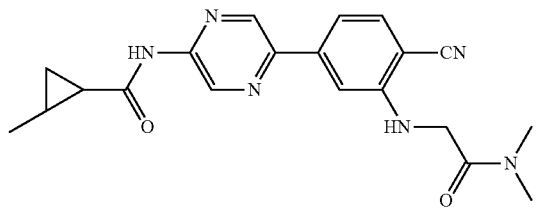

A mixture of aqueous cesium carbonate solution (2M, 3736 µl, 7.47 mmol), Pd (dppf)2 CHCl3 adduct (154 mg, 0.187 mmol), 5-bromopyrazin-2-amine (325 mg, 1.868 mmol), and 2-fluoro-4-(4,4,5,5-tetramethyl-1,3,2-dioxaborolan-2-yl)benzonitrile (461 mg, 1.868 mmol) were dissolved in anhydrous dioxane (6000 µl). The reaction was subjected to microwave irradiation at 100° C. for one hour. Filtered through a 12 mL fritted syringe with a Millipore™ (Hydrophilic PTFE 0.45 µm) microfilter, containing a pad of Celite™ and concentrated in vacuo to afford 4-(5-aminopyrazin-2-yl)-2-fluorobenzonitrile.

A mixture of 2-methylcyclopropanecarboxylic acid (182 µl, 1.867 mmol) and 1-chloro-N,N,2-trimethylprop-1-en-1-amine (371 µl, 2.80 mmol) were dissolved in anhydrous DCM (9000 µl) and stirred at room temperature for 15 minutes while under nitrogen. 4-(5-Aminopyrazin-2-yl)-2-fluorobenzonitrile (400 mg, 1.867 mmol) was added followed by DIPEA (651 µl, 3.73 mmol). The reaction was stirred at room temperature for 15 hours and then the solvent was removed in vacuo, to give a residue which was suspended in deionized water, and extracted with DCM (4×). Combined organics, washed with brine, and concentrated in vacuo. The product was purified by preparative HPLC (Sunfire™ C18, 5 µM, ID TFA) using a gradient of 20-60% ACN (with 0.035% TFA) in water (with 0.05% TFA). The pure fractions were combined and concentrated in vacuo to afford N-(5-(4-cyano-3-fluorophenyl)pyrazin-2-yl)-2-methylcyclopropanecarboxamide (91.4 mg, 16.52% yield).

A mixture of N-(5-(4-cyano-3-fluorophenyl)pyrazin-2-yl)-2-methylcyclopropanecarboxamide (51.4 mg, 0.173 mmol) and 2-amino-N,N-dimethylacetamide (267 µl, 2.60 mmol were combined in anhydrous DMSO (1000 µl) and heated at 120° C. for 24 hours. Reaction volume was then doubled in MeOH and purified by preparative HPLC (Sunfire™ C18, 5 µM, ID TFA) using a gradient of 35-60% ACN (with 0.035% TFA) in water (with 0.05% TFA). The pure fractions were combined and concentrated in vacuo to afford the title compound as a yellow oil (5.4 mg, 8.23%). 1H NMR (400 MHz, methanol-d4) δ ppm 0.78 (ddd, J=7.89, 6.38, 3.92 Hz, 1 H) 1.16-1.26 (m, 4 H) 1.39-1.47 (m, 1 H) 1.66 (dt, J=8.02, 4.20 Hz, 1 H) 2.98-3.03 (m, 4 H) 3.10-3.15 (m, 3 H) 4.16-4.21 (m, 2 H) 7.33-7.39 (m, 2 H) 7.54 (d, J=7.83 Hz, 1 H) 8.87 (s, 1 H) 9.39-9.45 (m, 1 H); ESI-MS m/z [M+H]+ 379.0.

EXAMPLE 5

N-(5-(4-cyano-3-((1-(dimethylamino)-3-methyl-1-oxobutan-2-yl)amino)phenyl)pyrazin-2-yl)cyclopropanecarboxamide

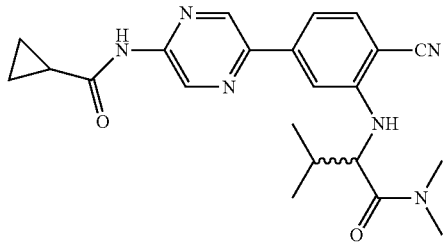 [SMILES: CC(C)C(Nc1cc(-c2cnc(NC(=O)C3CC3)cn2)ccc1C#N)C(=O)N(C)C]

A mixture of potassium carbonate (73.4 mg, 0.531 mmol), N-(5-(4-cyano-3-fluorophenyl)pyrazin-2-yl)cyclopropanecarboxamide (30 mg, 0.106 mmol), and DL-valine (125 mg, 1.063 mmol) were dissolved in anhydrous DMSO (531 µl). The reaction was heated at 120° C. for 12 hours, then diluted in deionized water and extracted with EtOAc (5×). Set aside organics and acidified aqueous layer with 1N HCl solution. Extracted with DCM/Isopropanol mixture (9:1, 15×). Combined all organics, back-washed with deionized water, and the organic layer was concentrated in vacuo to afford 2-((2-cyano-5-(5-(cyclopropanecarboxamido)pyrazin-2-yl)phenyl)amino)-3-methylbutanoic acid (104 mg).

A mixture of 2-((2-cyano-5-(5-(cyclopropanecarboxamido)pyrazin-2-yl)phenyl)amino)-3-methylbutanoic acid (104 mg, 0.137 mmol), dimethylamine, HCl (13.41 mg, 0.164 mmol), and DIPEA (71.6 µl, 0.411 mmol) were dissolved in anhydrous DMF (1000 µl) while under nitrogen. Reaction was stirred at room temperature for 30 minutes, followed by addition of HATU (62.5 mg, 0.164 mmol). Continued to stir at room temperature for 24 hours, then diluted in EtOAc (2 mL), and washed with saturated solution of sodium bicarbonate (1 mL), then brine (1 mL). The organic layer was concentrated in vacuo and purified by preparative HPLC (Sunfire™ C18, 5 µM, ID TFA) using a gradient of 40-65% ACN (with 0.035% TFA) in water (with 0.05% TFA). The pure fractions were combined and concentrated in vacuo to afford the title compound as a yellowish-orange solid (4.3 mg, 7.72% yield). 1H NMR (400 MHz, DMSO-d6) δ ppm 0.86-0.96 (m, 7 H) 1.01 (d, J=6.82 Hz, 3 H) 2.03-2.16 (m, 3 H) 2.85-2.90 (m, 3 H) 3.20 (s, 3 H) 4.81 (dd, J=8.59, 5.31 Hz, 1 H) 5.64 (d, J=8.84 Hz, 1 H) 7.43 (dd, J=8.21, 1.39 Hz, 1 H) 7.60-7.66 (m, 2 H) 9.06 (d, J=1.52 Hz, 1 H) 9.41 (d, J=1.26 Hz, 1 H) 11.23 (s, 1 H). ESI-MS m/z [M+H]+ 407.0.

EXAMPLE 6

N-(5-(4-cyano-3-((1-(dimethylamino)-1-oxobutan-2-yl)amino)phenyl)pyrazin-2-yl)cyclopropanecarboxamide

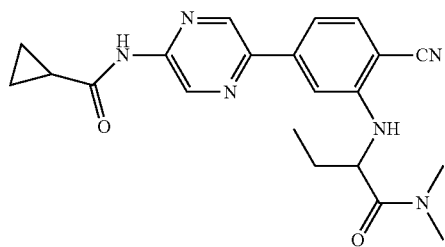 [SMILES: CCC(Nc1cc(-c2cnc(NC(=O)C3CC3)cn2)ccc1C#N)C(=O)N(C)C]

The title compound was prepared in a manner similar to Example 5, except 2-aminobutanoic acid was used to afford the title compound (2.6 mg, 6.24% yield). 1H NMR (400 MHz, DMSO-d6) δ ppm 0.82-0.94 (m, 8 H) 1.66-1.77 (m, 1 H) 1.81-1.92 (m, 1 H) 2.03-2.13 (m, 1 H) 2.90 (s, 3 H) 3.17 (s, 3 H) 4.86-4.96 (m, 1 H) 5.92 (d, J=7.83 Hz, 1 H) 7.42 (dd, J=8.08, 1.52 Hz, 1 H) 7.51-7.58 (m, 1 H) 7.64 (d, J=8.08 Hz, 1 H) 9.06 (d, J=1.52 Hz, 1 H) 9.41 (d, J=1.52 Hz, 1 H) 11.24 (s, 1 H). ESI-MS m/z [M+H]+ 393.0.

EXAMPLE 7

(S)-N-(5-(4-cyano-3-((1-(dimethylamino)-4-methoxy-1-oxobutan-2-yl)amino)phenyl)pyrazin-2-yl)cyclopropanecarboxamide

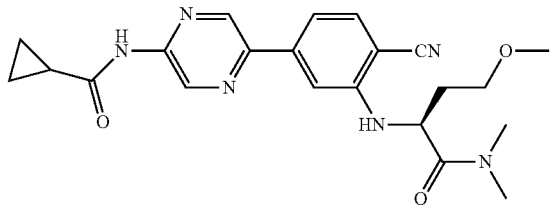 [SMILES: COCC[C@H](Nc1cc(-c2cnc(NC(=O)C3CC3)cn2)ccc1C#N)C(=O)N(C)C]

The title compound was prepared in a manner similar to Example 5, except (S)-2-amino-4-methoxybutanoic acid was used to afford the title compound as a light yellow solid (2.9 mg, 6.46% yield). 1H NMR (400 MHz, DMSO-d6) δ ppm 0.77-0.86 (m, 4 H) 1.74-1.85 (m, 1 H) 1.92-2.03 (m, 2 H) 2.81 (s, 3 H) 3.07 (s, 3 H) 3.14-3.19 (m, 3 H) 3.31-3.38 (m, 2 H) 4.77-4.86 (m, 1 H) 6.02 (d, J=8.08 Hz, 1 H) 6.44 (s, 1 H) 7.36 (dd, J=8.08, 1.26 Hz, 1 H) 7.40-7.45 (m, 1 H) 7.56 (d, J=8.08 Hz, 1 H) 8.95 (d, J=1.52 Hz, 1 H) 9.34 (d, J=1.26 Hz, 1 H) 11.17 (s, 1H). ESI-MS m/z [M+H]+ 423.0.

EXAMPLE 8

N-(5-(4-cyano-3-((1-(dimethylamino)-4,4-difluoro-1-oxobutan-2-yl)amino)phenyl)pyrazin-2-yl)cyclopropanecarboxamide

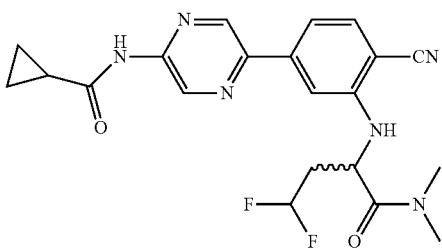 [SMILES: CN(C)C(=O)C(CC(F)F)Nc1cc(-c2cnc(NC(=O)C3CC3)cn2)ccc1C#N]

The title compound was prepared in a manner similar to Example 5, except 2-amino-4,4-difluorobutanoic acid was used to afford the title compound as a yellowish-orange solid (9.1 mg, 19.97% yield). 1H NMR (400 MHz, DMSO-d6) δ ppm 0.84-0.94 (m, 4 H) 2.02-2.09 (m, 1 H) 2.32-2.46 (m, 2 H) 2.55 (s, 2 H) 2.85-2.92 (m, 2 H) 3.16 (s, 2 H) 5.00 (d, J=8.34 Hz, 1 H) 6.15-6.25 (m, 1 H) 7.43-7.53 (m, 2 H) 7.66 (d, J=8.34 Hz, 1 H) 9.04 (d, J=1.52 Hz, 1 H) 9.41 (d, J=1.52 Hz, 1 H) 11.25 (s, 1 H). ESI-MS m/z [M+H]+ 429.0.

EXAMPLE 9

(S)-N-(5-(3-((1-(azetidin-1-yl)-1-oxopropan-2-yl)amino)-4-cyanophenyl)pyrazin-2-yl)cyclopropanecarboxamide

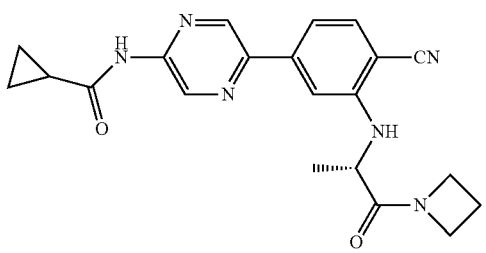 [SMILES: C[C@H](Nc1cc(-c2cnc(NC(=O)C3CC3)cn2)ccc1C#N)C(=O)N1CCC1]

The title compound was prepared in a manner similar to Example 5, except (S)-2-aminopropanoic acid was used, followed by azetidine, HCl to afford the title compound as a light yellow solid (14.6 mg, 43.8% yield). 1H NMR (400 MHz, DMSO-d6) δ ppm 0.83-0.95 (m, 5 H) 1.24 (br. s., 2 H) 1.31-1.40 (m, 3 H) 2.01-2.12 (m, 1 H) 2.26 (t, J=7.45 Hz, 2 H) 2.72 (s, 1 H) 3.86-3.98 (m, 2 H) 4.24 (q, J=8.08 Hz, 1 H) 4.38-4.49 (m, 2 H) 7.39-7.48 (m, 2 H) 7.64 (d, J=8.59 Hz, 1 H) 9.05 (s, 1 H) 9.42 (s, 1 H) 11.25 (s, 1 H). ESI-MS m/z [M+H]+ 391.0.

EXAMPLE 10

(S)-N-(5-(4-cyano-3-((1-oxo-1-(pyrrolidin-1-yl)propan-2-yl)amino)phenyl)pyrazin-2-yl)cyclopropanecarboxamide

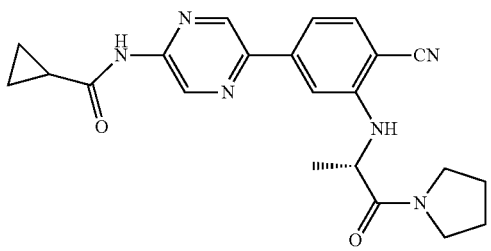 [SMILES: C[C@H](Nc1cc(-c2cnc(NC(=O)C3CC3)cn2)ccc1C#N)C(=O)N1CCCC1]

The title compound was prepared in a manner similar to Example 5, except (S)-2-aminopropanoic acid was used, followed by pyrrolidine to afford the title compound as a light yellow solid (5.2 mg, 15.06% yield). 1H NMR (400 MHz, DMSO-d6) δ ppm 0.88-0.91 (m, 4 H) 1.30-1.34 (m, 1 H) 1.77-2.02 (m, 4 H) 2.05-2.09 (m, 1 H) 2.87-2.95 (m, 1 H) 3.36-3.55 (m, 2 H) 3.79 (dt, J=9.85, 6.57 Hz, 1 H) 4.64 (quin, J=6.69 Hz, 1 H) 6.00 (d, J=7.33 Hz, 1 H) 7.39-7.49 (m, 2 H) 7.60-7.67 (m, 1 H) 9.05 (d, J=1.52 Hz, 1 H) 9.37-9.44 (m, 1 H) 11.26 (s, 1H). ESI-MS m/z [M+H]+ 405.0.

EXAMPLE 11

(S)-N-(5-(4-cyano-3-((1-(3-hydroxyazetidin-1-yl)-1-oxopropan-2-yl)amino)phenyl)pyrazin-2-yl)cyclopropanecarboxamide

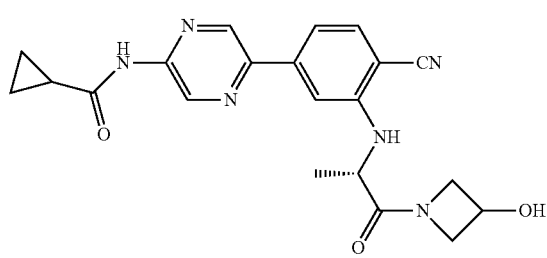 [SMILES: C[C@H](Nc1cc(-c2cnc(NC(=O)C3CC3)cn2)ccc1C#N)C(=O)N1CC(O)C1]

The title compound was prepared in a manner similar to Example 5, except (S)-2-aminopropanoic acid was used, followed by azetidin-3-ol, HCl to afford the title compound as a yellow solid (7.7 mg, 22.19% yield). 1H NMR (400 MHz, DMSO-d6) δ ppm 0.88-0.91 (m, 3 H) 1.14-1.28 (m, 2 H) 1.34-1.42 (m, 3 H) 2.04-2.10 (m, 1 H) 3.65 (dt, J=10.17, 4.89 Hz, 1 H) 3.93-4.02 (m, 1 H) 4.02-4.17 (m, 1 H) 4.40-4.56 (m, 1 H) 5.93 (br. s., 1 H) 7.38-7.47 (m, 2 H) 7.65 (d, J=8.59 Hz, 1 H) 8.97-9.08 (m, 1 H) 9.38-9.45 (m, 1 H) 11.20-11.30 (m, 1 H). ESI-MS m/z [M+H]+ 407.0.

EXAMPLE 12

(S)-N-(5-(4-cyano-3-((1-(ethyl(methyl)amino)-1-oxopropan-2-yl)amino)phenyl)pyrazin-2-yl)cyclopropanecarboxamide

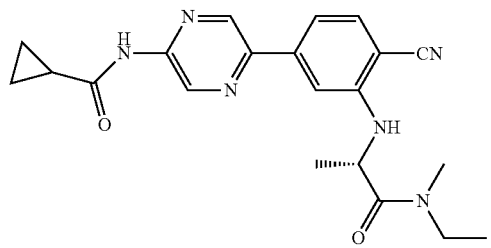 [SMILES: CCN(C)C(=O)[C@H](C)Nc1cc(-c2cnc(NC(=O)C3CC3)cn2)ccc1C#N]

The title compound was prepared in a manner similar to Example 5, except (S)-2-aminopropanoic acid was used, followed by except N-methylethanamine to afford the title compound as a light yellow solid (4.3 mg, 12.83% yield). 1H NMR (400 MHz, DMSO-d6) δ ppm 1.03 (t, J=7.07 Hz, 2 H) 1.19-1.23 (m, 1 H) 1.35 (dd, J=6.44, 3.92 Hz, 3 H) 2.06-2.09 (m, 1 H) 2.86 (s, 1 H) 3.14 (s, 2 H) 4.78-4.89 (m, 1 H) 5.91-6.05 (m, 1 H) 7.42 (dt, J=8.15, 1.99 Hz, 1 H) 7.49 (d, J=16.93 Hz, 1 H) 7.64 (dd, J=8.21, 1.39 Hz, 1 H) 9.04-9.09 (m, 1 H) 9.39-9.43 (m, 1 H) 11.24 (s, 1 H). ESI-MS m/z [M+H]+ 393.0.

EXAMPLE 13

(S)-N-(5-(4-cyano-3-((1-((2-hydroxyethyl)amino)-1-oxopropan-2-yl)amino)phenyl)pyrazin-2-yl)cyclopropanecarboxamide

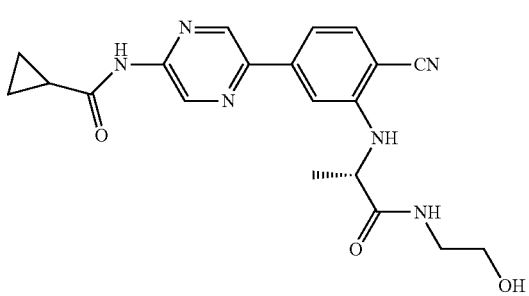 [SMILES: C[C@H](Nc1cc(-c2cnc(NC(=O)C3CC3)cn2)ccc1C#N)C(=O)NCCO]

The title compound was prepared in a manner similar to Example 5, except (S)-2-aminopropanoic acid was used, followed by 2-aminoethanol to afford the title compound as a light yellow solid (2.9 mg, 8.61% yield). 1H NMR (400 MHz, DMSO-d6) δ ppm 0.90 (s, 3 H) 1.24 (s, 1 H) 1.40 (s, 2 H) 2.07 (s, 1 H) 2.55 (s, 2 H) 3.18 (s, 2 H) 4.27 (s, 1 H) 5.90 (s, 1 H) 7.37 (s, 1 H) 7.45 (s, 1 H) 7.65 (s, 1 H) 9.00 (s, 1 H) 9.40 (s, 1 H) 11.26 (s, 1 H). ESI-MS m/z [M+H]+ 395.0.

EXAMPLE 14

(S)-N-(5-(4-cyano-3-((1-(isopropylamino)-1-oxopropan-2-yl)amino)phenyl)pyrazin-2-yl)cyclopropanecarboxamide

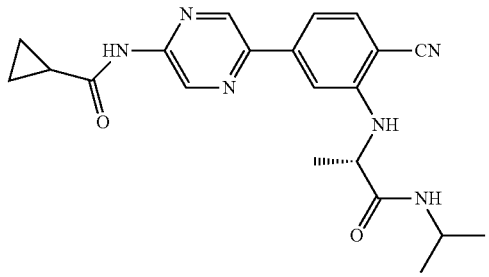 [SMILES: CC(C)NC(=O)[C@H](C)Nc1cc(-c2cnc(NC(=O)C3CC3)cn2)ccc1C#N]

The title compound was prepared in a manner similar to Example 5, except (S)-2-aminopropanoic acid was used, followed by propan-2-amine to afford the title compound as a light yellow solid (5.4 mg, 16.12% yield). 1H NMR (400 MHz, DMSO-d6) δ ppm 0.88 (br. s., 4 H) 1.03 (s, 6 H) 1.39 (s, 3 H) 2.06 (s, 1 H) 3.87 (s, 1 H) 4.17 (br. s., 1 H) 5.84 (br. s., 1 H) 7.37 (s, 1 H) 7.46 (s, 1 H) 7.64 (s, 1 H) 8.99 (s, 1 H) 9.40 (s, 1 H) 11.27 (s, 1 H). ESI-MS m/z [M+H]+ 393.0.

EXAMPLE 15

(S)-N-(5-(4-cyano-3-((1-((2-methoxyethyl)amino)-1-oxopropan-2-yl)amino)phenyl)pyrazin-2-yl)cyclopropanecarboxamide

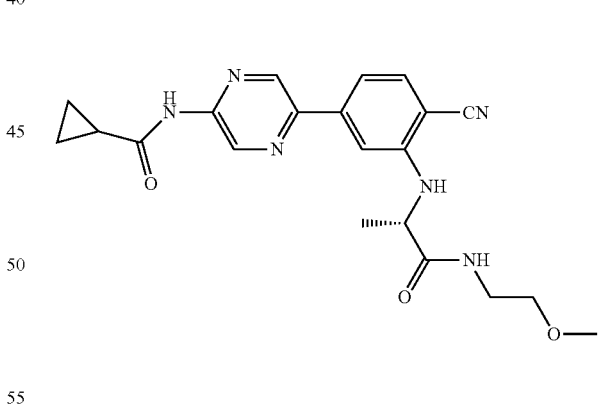

The title compound was prepared in a manner similar to Example 5, except (S)-2-aminopropanoic acid was used, followed by 2-methoxyethanamine to afford the title compound as a light yellow solid (3.9 mg, 11.18% yield). 1H NMR (400 MHz, DMSO-d6) δ ppm 0.87-0.92 (m, 3 H) 1.41 (d, J=6.82 Hz, 3 H) 2.07 (t, J=5.94 Hz, 1 H) 3.15 (s, 3 H) 3.22-3.30 (m, 3 H) 4.26 (t, J=7.07 Hz, 1 H) 5.88 (d, J=7.58 Hz, 1 H) 7.35 (s, 1 H) 7.44 (dd, J=8.21, 1.39 Hz, 1 H) 7.66 (d, J=8.08 Hz, 1 H) 8.22-8.29 (m, 1 H) 8.99 (d, J=1.52 Hz, 1 H) 9.40 (d, J=1.52 Hz, 1 H) 11.26 (s, 1 H). ESI-MS m/z [M+H]+ 409.0.

EXAMPLE 16

(S)-N-(5-(4-cyano-3-((1-(3-methoxyazetidin-1-yl)-1-oxopropan-2-yl)amino)phenyl)pyrazin-2-yl)cyclopropanecarboxamide

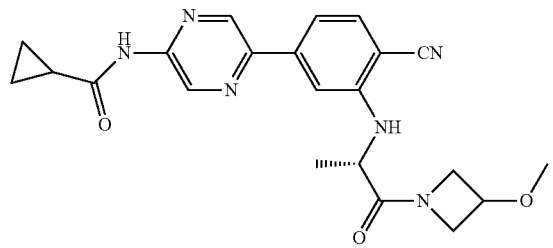 [SMILES: COC1CN(C(=O)[C@H](C)Nc2cc(-c3cnc(NC(=O)C4CC4)cn3)ccc2C#N)C1]

The title compound was prepared in a manner similar to Example 5, except (S)-2-aminopropanoic acid was used, followed by 3-methoxyazetidine, HCl to afford the title compound as a white solid (2.6 mg, 7.24% yield). 1H NMR (400 MHz, DMSO-d6) δ ppm 0.87-0.92 (m, 3 H) 1.25-1.29 (m, 2 H) 1.36 (dd, J=6.57, 1.26 Hz, 3 H) 2.06-2.11 (m, 1 H) 3.24 (d, J=4.55 Hz, 3 H) 3.68-3.77 (m, 1 H) 4.05-4.20 (m, 1 H) 4.20-4.32 (m, 1 H) 4.38-4.54 (m, 1 H) 5.91-5.98 (m, 1 H) 7.42-7.47 (m, 2 H) 7.65 (d, J=8.59 Hz, 1 H) 9.01-9.08 (m, 1 H) 9.43 (dd, J=4.67, 1.39 Hz, 1 H) 11.25 (d, J=3.54 Hz, 1 H). ESI-MS m/z [M+H]+ 421.0.

EXAMPLE 17

(S)-N-(5-(4-cyano-3-((1-((2-methoxyethyl)(methyl)amino)-1-oxopropan-2-yl)amino)phenyl)pyrazin-2-yl)cyclopropanecarboxamide

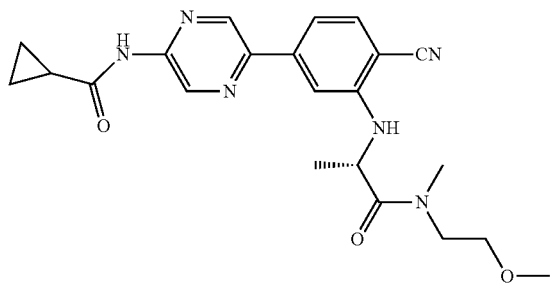 [SMILES: COCCN(C)C(=O)[C@H](C)Nc1cc(-c2cnc(NC(=O)C3CC3)cn2)ccc1C#N]

The title compound was prepared in a manner similar to Example 5, except (S)-2-aminopropanoic acid was used, followed by 2-methoxy-N-methylethanamine to afford the title compound as a light yellow solid (17.6 mg, 48.8% yield). 1H NMR (400 MHz, DMSO-d6) δ ppm 0.87-0.92 (m, 4 H) 1.35 (dd, J=6.44, 1.64 Hz, 3 H) 2.03-2.12 (m, 1 H) 3.17-3.23 (m, 5 H) 3.49-3.59 (m, 5 H) 4.81-4.93 (m, 1 H) 6.00 (d, J=7.07 Hz, 1 H) 7.41-7.51 (m, 2 H) 7.64 (d, J=8.08 Hz, 1 H) 9.05 (dd, J=7.83, 1.52 Hz, 1 H) 9.42 (d, J=1.52 Hz, 1 H) 11.24 (s, 1 H). ESI-MS m/z [M+H]+ 423.0.

EXAMPLE 18

N-(5-(4-cyano-3-((1-(dimethylamino)-3-hydroxy-1-oxopropan-2-yl)amino)phenyl)pyrazin-2-yl)cyclopropanecarboxamide (3.6 mg, 9.13 μmol, 8.60% yield)

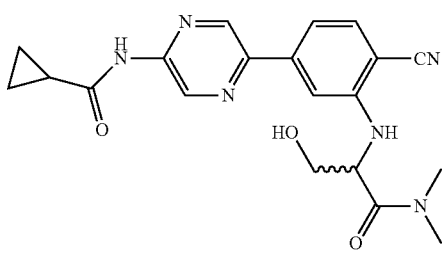 [SMILES: CN(C)C(=O)C(CO)Nc1cc(-c2cnc(NC(=O)C3CC3)cn2)ccc1C#N]

The title compound was prepared in a manner similar to Example 5, except DL-serine was used to afford the title compound as a pale yellow solid (3.6 mg, 8.6% yield). 1H NMR (400 MHz, DMSO-d6) δ ppm 0.88-0.91 (m, 3 H) 2.05-2.11 (m, 1 H) 2.90 (s, 2 H) 3.18 (s, 3 H) 3.67-3.75 (m, 2 H) 4.93 (dt, J=7.64, 5.02 Hz, 1 H) 5.10-5.15 (m, 1 H) 5.94 (d, J=7.58 Hz, 1 H) 7.41 (dd, J=8.21, 1.39 Hz, 1 H) 7.54-7.56 (m, 1 H) 7.63 (d, J=8.34 Hz, 1 H) 9.05 (d, J=1.52 Hz, 1 H) 9.41 (d, J=1.52 Hz, 1 H) 11.24 (s, 1 H). ESI-MS m/z [M+H]+ 395.0.

EXAMPLE 19

(S)-N-(5-(4-cyano-3-((1-((2-hydroxyethyl)(methyl)amino)-1-oxopropan-2-yl)amino)phenyl)pyrazin-2-yl)cyclopropanecarboxamide

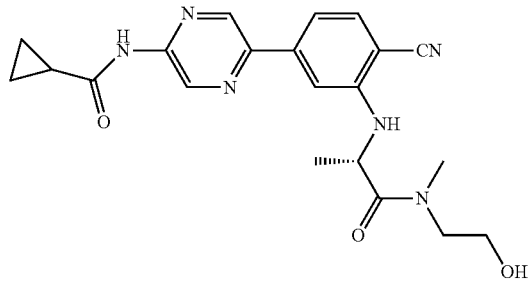 [SMILES: C[C@H](Nc1cc(-c2cnc(NC(=O)C3CC3)cn2)ccc1C#N)C(=O)N(C)CCO]

The title compound was prepared in a manner similar to Example 5, except (S)-2-aminopropanoic acid was used, followed by 2-(methylamino)ethanol to afford the title compound as a pale yellow semisolid (1.7 mg, 4.87% yield). 1H NMR (400 MHz, methanol-d4) δ ppm 0.94 (dt, J=7.83, 3.16 Hz, 2 H) 1.00-1.06 (m, 2 H) 1.48 (d, J=6.57 Hz, 3 H) 1.93 (s, 1 H) 2.65 (s, 3 H) 2.99 (s, 1 H) 3.55 (s, 1 H) 3.81 (s, 2 H) 7.35-7.45 (m, 1 H) 7.45-7.57 (m, 1 H) 8.87 (s, 1 H) 9.39-9.44 (m, 1 H). ESI-MS m/z [M+H]+ 409.0.

EXAMPLE 20

N-(5-(4-cyano-3-((2-(ethyl(methyl)amino)-2-oxo-ethyl)amino)phenyl)pyrazin-2-yl)cyclopropanecarboxamide

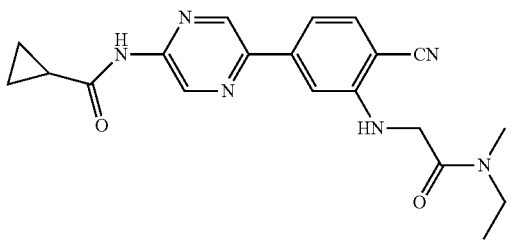 [SMILES: CCN(C)C(=O)CNc1cc(-c2cnc(NC(=O)C3CC3)cn2)ccc1C#N]

The title compound was prepared in a manner similar to Example 5, except glycine was used, followed by N-methylethanamine to afford the title compound as a pale yellow solid (18.5 mg, 55% yield). 1H NMR (400 MHz, DMSO-d6) δ ppm 0.90 (s, 4 H) 1.06 (s, 2 H) 1.19 (s, 1 H) 2.08 (s, 1 H) 2.89 (s, 1 H) 3.05 (s, 2 H) 3.43 (s, 2 H) 4.14 (s, 2 H) 6.10 (s, 1 H) 7.42 (br. s., 2 H) 7.63 (s, 1 H) 9.08 (s, 1 H) 9.41 (s, 1 H) 11.25 (s, 1 H). ESI-MS m/z [M+H]+ 379.0.

EXAMPLE 21

N-(5-(3-((2-(azetidin-1-yl)-2-oxoethyl)amino)-4-cyanophenyl)pyrazin-2-yl)cyclopropanecarboxamide

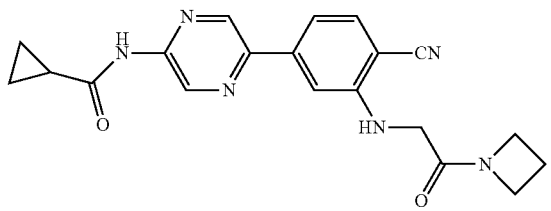 [SMILES: N#Cc1ccc(-c2cnc(NC(=O)C3CC3)cn2)cc1NCC(=O)N1CCC1]

The title compound was prepared in a manner similar to Example 5, except glycine was used, followed by azetidine, HCl to afford the title compound as a pale yellow solid (7.7 mg, 23% yield). 1H NMR (400 MHz, DMSO-d6) δ ppm 0.90 (s, 4 H) 2.07 (s, 1 H) 2.28 (s, 2 H) 3.96 (br. s., 4 H) 4.25 (s, 2 H) 6.08 (br. s., 1 H) 7.37 (s, 2 H) 7.63 (s, 1 H) 9.05 (s, 1 H) 9.41 (s, 1 H) 11.25 (s, 1 H). ESI-MS m/z [M+H]+ 377.0.

EXAMPLE 22

N-(5-(4-cyano-3-((2-(3-methoxyazetidin-1-yl)-2-oxoethyl)amino)phenyl)pyrazin-2-yl)cyclopropanecarboxamide

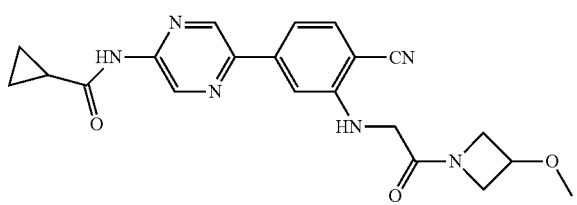 [SMILES: COC1CN(C(=O)CNc2cc(-c3cnc(NC(=O)C4CC4)cn3)ccc2C#N)C1]

The title compound was prepared in a manner similar to Example 5, except glycine was used, followed by 3-methoxyazetidine, HCl to afford the title compound as a pale yellow solid (5.9 mg, 16.32% yield). 1H NMR (400 MHz, DMSO-d6) δ ppm 0.90 (s, 4 H) 2.07 (s, 1 H) 3.24 (s, 3 H) 3.73 (br. s., 1 H) 4.00 (br. s., 2 H) 4.10 (br. s., 2 H) 4.27 (s, 1 H) 4.43 (s, 1 H) 6.11 (s, 1 H) 7.36 (s, 1 H) 7.43 (s, 1 H) 7.63 (s, 1 H) 9.03 (s, 1 H) 9.42 (s, 1 H) 11.25 (s, 1 H). ESI-MS m/z [M+H]+ 407.0.

EXAMPLE 23

(S)-N-(5-(4-cyano-3-((1-(dimethylamino)-1-oxobutan-2-yl)amino)phenyl)pyrazin-2-yl)cyclopropanecarboxamide

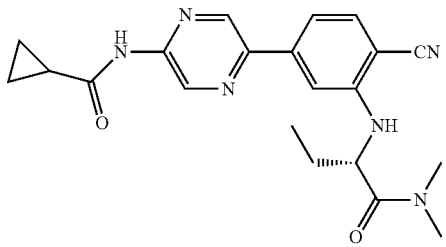

The title compound was prepared in a manner similar to Example 5, except (S)-2-aminobutanoic acid was used to afford the title compound as a pale yellow semisolid (2.5 mg, 6% yield). 1H NMR (400 MHz, DMSO-d6) δ ppm 0.86-0.90 (m, 4 H) 1.63-1.87 (m, 1 H) 2.09 (s, 4 H) 2.90 (s, 3 H) 3.17 (d, J=2.02 Hz, 3 H) 4.84-4.97 (m, 1 H) 5.91 (s, 1 H) 6.51 (br. s., 3 H) 7.41 (s, 1 H) 7.54 (s, 1 H) 7.63 (s, 1 H) 9.06 (s, 1 H) 9.42 (s, 1 H) 11.24 (s, 1 H). ESI-MS m/z [M+H]+ 393.0.

EXAMPLE 24

N-(5-(4-cyano-3-((2-(3,3-difluoroazetidin-1-yl)-2-oxoethyl)amino)phenyl)pyrazin-2-yl)cyclopropanecarboxamide

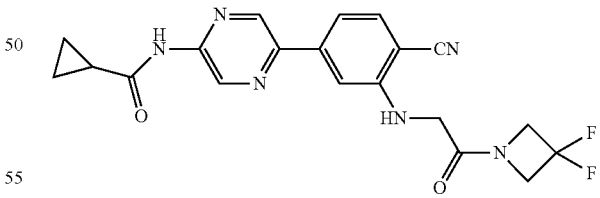

The title compound was prepared in a manner similar to Example 5, except glycine was used, followed by 3,3-difluoroazetidine, HCl to afford the title compound as an orange solid (17 mg, 46.4% yield). 1H NMR (400 MHz, DMSO-d6) δ ppm 0.80-0.84 (m, 4 H) 1.95-2.01 (m, 1 H) 4.02 (s, 2 H) 4.31 (t, J=12.51 Hz, 2 H) 4.68 (t, J=12.25 Hz, 2 H) 7.29 (d, J=1.26 Hz, 1 H) 7.36 (dd, J=8.08, 1.52 Hz, 1 H) 7.57 (d, J=8.08 Hz, 1 H) 8.95 (d, J=1.52 Hz, 1 H) 9.33 (d, J=1.52 Hz, 1 H) 11.18 (s, 1 H). ESI-MS m/z [M+H]+ 413.0.

EXAMPLE 25

N-(5-(4-cyano-3-((2-(cyclopropyl(methyl)amino)-2-oxoethyl)amino)phenyl)pyrazin-2-yl)cyclopropanecarboxamide

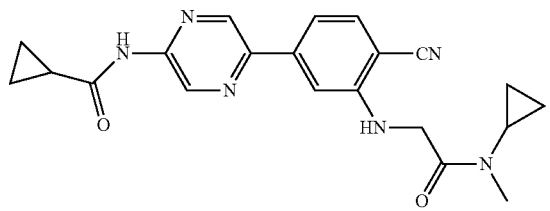 [SMILES: CN(C(=O)CNc1cc(-c2cnc(NC(=O)C3CC3)cn2)ccc1C#N)C1CC1]

The title compound was prepared in a manner similar to Example 5, except glycine was used, followed by N-methylcyclopropanamine to afford the title compound as a pale yellow solid (13.1 mg, 37.7% yield). 1H NMR (400 MHz, DMSO-d6) δ ppm 0.90 (s, 8 H) 2.07 (s, 1 H) 2.88 (s, 3 H) 4.34 (br. s., 2 H) 6.16 (br. s., 1 H) 7.43 (s, 2 H) 7.65 (s, 1 H) 9.05 (s, 1 H) 9.41 (s, 1 H) 11.24 (s, 1 H). ESI-MS m/z [M+H]+ 391.0.

EXAMPLE 26

(R)-N-(5-(4-cyano-3-((1-(dimethylamino)-1-oxobutan-2-yl)amino)phenyl)pyrazin-2-yl)cyclopropanecarboxamide

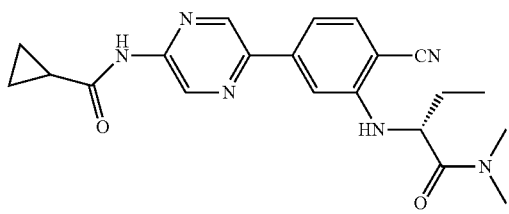 [SMILES: CC[C@@H](Nc1cc(-c2cnc(NC(=O)C3CC3)cn2)ccc1C#N)C(=O)N(C)C]

The title compound was prepared in a manner similar to Example 5, except (R)-2-aminobutanoic acid was used to afford the title compound as a pale yellow solid (2.7 mg, 6.53% yield). 1H NMR (400 MHz, DMSO-d6) δ ppm 0.86 (s, 6 H) 1.71 (s, 1 H) 1.87 (s, 1 H) 2.06 (s, 1 H) 2.90 (s, 3 H) 3.17 (s, 3 H) 4.90 (br. s., 1 H) 5.91 (s, 1 H) 7.43 (s, 1 H) 7.54 (s, 1 H) 7.65 (s, 1 H) 9.06 (s, 1 H) 9.42 (s, 1 H) 11.24 (s, 1 H). ESI-MS m/z [M+H]+ 393.0.

EXAMPLE 27

N-(5-(4-cyano-3-((2-(3-hydroxypyrrolidin-1-yl)-2-oxoethyl)amino)phenyl)pyrazin-2-yl)cyclopropanecarboxamide

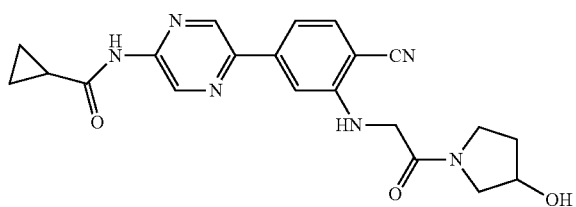 [SMILES: N#Cc1ccc(-c2cnc(NC(=O)C3CC3)cn2)cc1NCC(=O)N1CCC(O)C1]

The title compound was prepared in a manner similar to Example 5, except glycine was used, followed by pyrrolidin-3-ol, HCl to afford the title compound as a pale yellow solid (13.9 mg, 38.5% yield). 1H NMR (400 MHz, DMSO-d6) δ ppm 0.90 (s, 3 H) 1.89 (br. s., 1 H) 2.08 (s, 1 H) 3.40 (br. s., 2 H) 3.63 (br. s., 2 H) 4.08 (s, 1 H) 4.13 (s, 1 H) 6.07 (s, 1 H) 7.42 (s, 2 H) 7.66 (s, 1 H) 9.06 (s, 1 H) 9.42 (s, 1 H) 11.25 (s, 1 H). ESI-MS m/z [M+H]+ 407.0.

EXAMPLE 28

N-(5-(4-cyano-3-((1-(dimethylamino)-4-hydroxy-1-oxobutan-2-yl)amino)phenyl)pyrazin-2-yl)cyclopropanecarboxamide

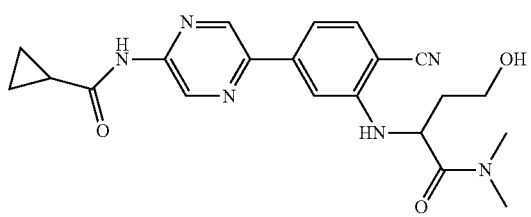

The title compound was prepared in a manner similar to Example 5, except DL-homoserine was used to afford the title compound as a yellow solid (2.4 mg, 7.47% yield). 1H NMR (400 MHz, DMSO-d6) δ ppm 0.90 (s, 8 H) 1.16 (s, 6 H) 2.07 (s, 1 H) 2.88 (s, 3 H) 3.17 (s, 3 H) 4.04 (s, 1 H) 7.52 (s, 1 H) 7.62 (s, 1 H) 9.01 (s, 1 H) 9.41 (s, 1 H) 11.24 (s, 1 H). ESI-MS m/z [M+H]+ 409.0.

EXAMPLE 29

N-(5-(4-cyano-3-((1-((2-hydroxyethyl)(methyl)amino)-1-oxobutan-2-yl)amino)phenyl)pyrazin-2-yl)cyclopropanecarboxamide

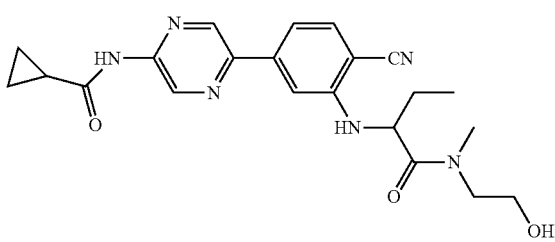 [SMILES: CCC(Nc1cc(-c2cnc(NC(=O)C3CC3)cn2)ccc1C#N)C(=O)N(C)CCO]

The title compound was prepared in a manner similar to Example 5, except 2-aminobutanoic acid was used, followed by 2-(methylamino)ethanol to afford the title compound as a yellow solid (14.2 mg, 4.45% yield). 1H NMR (400 MHz, DMSO-d6) δ ppm 0.90 (s, 7 H) 1.74 (s, 1 H) 1.88 (br. s., 1 H) 2.09 (s, 3 H) 2.89 (s, 1 H) 3.39 (br. s., 1 H) 3.50 (s, 1 H) 3.60 (br. s., 1 H) 4.88 (br. s., 1 H) 7.41 (br. s., 1 H) 7.53 (s, 1 H) 7.62 (s, 1 H) 9.04 (s, 1 H) 9.41 (s, 1 H) 11.24 (s, 1 H). ESI-MS m/z [M+H]+ 423.0.

EXAMPLE 30

(R)-N-(5-(6-cyano-5-((1-(dimethylamino)-1-oxopropan-2-yl)amino)pyridin-3-yl)pyrazin-2-yl)cyclopropanecarboxamide

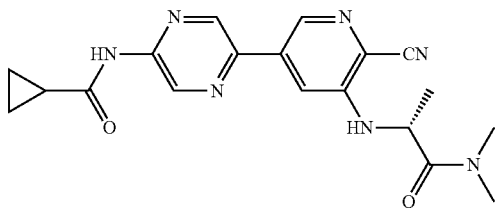

A mixture of N-(5-(6-cyano-5-fluoropyridin-3-yl)pyrazin-2-yl)cyclopropanecarboxamide, potassium carbonate (171 mg, 1.236 mmol), and (R)-2-aminopropanoic acid (220 mg, 2.471 mmol) were dissolved in anhydrous DMSO (618 μl). The reaction was heated at 120° C. for 1 hour, then added 1N HCl solution to give a solid which was collected by vacuum filtration while washing with deionized water followed by hexanes to afford (R)-2-((2-cyano-5-(5-(cyclopropanecarboxamido)pyrazin-2-yl)pyridin-3-yl)amino)propanoic acid (87 mg, crude quantitative yield).

A mixture of (R)-2-((2-cyano-5-(5-(cyclopropanecarboxamido)pyrazin-2-yl)pyridin-3-yl)amino)propanoic acid (15.3 mg, 0.043 mmol), dimethylamine, HCl (3.54 mg, 0.043 mmol), and DIPEA (22.69 μl, 0.130 mmol) were dissolved in anhydrous DMF (109 μl). while under nitrogen. Reaction was stirred at room temperature for 30 minutes, followed by addition of HATU (19.81 mg, 0.052 mmol). The reaction continued to stir at room temperature for 24 hours. Doubled reaction volume with DMF and purified by HPLC Method A, preparative HPLC (Sunfire™ C18, 5 μM, ID TFA) using a gradient of 25-50% ACN (with 0.035% TFA) in water (with 0.05% TFA). The pure fractions were combined and concentrated in vacuo to afford the title compound as a pale yellow solid (10.1 mg, 61.3% yield). 1H NMR (400 MHz, DMSO-d6) δ ppm 0.91 (s, 4 H) 1.35 (s, 3 H) 2.08 (br. s., 1 H) 2.91 (s, 3 H) 3.14 (s, 3 H) 4.91 (s, 1 H) 6.25 (s, 1 H) 7.93 (s, 1 H) 8.64 (s, 1 H) 9.15 (s, 1 H) 9.46 (s, 1 H) 11.35 (s, 1 H). ESI-MS m/z [M+H]+ 380.0.

EXAMPLE 31

(R)-N-(5-(6-cyano-5-((1-(dimethylamino)-1-oxobutan-2-yl)amino)pyridin-3-yl)pyrazin-2-yl)cyclopropanecarboxamide

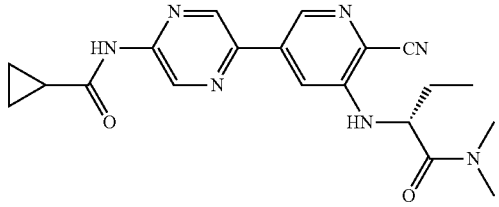 [SMILES: CC[C@@H](Nc1cc(-c2cnc(NC(=O)C3CC3)cn2)cnc1C#N)C(=O)N(C)C]

The title compound was prepared in a manner similar to Example 30, except (R)-2-aminobutanoic acid was used to afford the title compound as a pale yellow solid (1.8 mg, 1.842% yield). 1H NMR (400 MHz, DMSO-d6) δ ppm 0.91 (s, 6 H) 1.24 (s, 1 H) 1.83 (s, 1 H) 2.07 (br. s., 1 H) 2.90 (s, 3 H) 3.15 (s, 3 H) 4.95 (br. s., 1 H) 6.16 (s, 1 H) 7.98 (s, 1 H) 8.64 (s, 1 H) 9.14 (s, 1 H) 9.46 (s, 1 H) 11.35 (s, 1 H). ESI-MS m/z [M+H]+ 394.0.

EXAMPLE 32

N-(5-(6-cyano-5-((((2S,3R)-1-(dimethylamino)-3-hydroxy-1-oxobutan-2-yl)amino)pyridin-3-yl)pyrazin-2-yl)cyclopropanecarboxamide

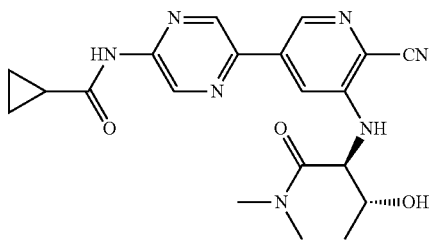 [SMILES: C[C@@H](O)[C@H](Nc1cc(-c2cnc(NC(=O)C3CC3)cn2)cnc1C#N)C(=O)N(C)C]

The title compound was prepared in a manner similar to Example 30, except (2S,3R)-2-amino-3-hydroxybutanoic acid was used to afford the title compound as a yellow solid (21.5 mg, 21.78% yield). 1H NMR (400 MHz, DMSO-d6) δ ppm 0.91 (s, 4 H) 1.17 (s, 3 H) 2.07 (s, 1 H) 2.88 (s, 3 H) 3.18 (s, 3 H) 4.06 (s, 1 H) 4.90 (br. s., 1 H) 5.88 (s, 1 H) 7.95 (s, 1 H) 8.62 (s, 1 H) 9.12 (s, 1 H) 9.46 (s, 1 H) 11.34 (s, 1 H). ESI-MS m/z [M+H]+ 410.0.

EXAMPLE 33

(R)-N-(5-(4-cyano-3-((1-(dimethylamino)-4,4-difluoro-1-oxobutan-2-yl)amino)phenyl)pyrazin-2-yl)cyclopropanecarboxamide

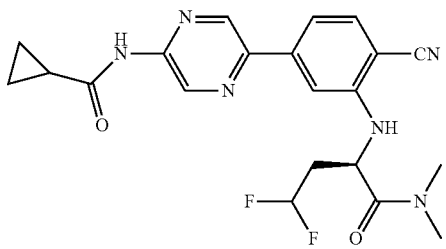 [SMILES: CN(C)C(=O)[C@@H](CC(F)F)Nc1cc(-c2cnc(NC(=O)C3CC3)cn2)ccc1C#N]

The title compound was prepared in a manner similar to Example 5, except 2-amino-4,4-difluorobutanoic acid, HCl was used. The product was purified by 1D preparative SFC/MS (Waters™ BEH-2EP (19×150 mm)) using a gradient of 10-40% MeOH in liquid CO2, followed by 2D preparative SFC/MS (DEAP (19×150 mm)) using an isocratic gradient of 30% MeOH in liquid CO2 to afford the title compound as a pale beige solid (2 mg, 1.319% yield). 1H NMR (400 MHz, methanol-d4) δ ppm 0.91-0.97 (m, 3 H) 1.00-1.06 (m, 2 H) 1.32-1.39 (m, 1 H) 1.89-1.99 (m, 1 H) 2.33-2.52 (m, 2 H) 2.98 (s, 3 H) 3.26 (s, 3 H) 5.00 (dd, J=7.83, 5.05 Hz, 1 H) 6.10 (dd, J=5.43, 3.66 Hz, 1 H) 7.44 (dd, J=8.08, 1.52 Hz, 1 H) 7.49 (d, J=1.01 Hz, 1 H) 7.59 (d, J=8.08 Hz, 1 H) 8.86 (br. s., 1 H) 9.44 (br. s., 1 H). ESI-MS m/z [M+H]+ 429.0.

EXAMPLE 34

(S)-N-(5-(4-cyano-3-((1-(dimethylamino)-4,4-difluoro-1-oxobutan-2-yl)amino)phenyl)pyrazin-2-yl)cyclopropanecarboxamide

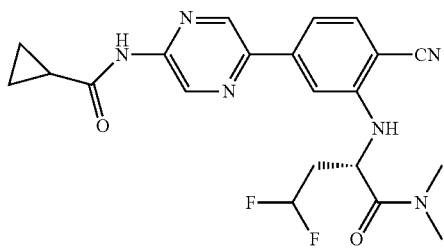

The title compound was prepared in a manner similar to Example 5, except 2-amino-4,4-difluorobutanoic acid, HCl was used. The product was purified by 1D preparative SFC/MS (Waters™ BEH-2EP (19×150 mm)) using a gradient of 10-40% MeOH in liquid CO2, followed by 2D preparative SFC/MS (DEAP (19×150 mm)) using an isocratic gradient of 30% MeOH in liquid CO2 to afford the title compound as a pale beige solid (2.4 mg, 1.583% yield). 1H NMR (400 MHz, DMSO-d6) δ ppm 0.87 (br. s., 5 H) 1.24 (s, 1 H) 2.33 (s, 2 H) 2.68 (s, 1 H) 2.88 (s, 4 H) 3.16 (s, 5 H) 5.01 (s, 1 H) 6.19 (s, 2 H) 7.45 (s, 2 H) 7.64 (s, 1 H) 9.01 (br. s., 1 H) 9.37 (br. s., 1 H). ESI-MS m/z [M+H]+ 429.0.

EXAMPLE 35

N-(5-(6-cyano-5-((1-((2-hydroxyethyl)(methyl)amino)-1-oxobutan-2-yl)amino)pyridin-3-yl)pyrazin-2-yl)cyclopropanecarboxamide

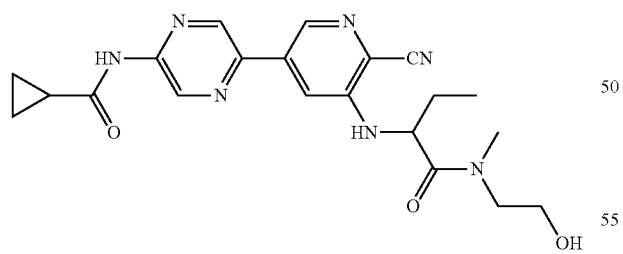

The title compound was prepared in a manner similar to Example 30, except 2-aminobutanoic acid was used, followed by 2-(methylamino)ethanol to afford the title compound as a yellow solid (7.5 mg, 49.9% yield). 1H NMR (400 MHz, DMSO-d6) δ ppm 0.89 (br. s., 6H) 1.77 (s, 1 H) 1.87 (br. s., 1 H) 2.08 (s, 1 H) 2.89 (s, 1 H) 3.20 (s, 2 H) 3.50 (s, 2 H) 3.58 (br. s., 1 H) 3.73 (br. s., 1 H) 4.93 (br. s., 1 H) 7.97 (br. s., 1 H) 8.62 (s, 1 H) 9.11 (s, 1 H) 9.46 (s, 1 H) 11.34 (s, 1 H). ESI-MS m/z [M+H]+ 424.0.

EXAMPLE 36

N-(5-(6-cyano-5-((1-(cyclopropyl(methyl)amino)-1-oxobutan-2-yl)amino)pyridin-3-yl)pyrazin-2-yl)cyclopropanecarboxamide

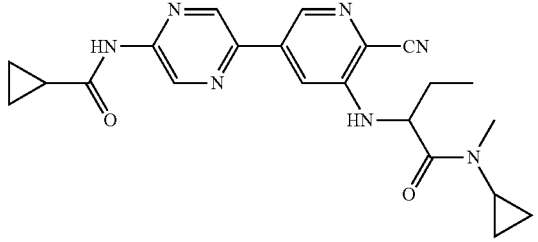 [SMILES: CCC(Nc1cc(-c2cnc(NC(=O)C3CC3)cn2)cnc1C#N)C(=O)N(C)C1CC1]

The title compound was prepared in a manner similar to Example 30, except 2-aminobutanoic acid was used, followed by N-methylcyclopropanamine, HCl to afford the title compound as a yellow solid (5.2 mg, 34.9% yield). 1H NMR (400 MHz, DMSO-d6) δ ppm 0.90 (s, 11 H) 1.89 (br. s., 1 H) 2.06 (s, 1 H) 2.85 (s, 3 H) 2.96 (br. s., 1 H) 3.08 (br. s., 1 H) 5.03 (br. s., 1 H) 6.13 (s, 1 H) 7.89 (s, 1 H) 8.68 (s, 1 H) 9.14 (s, 1 H) 9.45 (s, 1 H) 11.35 (s, 1 H). ESI-MS m/z [M+H]+ 420.0.

EXAMPLE 37

N-(5-(6-cyano-5-(((2R,3R)-1-(dimethylamino)-3-hydroxy-1-oxobutan-2-yl)amino)pyridin-3-yl)pyrazin-2-yl)cyclopropanecarboxamide

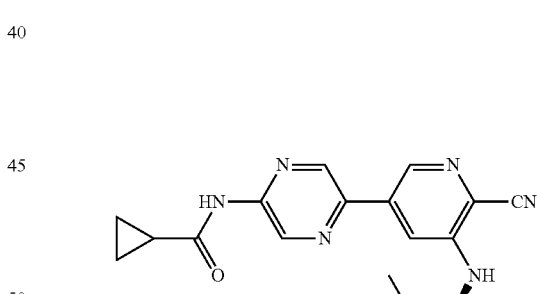

The title compound was prepared in a manner similar to Example 30, except (2R,3R)-2-amino-3-hydroxybutanoic acid was used to afford the title compound as a yellow solid (9.6 mg, 71.7% yield). 1H NMR (400 MHz, DMSO-d6) δ ppm 0.91 (s, 3 H) 1.07 (s, 3 H) 2.08 (s, 1 H) 2.90 (s, 3 H) 3.19 (s, 3 H) 3.97 (s, 1 H) 4.07 (s, 1 H) 4.90 (s, 1 H) 6.05 (s, 1 H) 8.14 (s, 1 H) 8.62 (s, 1 H) 9.10 (s, 1 H) 9.45 (s, 1 H) 11.34 (s, 1 H). ESI-MS m/z [M+H]+ 410.0.

EXAMPLE 38

N-(5-(6-cyano-5-(((2R,3S)-1-(dimethylamino)-3-hydroxy-1-oxobutan-2-yl)amino)pyridin-3-yl)pyrazin-2-yl)cyclopropanecarboxamide

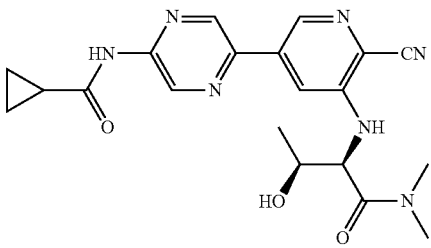 [SMILES: C[C@H](O)[C@@H](Nc1cc(-c2cnc(NC(=O)C3CC3)cn2)cnc1C#N)C(=O)N(C)C]

The title compound was prepared in a manner similar to Example 30, except (2R,3S)-2-amino-3-hydroxybutanoic acid was used to afford the title compound as a yellow solid (14.3 mg, 79% yield). 1H NMR (400 MHz, DMSO-d6) δ ppm 0.89 (s, 4 H) 1.16 (s, 3 H) 2.08 (s, 1 H) 2.88 (s, 3 H) 3.18 (s, 3 H) 4.06 (s, 1 H) 4.89 (br. s., 1 H) 5.88 (s, 1 H) 7.95 (s, 1 H) 8.63 (s, 1 H) 9.12 (s, 1 H) 9.46 (s, 1 H) 11.34 (s, 1 H). ESI-MS m/z [M+H]+ 410.0.

EXAMPLE 39

N-(5-(6-cyano-5-(((2S,3S)-1-(dimethylamino)-3-hydroxy-1-oxobutan-2-yl)amino)pyridin-3-yl)pyrazin-2-yl)cyclopropanecarboxamide

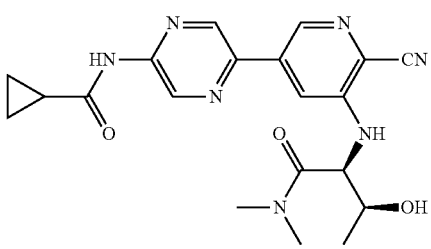 [SMILES: C[C@H](O)[C@H](Nc1cc(-c2cnc(NC(=O)C3CC3)cn2)cnc1C#N)C(=O)N(C)C]

The title compound was prepared in a manner similar to Example 30, except (2S,3S)-2-amino-3-hydroxybutanoic acid was used to afford the title compound as a yellow solid (8 mg, 23.64% yield). 1H NMR (400 MHz, DMSO-d6) δ ppm 0.91 (s, 4 H) 1.05 (s, 3 H) 2.06 (s, 1 H) 2.90 (s, 3 H) 3.19 (s, 3 H) 4.07 (s, 1 H) 4.94 (s, 1 H) 6.05 (s, 1 H) 8.14 (s, 1 H) 8.62 (s, 1 H) 9.10 (s, 1 H) 9.45 (s, 1 H) 11.34 (s, 1 H). ESI-MS m/z [M+H]+ 410.0.

EXAMPLE 40

N-(5-(6-cyano-5-((2-(methyl(2,2,2-trifluoroethyl)amino)-2-oxoethyl)amino)pyridin-3-yl)pyrazin-2-yl)cyclopropanecarboxamide

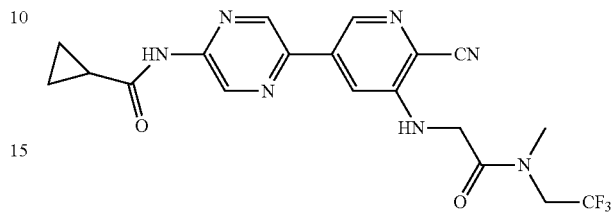

The title compound was prepared in a manner similar to Example 30, except 2-aminoacetic acid was used, followed by 2,2,2-trifluoro-N-methylethanamine, HCl to afford the title compound as a pale yellow solid (11.7 mg, 60.9% yield). 1H NMR (400 MHz, DMSO-d6) δ ppm 0.85-0.94 (m, 4 H) 2.07 (quin, J=6.19 Hz, 1 H) 2.98 (s, 1 H) 3.14-3.25 (m, 3 H) 4.16-4.30 (m, 2 H) 4.33-4.49 (m, 2 H) 6.39-6.60 (m, 1 H) 7.78 (d, J=1.77 Hz, 1 H) 8.64 (d, J=1.52 Hz, 1 H) 9.10 (d, J=1.52 Hz, 1 H) 9.44 (d, J=1.52 Hz, 1 H) 11.35 (s, 1 H). ESI-MS m/z [M+H]+ 434.0.

EXAMPLE 41

N-(5-(6-cyano-5-((1-(methyl(2,2,2-trifluoroethyl)amino)-1-oxopropan-2-yl)amino)pyridin-3-yl)pyrazin-2-yl)cyclopropanecarboxamide

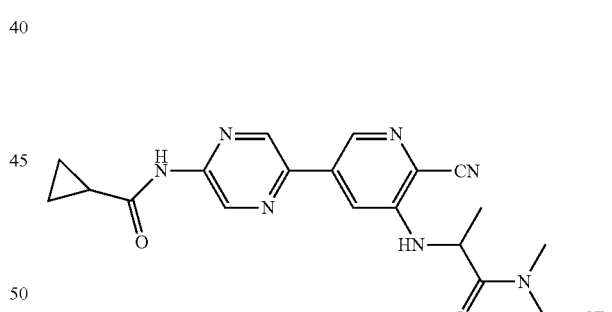

The title compound was prepared in a manner similar to Example 30, except 2-aminopropanoic acid was used, followed by 2,2,2-trifluoro-N-methylethanamine, HCl to afford the title compound as a pale yellow solid (12.4 mg, 57.4% yield). 1H NMR (400 MHz, DMSO-d6) δ ppm 0.91 (s, 3 H) 1.41 (s, 3 H) 2.08 (s, 1 H) 2.99 (s, 1 H) 3.29 (s, 3 H) 4.20 (s, 1 H) 4.29 (s, 1 H) 4.99 (s, 1 H) 6.30 (s, 1 H) 7.88 (s, 1 H) 8.66 (s, 1 H) 9.12 (s, 1 H) 9.45 (s, 1 H) 11.35 (s, 1H). ESI-MS m/z [M+H]+ 448.0.

EXAMPLE 42

N-(5-(6-cyano-5-((1-(dimethylamino)-3-methoxy-1-oxopropan-2-yl)amino)pyridin-3-yl)pyrazin-2-yl)cyclopropanecarboxamide

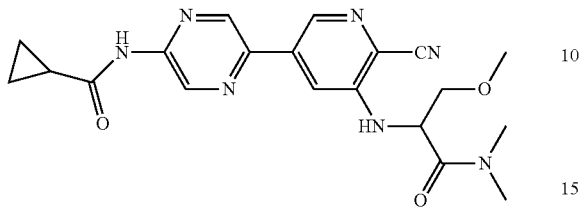

The title compound was prepared in a manner similar to Example 30, except 2-amino-3-methoxypropanoic acid was used to afford the title compound as a pale yellow solid (7.9 mg, 57.6% yield). 1H NMR (400 MHz, DMSO-d6) δ ppm 0.91 (s, 4 H) 2.08 (s, 1 H) 2.90 (s, 3 H) 3.16 (s, 3 H) 3.28 (s, 3 H) 3.65 (s, 2 H) 5.12 (br. s., 1 H) 6.18 (s, 1 H) 8.03 (s, 1 H) 8.65 (s, 1 H) 9.13 (s, 1 H) 9.46 (s, 1 H) 11.35 (s, 1 H). ESI-MS m/z [M+H]+ 410.0.

EXAMPLE 43

N-(5-(6-cyano-5-((1-((cyanomethyl)(methyl)amino)-1-oxopropan-2-yl)amino)pyridin-3-yl)pyrazin-2-yl)cyclopropanecarboxamide

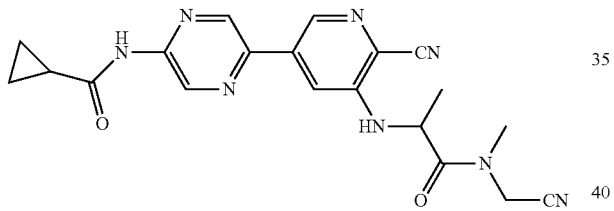

The title compound was prepared in a manner similar to Example 30, except 2-aminopropanoic acid was used, followed by 2-(methylamino)acetonitrile to afford the title compound as a pale yellow solid (10.7 mg, 46.6% yield). 1H NMR (400 MHz, DMSO-d6) δ ppm 0.84 (s, 4 H) 1.31 (s, 3 H) 1.99 (s, 1 H) 3.18 (s, 3 H) 4.40 (s, 2 H) 4.89 (s, 1 H) 6.23 (s, 1 H) 7.82 (s, 1 H) 8.59 (s, 1 H) 9.05 (s, 1 H) 9.39 (s, 1 H) 11.27 (s, 1 H). ESI-MS m/z [M+H]+ 405.0.

EXAMPLE 44

N-(5-(6-cyano-5-((3-cyano-1-(dimethylamino)-1-oxopropan-2-yl)amino)pyridin-3-yl)pyrazin-2-yl)cyclopropanecarboxamide

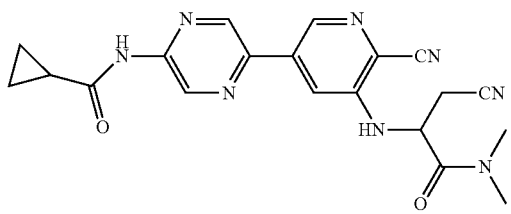 [SMILES: CN(C)C(=O)C(CC#N)Nc1cc(-c2cnc(NC(=O)C3CC3)cn2)cnc1C#N]

The title compound was prepared in a manner similar to Example 30, except 2-amino-3-cyanopropanoic acid was used to afford the title compound as a pale yellow solid (11 mg, 55.8% yield). 1H NMR (400 MHz, DMSO-d6) δ ppm 0.91 (s, 4 H) 2.07 (s, 1 H) 2.92 (s, 3 H) 3.10 (s, 4 H) 5.30 (s, 1 H) 6.65 (s, 1 H) 8.12 (s, 1 H) 8.70 (s, 1 H) 9.16 (s, 1 H) 9.47 (s, 1 H) 11.36 (s, 1 H). ESI-MS m/z [M+H]+ 405.0.

EXAMPLE 45

(R)-N-(5-(6-cyano-5-((2-(2-cyanopyrrolidin-1-yl)-2-oxoethyl)amino)pyridin-3-yl)pyrazin-2-yl)cyclopropanecarboxamide

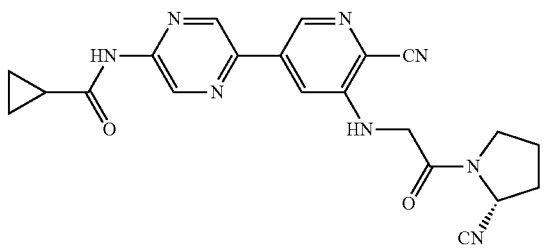

The title compound was prepared in a manner similar to Example 30, except glycine was used, followed by (R)-pyrrolidine-2-carbonitrile to afford the title compound as a pale yellow solid (4.5 mg, 24.37% yield). 1H NMR (400 MHz, DMSO-d6) δ ppm 0.91 (s, 4 H) 2.07 (br. s., 3 H) 2.19 (s, 2 H) 3.56 (s, 1 H) 3.74 (br. s., 1 H) 4.25 (s, 2 H) 4.82 (s, 1 H) 6.50 (s, 1 H) 7.79 (s, 1 H) 8.65 (s, 1 H) 9.11 (s, 1 H) 9.45 (s, 1 H) 11.34 (s, 1 H). ESI-MS m/z [M+H]+ 417.0.

EXAMPLE 46

N-(5-(6-cyano-5-((1-((2,2-difluoroethyl)(methyl)amino)-1-oxopropan-2-yl)amino)pyridin-3-yl)pyrazin-2-yl)cyclopropanecarboxamide

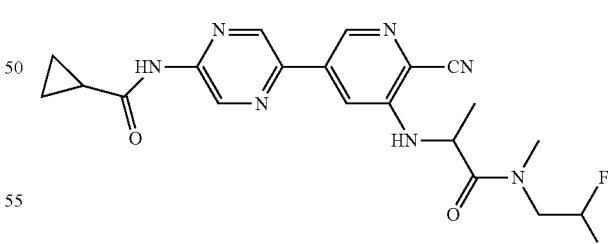

The title compound was prepared in a manner similar to Example 30, except alanine was used, followed by 2,2-difluoro-N-methylethanamine, HCl to afford the title compound as a yellow solid (18.9 mg, 51.7% yield). 1H NMR (400 MHz, DMSO-d6) δ ppm 0.91 (s, 4 H) 1.40 (s, 3 H) 2.97 (s, 1 H) 3.25 (s, 3 H) 3.83 (br. s., 2 H) 4.97 (s, 1 H) 6.13 (br. s., 1 H) 6.29 (s, 1 H) 7.89 (s, 1 H) 8.65 (s, 1 H) 9.13 (s, 1 H) 9.46 (s, 1 H) 11.35 (s, 1 H). ESI-MS m/z [M+H]+ 430.0.

EXAMPLE 47

N-(5-(6-cyano-5-((1-((2-fluoroethyl)(methyl)amino)-1-oxopropan-2-yl)amino)pyridin-3-yl)pyrazin-2-yl)cyclopropanecarboxamide

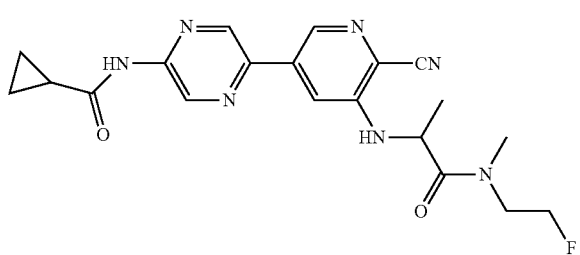 [SMILES: CC(Nc1cc(-c2cnc(NC(=O)C3CC3)cn2)cnc1C#N)C(=O)N(C)CCF]

The title compound was prepared in a manner similar to Example 30, except alanine was used, followed by 2-fluoro-N-methylethanamine, HCl to afford the title compound as a pale yellow solid (9.3 mg, 26.5% yield). 1H NMR (400 MHz, DMSO-d6) δ ppm 0.91 (s, 3 H) 1.36 (s, 2 H) 2.08 (s, 1 H) 2.93 (s, 1 H) 3.22 (s, 2 H) 3.72 (br. s., 2 H) 4.50 (s, 1 H) 4.62 (s, 1 H) 4.92 (s, 1 H) 7.90 (s, 1 H) 8.64 (s, 1 H) 9.14 (s, 1 H) 9.46 (s, 1 H) 11.35 (s, 1 H). ESI-MS m/z [M+H]+ 412.0.

EXAMPLE 48

(R)-N-(5-(6-cyano-5-((2-oxo-2-(2-(trifluoromethyl)pyrrolidin-1-yl)ethyl)amino)pyridin-3-yl)pyrazin-2-yl)cyclopropanecarboxamide

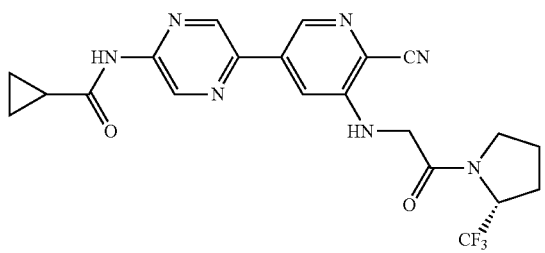 [SMILES: N#Cc1ncc(-c2cnc(NC(=O)C3CC3)cn2)cc1NCC(=O)N1CCC[C@@H]1C(F)(F)F]

The title compound was prepared in a manner similar to Example 30, except glycine was used, followed by (R)-2-(trifluoromethyl)pyrrolidine to afford the title compound as a pale yellow solid (14.9 mg, 68.6% yield). 1H NMR (400 MHz, DMSO-d6) δ ppm 0.91 (s, 3 H) 2.06 (br. s., 4 H) 3.68 (br. s., 2 H) 4.09-4.30 (m, 1 H) 4.33 (br. s., 1 H) 4.80 (s, 1 H) 6.51 (br. s., 1 H) 7.76 (s, 1 H) 8.64 (s, 1 H) 9.09 (s, 1 H) 9.44 (s, 1 H) 11.34 (s, 1 H). ESI-MS m/z [M+H]+ 460.0.

EXAMPLE 49

N-(5-(6-cyano-5-((2-((cyanomethyl)(methyl)amino)-2-oxoethyl)amino)pyridin-3-yl)pyrazin-2-yl)cyclopropanecarboxamide

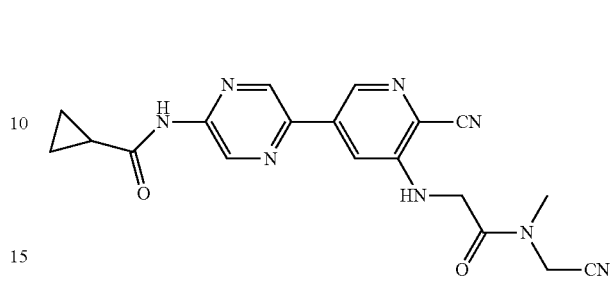

The title compound was prepared in a manner similar to Example 30, except glycine was used, followed by 2-(methylamino)acetonitrile to afford the title compound as a yellow solid (10.1 mg, 58.4% yield). 1H NMR (400 MHz, DMSO-d6) δ ppm 0.89 (s, 4 H) 2.06 (s, 1 H) 3.17 (s, 2 H) 4.33 (br. s., 2 H) 4.47 (s, 1 H) 6.42 (s, 1 H) 7.81 (s, 1 H) 8.65 (s, 1 H) 9.12 (s, 1 H) 9.45 (s, 1 H) 11.34 (s, 1 H). ESI-MS m/z [M+H]+ 391.0.

EXAMPLE 50

(S)-N-(5-(6-cyano-5-((1-((cyanomethyl)(methyl)amino)-1-oxopropan-2-yl)amino)pyridin-3-yl)pyrazin-2-yl)cyclopropanecarboxamide

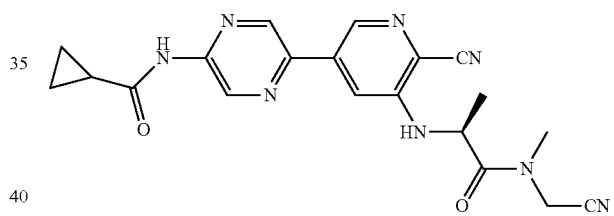

The title compound was prepared in a manner similar to Example 30, except (S)-2-aminopropanoic acid was used, followed by 2-(methylamino)acetonitrile to afford the title compound as a pale yellow solid (12.3 mg, 71.4% yield). 1H NMR (400 MHz, DMSO-d6) δ ppm 0.90 (s, 4 H) 1.40 (s, 3 H) 2.08 (s, 1 H) 3.25 (s, 2 H) 4.47 (s, 2 H) 4.97 (s, 1 H) 6.31 (s, 1 H) 7.90 (s, 1 H) 8.67 (s, 1 H) 9.12 (s, 1 H) 9.46 (s, 1 H) 11.35 (s, 1 H). ESI-MS m/z [M+H]+ 405.0.

EXAMPLE 51

(S)-N-(5-(6-cyano-5-((1-((cyanomethyl)(methyl)amino)-1-oxobutan-2-yl)amino)pyridin-3-yl)pyrazin-2-yl)cyclopropanecarboxamide

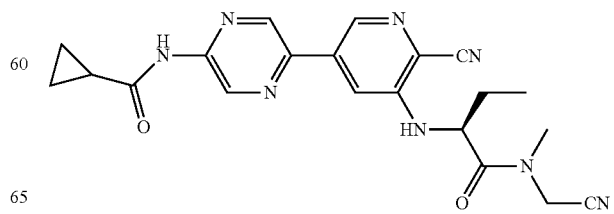

The title compound was prepared in a manner similar to Example 30, except (S)-2-aminobutanoic acid was used, followed by 2-(methylamino)acetonitrile to afford the title compound as a pale yellow solid (9.4 mg, 54.9% yield). 1H NMR (400 MHz, DMSO-d6) δ ppm 0.90 (s, 7 H) 1.79 (s, 1 H) 1.86 (br. s., 1 H) 2.06 (s, 1 H) 3.26 (s, 3 H) 4.47 (s, 2 H) 4.96 (br. s., 1 H) 6.20 (s, 1 H) 7.95 (s, 1 H) 8.66 (s, 1 H) 9.12 (s, 1 H) 9.46 (s, 1 H) 11.35 (s, 1 H). ESI-MS m/z [M+H]+ 419.0.

EXAMPLE 52

(S)-N-(5-(6-cyano-5-((1-((2-hydroxyethyl)(methyl)amino)-4-methoxy-1-oxobutan-2-yl)amino)pyridin-3-yl)pyrazin-2-yl)cyclopropanecarboxamide

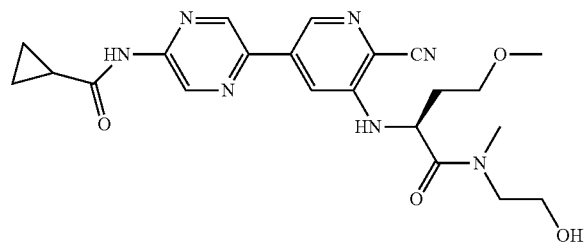 [SMILES: COCC[C@H](Nc1cc(-c2cnc(NC(=O)C3CC3)cn2)cnc1C#N)C(=O)N(C)CCO]

The title compound was prepared in a manner similar to Example 30, except (S)-2-amino-4-methoxybutanoic acid was used, followed by 2-(methylamino)ethanol to afford the title compound as a yellowish-orange film (2 mg, 14.94% yield). 1H NMR (400 MHz, methanol-d4) δ ppm 0.91-1.00 (m, 2 H) 1.02-1.10 (m, 2 H) 1.26-1.42 (m, 1 H) 1.90-2.06 (m, 2 H) 2.17-2.32 (m, 1 H) 2.95-3.03 (m, 2 H) 3.36-3.42 (m, 4 H) 3.51-4.01 (m, 6 H) 4.94-5.20 (m, 1 H) 7.80-8.06 (m, 1 H) 8.60 (dd, J=5.81, 1.52 Hz, 1 H) 8.94 (dd, J=9.60, 1.52 Hz, 1 H) 9.48-9.49 (m, 1 H). ESI-MS m/z [M+H]+ 454.0.

EXAMPLE 53

(S)-N-(5-(6-cyano-5-((1-((2,2-difluoroethyl)(methyl)amino)-1-oxopropan-2-yl)amino)pyridin-3-yl)pyrazin-2-yl)cyclopropanecarboxamide

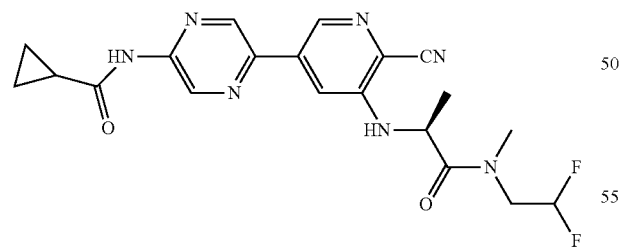

The title compound was prepared in a manner similar to Example 30, except (S)-2-aminopropanoic acid was used, followed by 2,2-difluoro-N-methylethanamine, HCl to afford the title compound as a pale yellow solid (11.2 mg, 61.3% yield). 1H NMR (400 MHz, DMSO-d6) δ ppm 0.91 (s, 3 H) 1.38 (s, 3 H) 2.08 (s, 1 H) 2.97 (s, 1 H) 3.25 (s, 3 H) 3.77-3.89 (m, 1 H) 4.92 (br. s., 1 H) 6.14 (s, 1 H) 6.29 (s, 1 H) 7.89 (s, 1 H) 8.66 (s, 1 H) 9.13 (s, 1 H) 9.46 (s, 1 H) 11.35 (s, 1 H). ESI-MS m/z [M+H]+ 430.0.

EXAMPLE 54

(S)-N-(5-(6-cyano-5-((1-((2-fluoroethyl)(methyl)amino)-1-oxopropan-2-yl)amino)pyridin-3-yl)pyrazin-2-yl)cyclopropanecarboxamide

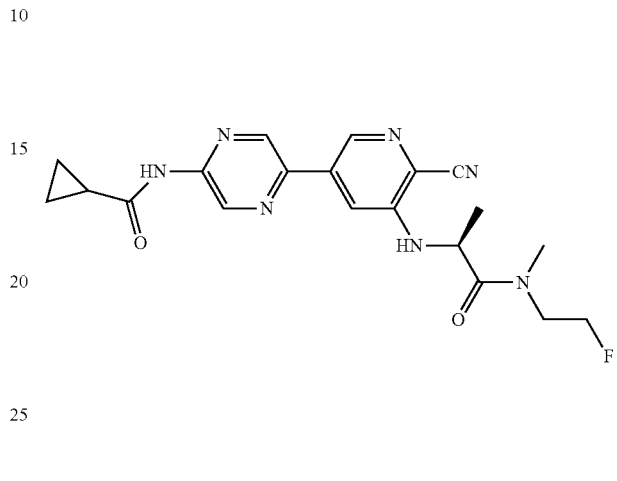

The title compound was prepared in a manner similar to Example 30, except (S)-2-aminopropanoic acid was used, followed by 2-fluoro-N-methylethanamine, HCl to afford the title compound as a pale yellow solid (8.5 mg, 48.5% yield). 1H NMR (400 MHz, DMSO-d6) δ ppm 0.91 (s, 3 H) 1.36 (s, 2 H) 2.08 (s, 1 H) 2.93 (s, 1 H) 3.22 (s, 2 H) 3.72 (br. s., 1 H) 4.62 (s, 2 H) 4.91 (br. s., 1 H) 6.26 (s, 1 H) 7.90 (s, 1 H) 8.65 (s, 1 H) 9.14 (s, 1 H) 9.46 (s, 1 H) 11.35 (s, 1 H). ESI-MS m/z [M+H]+ 412.0.

EXAMPLE 55

N-(5-(6-cyano-5-(((S)-1-((R)-2-cyanopyrrolidin-1-yl)-1-oxopropan-2-yl)amino)pyridin-3-yl)pyrazin-2-yl)cyclopropanecarboxamide

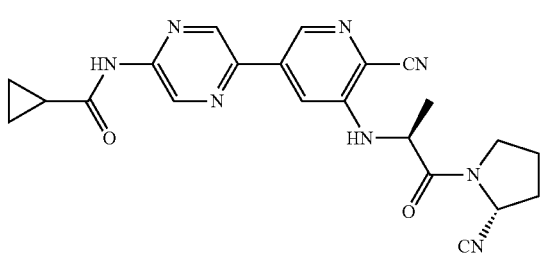

The title compound was prepared in a manner similar to Example 30, except (S)-2-aminopropanoic acid was used, followed by (R)-pyrrolidine-2-carbonitrile to afford the title compound as a pale yellow solid (2.6 mg, 14.19% yield). 1H NMR (400 MHz, methanol-d4) δ ppm 0.84 (br. s., 2 H) 0.93 (br. s., 2 H) 1.42 (s, 3 H) 1.84 (s, 2 H) 2.19 (br. s., 3 H) 3.97 (br. s., 1 H) 4.59 (s, 1 H) 4.67 (s, 1 H) 7.70 (s, 1 H) 8.52 (s, 1 H) 8.84 (s, 1 H) 9.38 (s, 1 H). ESI-MS m/z [M+H]+ 431.0.

EXAMPLE 56

(S)-N-(5-(6-cyano-5-((1-((2-fluoroethyl)(methyl)amino)-1-oxobutan-2-yl)amino)pyridin-3-yl)pyrazin-2-yl)cyclopropanecarboxamide

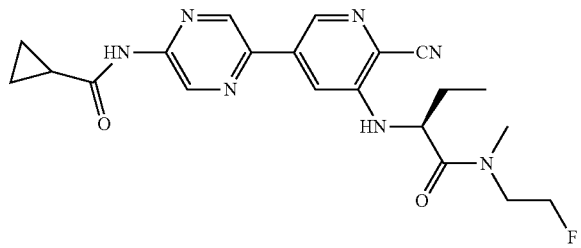 [SMILES: CC[C@H](Nc1cc(-c2cnc(NC(=O)C3CC3)cn2)cnc1C#N)C(=O)N(C)CCF]

The title compound was prepared in a manner similar to Example 30, except (S)-2-aminobutanoic acid was used, followed by 2-fluoro-N-methylethanamine, HCl to afford the title compound as a pale yellow film (8 mg, 45.9% yield). 1H NMR (400 MHz, methanol-d4) δ ppm 0.84 (s, 2 H) 0.94 (s, 6 H) 1.78 (s, 1 H) 1.81-2.03 (m, 3 H) 2.92 (s, 1 H) 3.24 (s, 3 H) 3.64 (s, 1 H) 4.40 (s, 1 H) 4.52 (s, 1 H) 7.76 (s, 1 H) 8.48 (s, 1 H) 8.83 (s, 1 H) 9.37 (s, 1 H). ESI-MS m/z [M+H]+ 426.0.

EXAMPLE 57

(S)-N-(5-(6-cyano-5-((1-(dimethylamino)-3-hydroxy-1-oxopropan-2-yl)amino)pyridin-3-yl)pyrazin-2-yl)cyclopropanecarboxamide

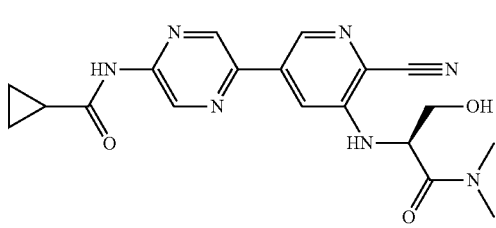 [SMILES: CN(C)C(=O)[C@H](CO)Nc1cc(-c2cnc(NC(=O)C3CC3)cn2)cnc1C#N]

The title compound was prepared in a manner similar to Example 30, except (S)-2-amino-3-hydroxypropanoic acid was used to afford the title compound as a yellow solid (5.6 mg, 11.10% yield). 1H NMR (500 MHz, DMSO-d6) δ ppm 0.90 (s, 4 H) 2.07 (s, 1 H) 2.90 (s, 3 H) 3.16 (s, 3 H) 3.63 (br. s., 1 H) 3.73 (br. s., 1 H) 4.96 (s, 1 H) 5.14 (br. s., 1 H) 6.13 (s, 1 H) 7.99 (s, 1 H) 8.62 (s, 1 H) 9.11 (s, 1 H) 9.45 (s, 1 H) 11.32 (s, 1 H). ESI-MS m/z [M+H]+ 396.0.

EXAMPLE 58

(S)-N-(5-(6-cyano-5-((1-((2,2-difluoroethyl)(methyl)amino)-3-hydroxy-1-oxopropan-2-yl)amino)pyridin-3-yl)pyrazin-2-yl)cyclopropanecarboxamide

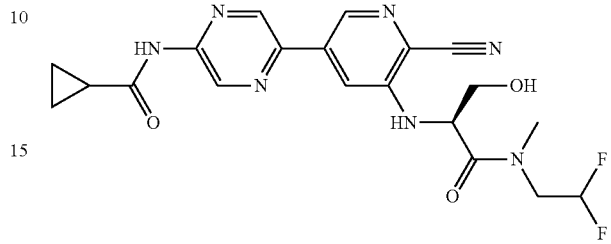

The title compound was prepared in a manner similar to Example 30, except (S)-2-amino-3-hydroxypropanoic acid was used, followed by 2,2-difluoro-N-methylethanamine, HCl to afford the title compound as a brown-orange solid (6.3 mg, 29.1% yield). 1H NMR (500 MHz, DMSO-d6) δ ppm 0.90 (s, 4 H) 2.07 (s, 1 H) 2.96 (s, 1 H) 3.26 (s, 2 H) 3.71 (s, 1 H) 3.80 (br. s., 1 H) 5.03 (br. s., 1 H) 6.13 (s, 1 H) 7.95 (s, 1 H) 8.64 (s, 1 H) 9.11 (s, 1 H) 9.45 (s, 1 H) 11.33 (s, 1 H). ESI-MS m/z [M+H]+ 446.0.

EXAMPLE 59

N-(5-(6-cyano-5-((2-((1-cyanoethyl)amino)-2-oxoethyl)amino)pyridin-3-yl)pyrazin-2-yl)cyclopropanecarboxamide

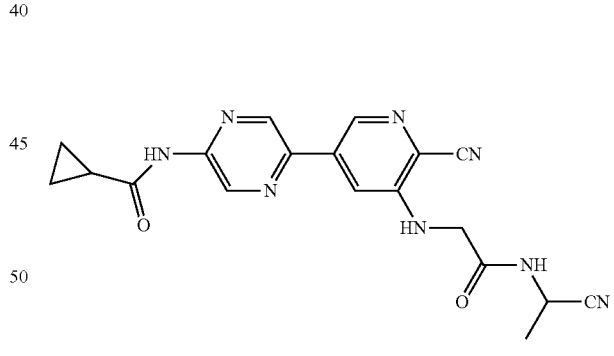

The title compound was prepared in a manner similar to Example 30, except glycine was used, followed by 2-aminopropanenitrile, HCl to afford the title compound as a pale yellow solid (10.6 mg, 40.3% yield). 1H NMR (500 MHz, DMSO-d6) δ ppm 0.89 (s, 3 H) 1.42 (s, 3 H) 2.05 (s, 1 H) 4.04 (br. s., 2 H) 4.82 (s, 1 H) 6.81 (s, 1 H) 7.67 (s, 1 H) 8.64 (s, 1 H) 8.90 (s, 1 H) 9.10 (s, 1 H) 9.42 (s, 1 H) 11.32 (s, 1 H). ESI-MS m/z [M+H]+ 391.0.

EXAMPLE 60

N-(5-(6-cyano-5-((S)-1-oxo-1-((R)-2-(trifluoromethyl)oxazolidin-3-yl)propan-2-ylamino)pyridin-3-yl)pyrazin-2-yl)cyclopropanecarboxamide

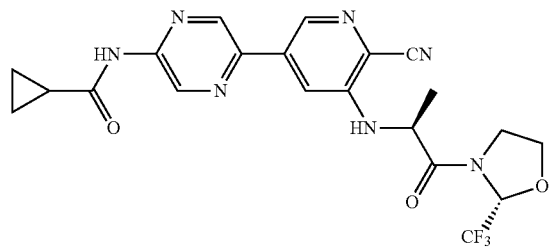 [SMILES: C[C@H](Nc1cc(-c2cnc(NC(=O)C3CC3)cn2)cnc1C#N)C(=O)N1CCO[C@@H]1C(F)(F)F]

The title compound was prepared in a manner similar to Example 30, except (S)-2-aminopropanoic was used, followed by 2-(trifluoromethyl)oxazolidine to afford the title compound as a yellow film (3 mg, 10% yield). 1H NMR (500 MHz, methanol-d4) δ ppm 0.97 (s, 2 H) 1.06 (br. s., 2 H) 1.31 (s, 3 H) 1.59 (s, 2 H) 1.96 (s, 2 H) 3.97 (br. s., 1 H) 4.14 (br. s., 1 H) 4.31 (br. s., 1 H) 4.36 (br. s., 1 H) 4.74 (s, 1 H) 5.90 (br. s., 1 H) 7.85 (s, 1 H) 8.66 (s, 1 H) 8.93 (br. s., 1 H) 9.49 (br. s., 1 H). ESI-MS m/z [M+H]+ 476.0.

EXAMPLE 61

N-(5-(6-cyano-5-((S)-1-oxo-1-((S)-2-(trifluoromethyl)oxazolidin-3-yl)propan-2-ylamino)pyridin-3-yl)pyrazin-2-yl)cyclopropanecarboxamide

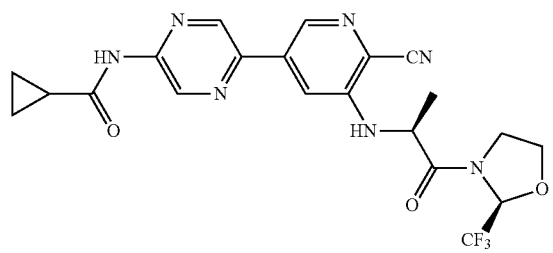 [SMILES: C[C@H](Nc1cc(-c2cnc(NC(=O)C3CC3)cn2)cnc1C#N)C(=O)N1CCO[C@H]1C(F)(F)F]

The title compound was prepared in a manner similar to Example 30, except (S)-2-aminopropanoic was used, followed by 2-(trifluoromethyl)oxazolidine to afford the title compound as a yellow film (2.3 mg, 7.67% yield). 1H NMR (500 MHz, methanol-d4) δ ppm 0.97 (s, 2 H) 1.06 (br. s., 1 H) 1.28 (s, 4 H) 1.52 (s, 1 H) 1.60 (br. s., 2 H) 1.96 (s, 1 H) 3.81 (br. s., 1 H) 4.30 (br. s., 1 H) 4.39 (br. s., 1 H) 4.83 (s, 1 H) 5.96 (br. s., 1 H) 7.88 (s, 1 H) 8.63 (s, 1 H) 8.97 (br. s., 1 H) 9.50 (s, 1 H). ESI-MS m/z [M+H]+ 476.0.

EXAMPLE 62

N-(5-(6-cyano-5-(((2S)-1-((1-cyanoethyl)amino)-1-oxopropan-2-yl)amino)pyridin-3-yl)pyrazin-2-yl)cyclopropanecarboxamide

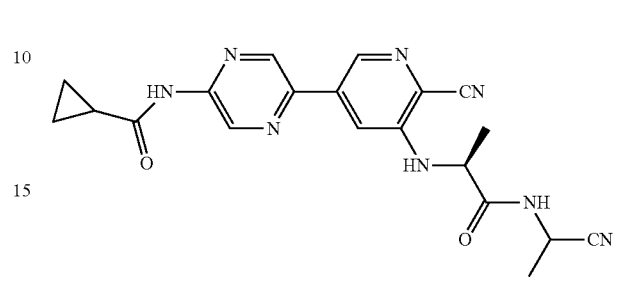

The title compound was prepared in a manner similar to Example 30, except (S)-2-aminopropanoic was used, followed by 2-aminopropanenitrile, HCl to afford the title compound as a yellow solid (11.4 mg, 49.7% yield). 1H NMR (400 MHz, DMSO-d6) δ ppm 0.91 (s, 3 H) 1.38 (s, 2 H) 1.47 (s, 3 H) 2.06 (s, 1 H) 4.31 (s, 1 H) 4.80 (s, 1 H) 6.46 (br. s., 1 H) 7.70 (br. s., 1 H) 8.69 (s, 1 H) 8.96 (s, 1 H) 9.10 (s, 1 H) 9.43 (s, 1 H) 11.36 (s, 1 H). ESI-MS m/z [M+H]+ 405.0.

EXAMPLE 63

N-(5-(6-cyano-5-((2-(3-cyanomorpholino)-2-oxoethyl)amino)pyridin-3-yl)pyrazin-2-yl)cyclopropanecarboxamide

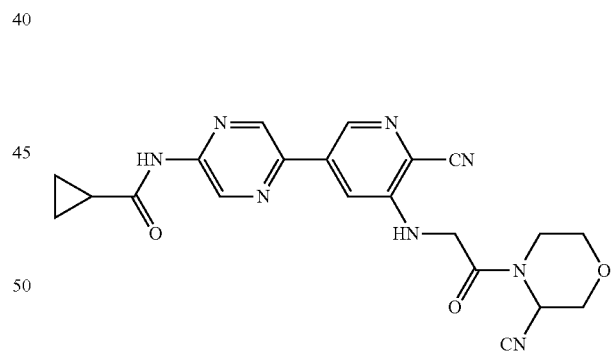

The title compound was prepared in a manner similar to Example 30, except glycine was used, followed by morpholine-3-carbonitrile to afford the title compound as a yellow solid (9.9 mg, 51.6% yield). 1H NMR (400 MHz, DMSO-d6) δ ppm 0.91 (s, 4 H) 2.06 (s, 1 H) 3.36 (br. s., 1 H) 3.61 (br. s., 2 H) 3.97 (br. s., 2 H) 4.06 (d, J=12.38 Hz, 1 H) 4.30 (br. s., 1 H) 4.46 (br. s., 1 H) 5.47 (br. s., 1 H) 6.46 (s, 1 H) 7.81 (s, 1 H) 8.66 (s, 1 H) 9.11 (s, 1 H) 9.45 (s, 1 H) 11.35 (s, 1 H). ESI-MS m/z [M+H]+ 433.0.

EXAMPLE 64

N-(5-(6-cyano-5-((2-oxo-2-(2-(trifluoromethyl)oxazolidin-3-yl)ethyl)amino)pyridin-3-yl)pyrazin-2-yl)cyclopropanecarboxamide

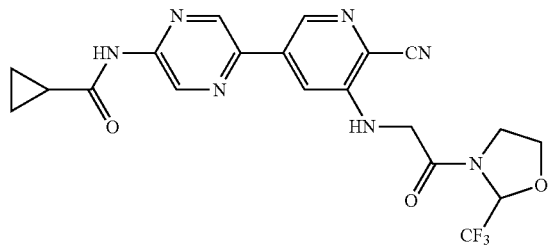 [SMILES: N#Cc1ncc(-c2cnc(NC(=O)C3CC3)cn2)cc1NCC(=O)N1CCOC1C(F)(F)F]

The title compound was prepared in a manner similar to Example 30, except glycine was used, followed by 2-(trifluoromethyl)oxazolidine to afford the title compound as a brown-orange solid (7.7 mg, 28.2% yield). 1H NMR (400 MHz, DMSO-d6) δ ppm 2.07 (s, 1 H) 4.28 (br. s., 4 H) 5.93 (br. s., 1 H) 6.65 (br. s., 1 H) 7.79 (s, 1 H) 8.65 (s, 1 H) 9.08 (s, 1 H) 9.44 (s, 1 H) 11.35 (s, 1 H). ESI-MS m/z [M+H]+ 462.0.

EXAMPLE 65

N-(5-(6-cyano-5-((2-((2-cyanoethyl)(methyl)amino)-2-oxoethyl)amino)pyridin-3-yl)pyrazin-2-yl)cyclopropanecarboxamide

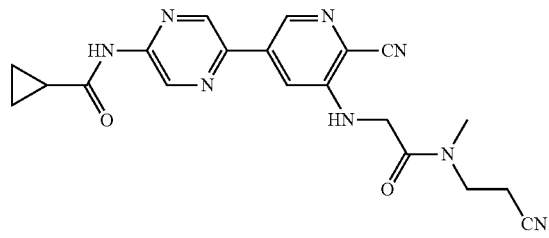 [SMILES: CN(CCC#N)C(=O)CNc1cc(-c2cnc(NC(=O)C3CC3)cn2)cnc1C#N]

The title compound was prepared in a manner similar to Example 30, except glycine was used, followed by 3-(methylamino)propanenitrile to afford the title compound as a yellow solid (9.3 mg, 51.9% yield). 1H NMR (400 MHz, DMSO-d6) δ ppm 0.91 (s, 4 H) 2.09 (s, 1 H) 2.77 (s, 1 H) 2.93 (s, 1 H) 3.15 (d, J=17.43 Hz, 3 H) 3.62 (s, 1 H) 3.73 (s, 1 H) 4.27 (br. s., 2 H) 6.36 (br. s., 1 H) 7.81 (s, 1 H) 8.64 (s, 1 H) 9.13 (s, 1 H) 9.45 (s, 1 H) 11.34 (s, 1 H). ESI-MS m/z [M+H]+ 405.0.

EXAMPLE 66

N-(5-(6-cyano-5-((2-(methyl(2-(methylsulfonyl)ethyl)amino)-2-oxoethyl)amino)pyridin-3-yl)pyrazin-2-yl)cyclopropanecarboxamide

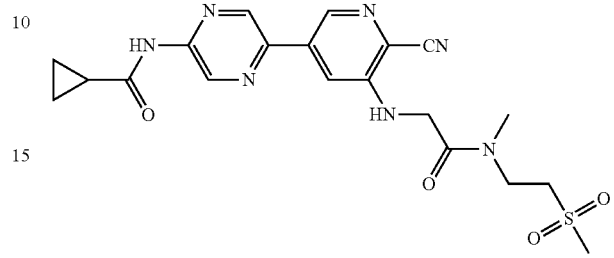

The title compound was prepared in a manner similar to Example 30, except glycine was used, followed by N-methyl-2-(methylsulfonyl)ethanamine to afford the title compound as a yellow solid (12.3 mg, 45.5% yield). 1H NMR (400 MHz, DMSO-d6) δ ppm 0.91 (s, 3 H) 2.91 (s, 1 H) 3.01 (s, 2 H) 3.10 (s, 2 H) 3.39 (br. s., 4 H) 3.75 (s, 1 H) 4.21 (br. s., 1 H) 6.35 (br. s., 1 H) 7.81 (s, 1 H) 8.64 (s, 1 H) 9.13 (s, 1 H) 9.45 (s, 1 H) 11.35 (s, 1 H). ESI-MS m/z [M+H]+ 458.0.

EXAMPLE 67

(S)-N-(5-(6-cyano-5-((1-((2-(dimethylamino)ethyl)(methyl)amino)-1-oxopropan-2-yl)amino)pyridin-3-yl)pyrazin-2-yl)cyclopropanecarboxamide The title compound was prepared in a manner similar to Example 30, except (S)-2-aminopropanoic was used, followed by N1,N1,N2-trimethylethane-1,2-diamine to afford the title compound as a pale yellow film (2.9 mg, 15.61% yield). 1H NMR (400 MHz, methanol-d4) δ ppm 0.97 (s, 2 H) 1.06 (s, 2 H) 1.52 (s, 3 H) 1.96 (s, 1 H) 2.96 (br. s., 6 H) 3.30 (s, 3 H) 3.40 (s, 2 H) 3.63 (s, 1 H) 3.99 (s, 1 H) 7.89 (s, 1 H) 8.62 (s, 1 H) 8.99 (s, 1 H) 9.52 (s, 1 H). ESI-MS m/z [M+H]+ 437.0.

EXAMPLE 68

N-(5-(6-cyano-5-((1-(dimethylamino)-4,4-difluoro-1-oxobutan-2-yl)amino)pyridin-3-yl)pyrazin-2-yl)cyclopropanecarboxamide

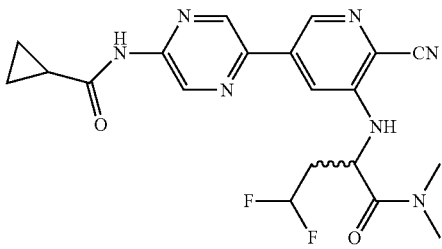 [SMILES: CN(C)C(=O)C(CC(F)F)Nc1cc(-c2cnc(NC(=O)C3CC3)cn2)cnc1C#N]

The title compound was prepared in a manner similar to Example 30, except 2-amino-4,4-difluorobutanoic acid, HCl was used to afford the title compound as a pale yellow film (3.5 mg, 4.25% yield). 1H NMR (400 MHz, methanol-d4) δ ppm 0.94 (br. s., 2 H) 1.04 (br. s., 2 H) 1.25 (s, 1 H) 1.94 (br. s., 1 H) 2.45 (s, 2 H) 2.99 (s, 3 H) 3.24 (s, 3 H) 5.03 (s, 1 H) 7.89 (s, 1 H) 8.64 (s, 1 H) 8.94 (br. s., 1 H) 9.48 (br. s., 1 H). ESI-MS m/z [M+H]+ 430.0.

EXAMPLE 69

N-(5-(6-cyano-5-(((2S)-1-((1-cyanoethyl)(methyl)amino)-1-oxopropan-2-yl)amino)pyridin-3-yl)pyrazin-2-yl)cyclopropanecarboxamide

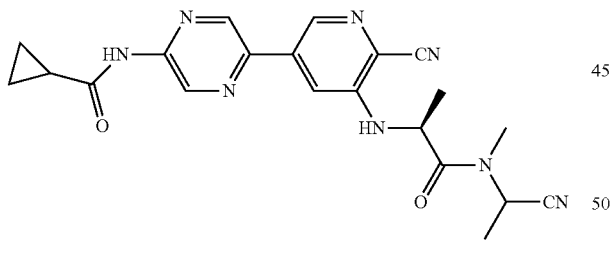

The title compound was prepared in a manner similar to Example 30, except (S)-2-aminopropanoic was used, followed by 2-(methylamino)propanenitrile to afford the title compound as a brown-orange film (5.6 mg, 31.4% yield). 1H NMR (400 MHz, DMSO-d6) δ ppm 0.89 (s, 4 H) 1.40 (s, 3 H) 1.46 (s, 3 H) 2.06 (s, 1 H) 3.20 (s, 3 H) 4.89 (s, 1 H) 5.56 (s, 1 H) 6.38 (br. s., 1 H) 7.84 (s, 1 H) 8.67 (s, 1 H) 9.13 (s, 1 H) 9.45 (s, 1 H) 11.35 (s, 1 H). ESI-MS m/z [M+H]+ 419.0.

EXAMPLE 70

(S)-N-(5-(6-cyano-5-((1-((2-hydroxyethyl)(methyl)amino)-1-oxobutan-2-yl)amino)pyridin-3-yl)pyrazin-2-yl)cyclopropanecarboxamide

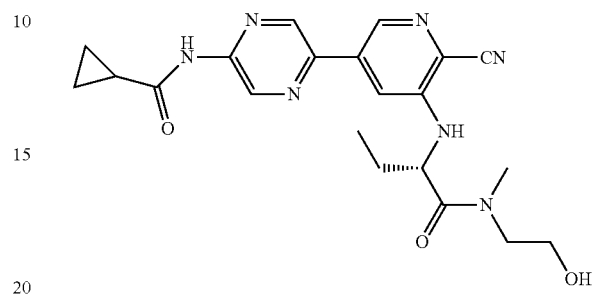

The title compound was prepared in a manner similar to Example 30, except (S)-2-aminobutanoic acid was used, followed by 2-(methylamino)ethanol to afford the title compound as a yellow solid (5.7 mg, 16.44% yield). 1H NMR (400 MHz, DMSO-d6) δ ppm 0.91 (br. s., 9 H) 1.76 (br. s., 1 H) 1.87 (br. s., 1 H) 2.08 (br. s., 1 H) 2.88 (s, 2 H) 3.20 (s, 2 H) 3.34 (br. s., 1 H) 3.59 (br. s., 4 H) 4.91 (br. s., 1 H) 6.17 (br. s., 1 H) 7.96 (br. s., 1 H) 8.62 (br. s., 1 H) 9.11 (s, 1 H) 9.45 (s, 1 H) 11.34 (br. s., 1 H). ESI-MS m/z [M+H]+ 424.0.

EXAMPLE 71

N-(5-(6-cyano-5-((2-(methyl(tetrahydrofuran-3-yl)amino)-2-oxoethyl)amino)pyridin-3-yl)pyrazin-2-yl)cyclopropanecarboxamide

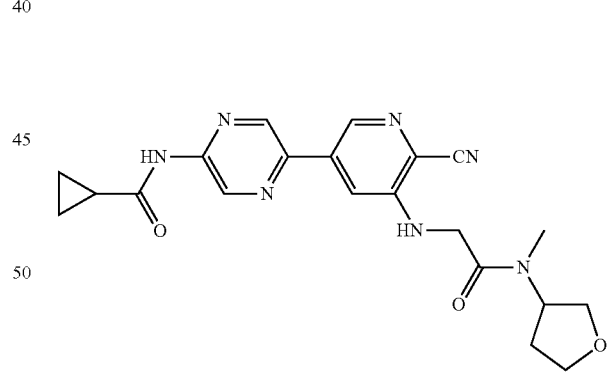

The title compound was prepared in a manner similar to Example 30, except glycine was used, followed by N-methyltetrahydrofuran-3-amine, HCl to afford the title compound as a pale yellow solid (20.1 mg, 60.4% yield). 1H NMR (400 MHz, DMSO-d6) δ ppm 0.89 (s, 3 H) 1.87 (s, 1 H) 2.16 (s, 1 H) 2.82 (s, 1 H) 2.97 (s, 2 H) 3.69 (br. s., 5 H) 3.97 (br. s., 1 H) 4.20 (br. s., 1 H) 4.31 (br. s., 1 H) 5.12 (br. s., 1 H) 6.35 (br. s., 1 H) 7.83 (s, 1 H) 8.65 (s, 1 H) 9.14 (s, 1 H) 9.45 (s, 1 H) 11.35 (s, 1 H). ESI-MS m/z [M+H]+ 422.0.

EXAMPLE 72

N-(5-(6-cyano-5-((2-((2,2-difluoroethyl)(2-hydroxy-ethyl)amino)-2-oxoethyl)amino)pyridin-3-yl)pyrazin-2-yl)cyclopropanecarboxamide

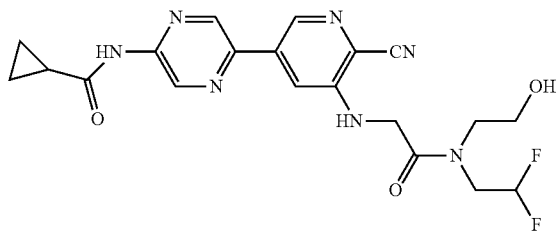 [SMILES: N#Cc1ncc(-c2cnc(NC(=O)C3CC3)cn2)cc1NCC(=O)N(CCO)CC(F)F]

The title compound was prepared in a manner similar to Example 30, except glycine was used, followed by 2-((2,2-difluoroethyl)amino)ethanol to afford the title compound as a pale yellow solid (20.2 mg, 25.6% yield). 1H NMR (500 MHz, DMSO-d6) δ ppm 0.90 (s, 4 H) 2.08 (br. s., 1 H) 3.54 (br. s., 2 H) 3.64 (s, 1 H) 3.78 (br. s., 2 H) 3.96 (s, 1 H) 4.38 (br. s., 2 H) 6.45 (br. s., 1 H) 7.76 (s, 1 H) 8.62 (s, 1 H) 9.08 (s, 1 H) 9.44 (s, 1 H) 11.33 (br. s., 1 H). ESI-MS m/z [M+H]+ 446.0.

EXAMPLE 73

(S)-N-(5-(6-cyano-5-((1-((cyclopropylmethyl)(methyl)amino)-1-oxopropan-2-yl)amino)pyridin-3-yl)pyrazin-2-yl)cyclopropanecarboxamide

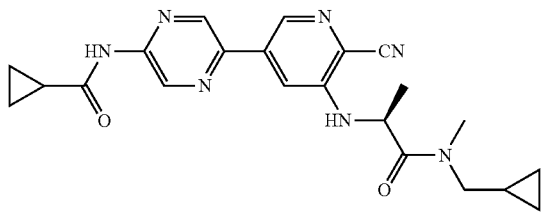 [SMILES: C[C@H](Nc1cc(-c2cnc(NC(=O)C3CC3)cn2)cnc1C#N)C(=O)N(C)CC1CC1]

The title compound was prepared in a manner similar to Example 30, except (S)-2-aminopropanoic was used, followed by 1-cyclopropyl-N-methylmethanamine, HCl to afford the title compound as a pale yellow solid (13.1 mg, 36.7% yield). 1H NMR (500 MHz, DMSO-d6) δ ppm 0.24 (br. s., 1 H) 0.34 (br. s., 1 H) 0.43 (br. s., 1 H) 0.57 (br. s., 1 H) 0.94 (s, 4 H) 1.39 (s, 3 H) 2.10 (s, 1 H) 2.99 (s, 1 H) 3.22 (d, J=14.64 Hz, 3 H) 3.47 (s, 1 H) 4.92 (br. s., 1 H) 6.30 (br. s., 1 H) 7.93 (s, 1 H) 8.68 (s, 1 H) 9.17 (s, 1 H) 9.48 (s, 1 H) 11.38 (s, 1 H). ESI-MS m/z [M+H]+ 420.0.

EXAMPLE 74

(S)-N-(5-(6-cyano-5-((1-(methyl(pyridin-3-yl)amino)-1-oxopropan-2-yl)amino)pyridin-3-yl)pyrazin-2-yl)cyclopropanecarboxamide

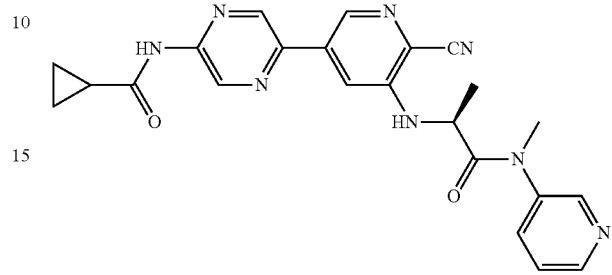

The title compound was prepared in a manner similar to Example 30, except (S)-2-aminopropanoic was used, followed by N-methylpyridin-3-amine to afford the title compound as a yellow film (3.2 mg, 6.37% yield). 1H NMR (400 MHz, methanol-d4) δ ppm 1.28 (s, 1 H) 1.59 (s, 3 H) 3.97 (s, 3 H) 4.47 (d, J=7.07 Hz, 1 H) 7.81 (s, 1 H) 8.58 (br. s., 2 H) 8.86 (br. s., 1 H) 8.92 (br. s., 2 H) 9.46 (br. s., 1 H) 9.51 (br. s., 1 H). ESI-MS m/z [M+H]+ 443.0.

EXAMPLE 75

(R)-N-(5-(6-cyano-5-((2-(3-(fluoromethyl)morpholino)-2-oxoethyl)amino)pyridin-3-yl)pyrazin-2-yl)cyclopropanecarboxamide

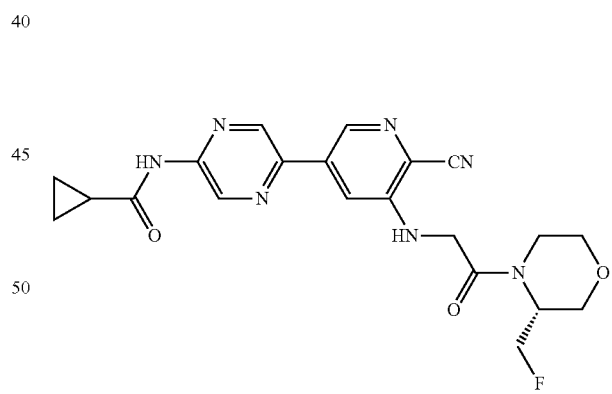

The title compound was prepared in a manner similar to Example 30, except glycine was used, followed by (R)-3-(fluoromethyl)morpholine, HCl to afford the title compound as a pale yellow solid (26.5 mg, 51.9% yield). 1H NMR (400 MHz, DMSO-d6) δ ppm 0.91 (s, 4 H) 2.08 (s, 1 H) 3.59 (s, 1 H) 3.70 (br. s., 2 H) 3.83 (br. s., 1 H) 3.98 (br. s., 2 H) 4.30 (br. s., 2 H) 4.79-5.17 (m, 1 H) 6.45 (s, 1 H) 7.79 (s, 1 H) 8.65 (s, 1 H) 9.11 (s, 1 H) 9.45 (s, 1 H) 11.35 (s, 1 H). ESI-MS m/z [M+H]+ 440.0.

EXAMPLE 76

N-(5-(6-cyano-5-((2-(methyl(pyrazin-2-ylmethyl)
amino)-2-oxoethyl)amino)pyridin-3-yl)pyrazin-2-yl)
cyclopropanecarboxamide

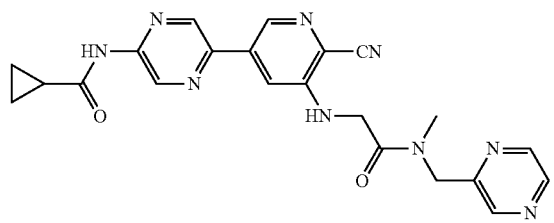 [SMILES: CN(Cc1cnccn1)C(=O)CNc1cc(-c2cnc(NC(=O)C3CC3)cn2)cnc1C#N]

The title compound was prepared in a manner similar to Example 30, except glycine was used, followed by N-methyl-1-(pyrazin-2-yl)methanamine to afford the title compound as a pale yellow solid (36.2 mg, 69% yield). 1H NMR (400 MHz, DMSO-d6) δ ppm 0.91 (br. s., 4 H) 2.07 (br. s., 1 H) 2.87 (s, 1 H) 3.19 (s, 2 H) 4.37 (s, 2 H) 4.72 (s, 1 H) 4.86 (s, 1 H) 7.83 (s, 1 H) 8.54 (s, 1 H) 8.59 (s, 1 H) 8.66 (s, 2 H) 9.05-9.18 (m, 1 H) 9.46 (s, 1 H) 11.35 (s, 1 H). ESI-MS m/z [M+H]+ 444.0.

EXAMPLE 77

N-(5-(6-cyano-5-((2-((2-methoxyethyl)(2,2,2-trifluoroethyl)amino)-2-oxoethyl)amino)pyridin-3-yl)
pyrazin-2-yl)cyclopropanecarboxamide

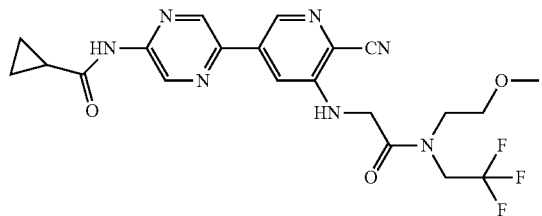 [SMILES: COCCN(CC(F)(F)F)C(=O)CNc1cc(-c2cnc(NC(=O)C3CC3)cn2)cnc1C#N]

The title compound was prepared in a manner similar to Example 30, except glycine was used, followed by 2,2,2-trifluoro-N-(2-methoxyethyl)ethanamine to afford the title compound as a pale beige solid (8.5 mg, 10.04% yield). 1H NMR (400 MHz, DMSO-d6) δ ppm 0.89 (s, 4 H) 2.05 (s, 1 H) 3.16-3.23 (m, 4 H) 3.69 (br. s., 2 H) 4.23 (s, 2 H) 4.41 (br. s., 2 H) 6.60 (s, 1 H) 7.67 (s, 1 H) 8.63 (s, 1 H) 9.06 (s, 1 H) 9.43 (s, 1 H) 11.35 (s, 1 H). ESI-MS m/z [M+H]+ 478.0.

EXAMPLE 78

(R)-N-(5-(6-cyano-5-((1-(dimethylamino)-4,4-difluoro-1-oxobutan-2-yl)amino)pyridin-3-yl)pyrazin-
2-yl)cyclopropanecarboxamide

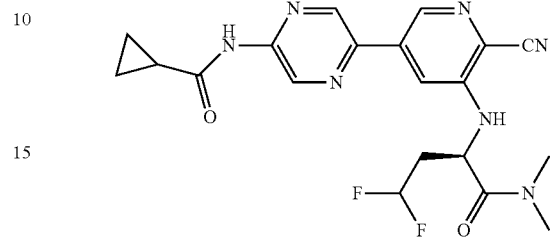

The title compound was prepared in a manner similar to Example 30, except 2-amino-4,4-difluorobutanoic acid, HCl was used. The product was purified by 1D preparative SFC/MS (Waters™ BEH-2EP (19×150 mm)) using a gradient of 10-40% MeOH in liquid CO2, followed by 2D preparative SFC/MS (ChiralPak™ OD-H (20×150 mm)) using an isocratic gradient of 30% MeOH in liquid CO2 to afford the title compound as a yellow solid (6.1 mg, 7.41% yield). 1H NMR (400 MHz, DMSO-d6) δ ppm 0.87 (br. s., 3 H) 1.24 (s, 1 H) 2.04 (br. s., 1 H) 2.33 (br. s., 1 H) 2.40 (br. s., 1 H) 2.88 (s, 3 H) 3.16 (d, J=11.87 Hz, 4 H) 5.02 (br. s., 1 H) 6.51 (s, 1 H) 7.90 (s, 1 H) 8.67 (s, 1 H) 9.09 (s, 1 H) 9.41 (s, 1 H). ESI-MS m/z [M+H]+ 430.0.

EXAMPLE 79

(S)-N-(5-(6-cyano-5-((1-((2,2-difluoroethyl)(2-hydroxyethyl)amino)-1-oxopropan-2-yl)amino)pyridin-
3-yl)pyrazin-2-yl)cyclopropanecarboxamide

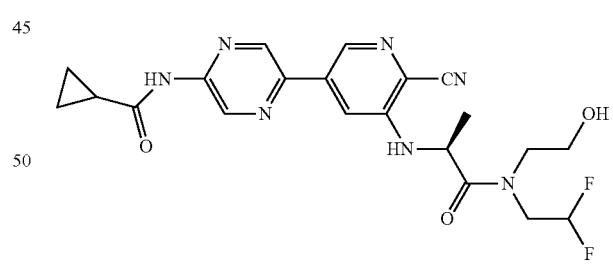

The title compound was prepared in a manner similar to Example 30, except (S)-2-aminopropanoic was used, followed by 2-((2,2-difluoroethyl)amino)ethanol to afford the title compound as a yellowish-orange film (1.4 mg, 1.789% yield). 1H NMR (400 MHz, methanol-d4) δ ppm 0.96 (br. s., 2 H) 1.03 (br. s., 2 H) 1.29 (s, 1 H) 1.37 (s, 1 H) 1.53 (d, J=6.57 Hz, 2 H) 1.93 (s, 2 H) 2.19 (s, 1 H) 2.88 (s, 1 H) 3.48 (t, J=1.64 Hz, 1 H) 4.97 (s, 1 H) 7.96 (s, 1 H) 8.95 (s, 1 H) 9.47 (s, 1 H). ESI-MS m/z [M+H]+ 460.0.

EXAMPLE 80

(S)-N-(5-(6-cyano-5-((1-(dimethylamino)-4,4-difluoro-1-oxobutan-2-yl)amino)pyridin-3-yl)pyrazin-2-yl)cyclopropanecarboxamide

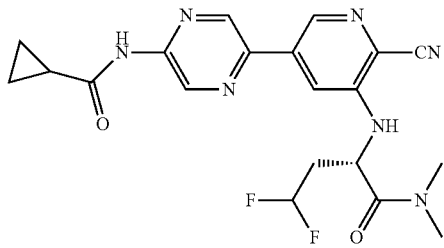 [SMILES: CN(C)C(=O)[C@H](CC(F)F)Nc1cc(-c2cnc(NC(=O)C3CC3)cn2)cnc1C#N]

The title compound was prepared in a manner similar to Example 30, except 2-amino-4,4-difluorobutanoic acid, HCl was used. The product was purified by 1D preparative SFC/MS (Waters™ BEH-2EP (19×150 mm)) using a gradient of 10-40% MeOH in liquid CO2, followed by 2D preparative SFC/MS (ChiralPak™ OD-H (20×150 mm)) using an isocratic gradient of 30% MeOH in liquid CO2 to afford the title compound as a pale yellow film (1.7 mg, 2.066% yield). 1H NMR (400 MHz, methanol-d4) δ ppm 0.85 (br. s., 2 H) 0.94 (br. s., 2 H) 1.19 (s, 1 H) 1.84 (s, 1 H) 2.36 (s, 2 H) 2.89 (s, 2 H) 3.15 (s, 3 H) 4.93 (s, 1 H) 7.80 (s, 1 H) 8.54 (s, 1 H) 9.39 (br. s., 1 H). ESI-MS m/z [M+H]+ 430.0.

EXAMPLE 81

N-(5-(6-cyano-5-(((S)-1-((S)-3-cyanomorpholino)-1-oxopropan-2-yl)amino)pyridin-3-yl)pyrazin-2-yl)cyclopropanecarboxamide

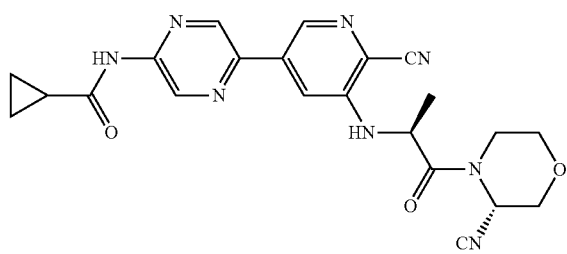

The title compound was prepared in a manner similar to Example 30, except (S)-2-aminopropanoic was used, followed by (S)-morpholine-3-carbonitrile to afford the title compound as a yellow solid (9 mg, 35.5% yield). 1H NMR (400 MHz, DMSO-d6) δ ppm 0.91 (s, 4 H) 1.39 (s, 3 H) 2.09 (s, 1 H) 3.44 (br. s., 1 H) 3.61 (br. s., 1 H) 3.99 (br. s., 1 H) 4.06 (d, J=11.87 Hz, 1 H) 4.22 (br. s., 1 H) 5.00 (br. s., 1 H) 6.47 (s, 1 H) 7.87 (s, 1 H) 8.69 (s, 1 H) 9.13 (s, 1 H) 9.46 (s, 1 H) 11.37 (s, 1 H). ESI-MS m/z [M+H]+ 447.0.

EXAMPLE 82

N-(5-(6-cyano-5-((2-((2,2-difluoroethyl)(2-methoxyethyl)amino)-2-oxoethyl)amino)pyridin-3-yl)pyrazin-2-yl)cyclopropanecarboxamide

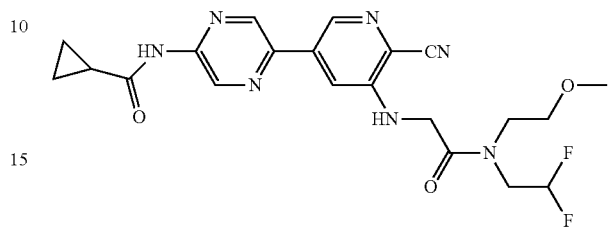

The title compound was prepared in a manner similar to Example 30, except glycine was used, followed by 2,2-difluoro-N-(2-methoxyethyl)ethanamine, HCl to afford the title compound as a pale yellow solid (38.5 mg, 47.2% yield). 1H NMR (400 MHz, DMSO-d6) δ ppm 0.91 (s, 3 H) 2.05 (s, 1 H) 3.23 (s, 1 H) 3.32 (s, 2 H) 3.58 (br. s., 3 H) 3.67 (s, 1 H) 3.79 (br. s., 1 H) 4.36 (br. s., 1 H) 6.41-6.55 (m, 1 H) 7.70-7.78 (m, 1 H) 8.63 (s, 1 H) 9.09 (s, 1 H) 9.44 (s, 1 H) 11.34 (s, 1 H). ESI-MS m/z [M+H]+ 460.0.

EXAMPLE 83

(R)-N-(5-(6-cyano-5-((1-((2,2-difluoroethyl)(methyl)amino)-1-oxopropan-2-yl)amino)pyridin-3-yl)pyrazin-2-yl)cyclopropanecarboxamide

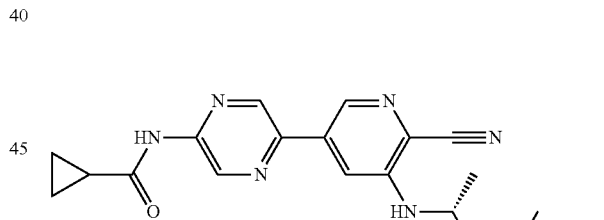

The title compound was prepared in a manner similar to Example 30, except (R)-2-aminopropanoic was used, followed by 2,2-difluoro-N-methylethanamine, HCl to afford the title compound as a pale yellow solid (9.8 mg, 16.15% yield). 1H NMR (400 MHz, DMSO-d6) δ ppm 0.91 (s, 3 H) 1.34 (s, 3 H) 2.97 (s, 1 H) 3.25 (s, 3 H) 3.76-3.95 (m, 2 H) 4.93 (br. s., 1 H) 6.13 (br. s., 1 H) 6.28 (br. s., 1 H) 7.89 (s, 1 H) 8.65 (s, 1 H) 9.13 (s, 1 H) 9.46 (s, 1 H) 11.35 (s, 1 H). ESI-MS m/z [M+H]+ 430.0.

EXAMPLE 84

(S)-N-(5-(6-cyano-5-((2-(3-methylmorpholino)-2-oxoethyl)amino)pyridin-3-yl)pyrazin-2-yl)cyclopropanecarboxamide

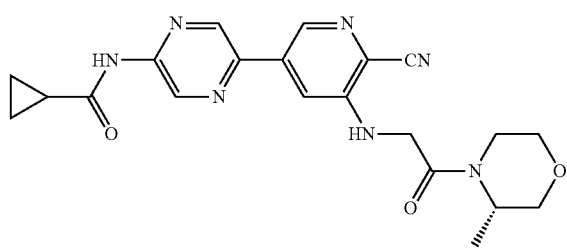 [SMILES: C[C@H]1COCCN1C(=O)CNc1cc(-c2cnc(NC(=O)C3CC3)cn2)cnc1C#N]

The title compound was prepared in a manner similar to Example 30, except glycine was used, followed by (S)-3-methylmorpholine to afford the title compound as a pale yellow solid (12.8 mg, 51.4% yield). 1H NMR (400 MHz, DMSO-d6) δ ppm 0.91 (s, 4 H) 1.18 (br. s., 2 H) 1.34 (br. s., 1 H) 2.06 (s, 1 H) 3.42 (br. s., 1 H) 3.49 (br. s., 3 H) 3.65 (br. s., 2 H) 3.89 (br. s., 1 H) 4.09 (br. s., 2 H) 4.38 (br. s., 1 H) 6.36 (br. s., 1 H) 7.82 (br. s., 1 H) 8.65 (s, 1 H) 9.13 (s, 1 H) 9.45 (s, 1 H) 11.35 (s, 1 H). ESI-MS m/z [M+H]+ 422.0.

EXAMPLE 85

N-(5-(6-cyano-5-((4,4-difluoro-1-((2-fluoroethyl)(methyl)amino)-1-oxobutan-2-yl)amino)pyridin-3-yl)pyrazin-2-yl)cyclopropanecarboxamide

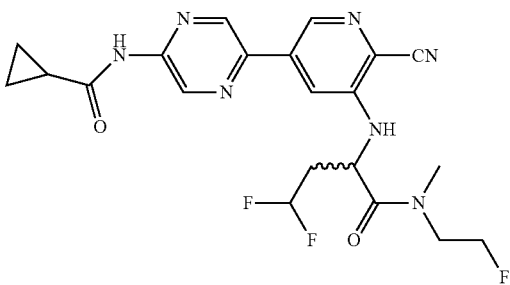 [SMILES: CN(CCF)C(=O)C(CC(F)F)Nc1cc(-c2cnc(NC(=O)C3CC3)cn2)cnc1C#N]

The title compound was prepared in a manner similar to Example 30, except 2-amino-4,4-difluorobutanoic acid, HCl was used, followed by 2-fluoro-N-methylethanamine, HCl to afford the title compound as a pale yellow solid (4.7 mg, 4.82% yield). 1H NMR (400 MHz, DMSO-d6) δ ppm 0.91 (s, 4 H) 2.06 (s, 1 H) 2.41 (br. s., 2 H) 2.91 (s, 1 H) 3.20 (d, J=18.69 Hz, 3 H) 4.46 (br. s., 1 H) 4.59 (d, J=12.38 Hz, 1 H) 5.02 (br. s., 1 H) 6.22 (br. s., 1 H) 6.58 (s, 1 H) 7.88 (s, 1 H) 8.68 (s, 1 H) 9.11 (s, 1 H) 9.45 (s, 1 H) 11.35 (s, 1 H). ESI-MS m/z [M+H]+ 462.0.

EXAMPLE 86

N-(5-(6-cyano-5-(((S)-1-((2,2-difluoroethyl)(methyl)amino)-1-oxopropan-2-yl)amino)pyridin-3-yl)pyrazin-2-yl)-2-methylcyclopropanecarboxamide

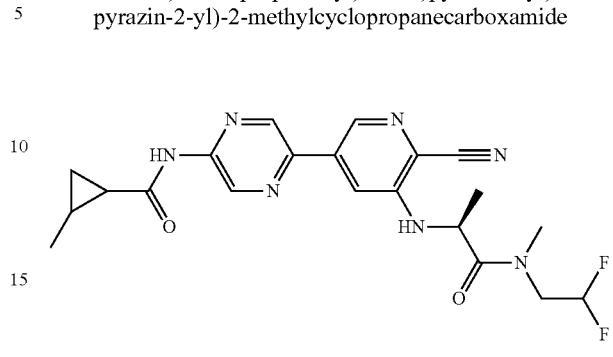

A mixture of N-(5-bromopyrazin-2-yl)-2-methylcyclopropanecarboxamide (200 mg, 0.781 mmol), Pd(dppf)2 CHCl3 adduct (30.4 mg, 0.037 mmol), aqueous cesium carbonate solution (2M, 1488 μl, 2.98 mmol), and 3-fluoro-5-(4,4,5,5-tetramethyl-1,3,2-dioxaborolan-2-yl)picolinonitrile (184 mg, 0.744 mmol) were dissolved in anhydrous dioxane (3719 μl). The reaction was heated at 95° C. for 4 hours. The cooled reaction was diluted into deionized water (30 mL) and a brown solid was collected by vacuum filtration through a Kiriyamarohto SB-60 glass funnel while washing with deionized water followed by hexanes to afford N-(5-(6-cyano-5-fluoropyridin-3-yl)pyrazin-2-yl)-2-methylcyclopropanecarboxamide (268.2 mg, 121% yield). A mixture of potassium carbonate (116 mg, 0.841 mmol), N-(5-(6-cyano-5-fluoropyridin-3-yl)pyrazin-2-yl)-2-methylcyclopropanecarboxamide (50 mg, 0.168 mmol), and (S)-2-aminopropanoic acid (150 mg, 1.682 mmol) were dissolved in anhydrous DMSO (420 μl). The reaction was heated at 120° C. for 2 hours. The cooled reaction was diluted into 1N HCl solution (20 mL) and the brown solid was collected by vacuum filtration through a Kiriyamarohto SB-21 glass funnel while washing with deionized water followed by hexanes to afford (2S)-2-((2-cyano-5-(5-(2-methylcyclopropanecarboxamido)pyrazin-2-yl)pyridin-3-yl)amino)propanoic acid (61.6 mg, crude quantitative yield).

A mixture of (2S)-2-((2-cyano-5-(5-(2-methylcyclopropanecarboxamido)pyrazin-2-yl)pyridin-3-yl)amino)propanoic acid (61.6 mg, 0.168 mmol), 2,2-difluoro-N-methylethanamine, HCl (26.5 mg, 0.202 mmol), and DIPEA (88 μl, 0.504 mmol) were dissolved in anhydrous DMF (336 μl) while under nitrogen. Reaction was stirred for 30 minutes at room temperature, then HATU (77 mg, 0.202 mmol) was added and the mixture was allowed to continue stirring for 24 hours. Doubled volume in DMF and the product was purified by preparative HPLC (Sunfire™ C18, 5 μM, ID TFA) using a gradient of 35-65% ACN (with 0.035% TFA) in water (with 0.05% TFA). The pure fractions were combined and concentrated in vacuo to afford the title compound as a pale yellow solid (13.9 mg, 18.64% yield). 1H NMR (400 MHz, DMSO-d6) δ ppm 0.76 (br. s., 1 H) 1.03-1.17 (m, 5 H) 1.35-1.40 (m, 3 H) 1.83 (s, 1 H) 2.97 (s, 1 H) 3.25 (s, 2 H) 3.80 (t, J=15.41 Hz, 2 H) 4.95 (br. s., 1 H) 6.14 (s, 1 H) 6.28 (br. s., 1 H) 7.88 (s, 1 H) 8.65 (s, 1 H) 9.12 (s, 1 H) 9.44 (s, 1 H) 11.26 (s, 1 H). ESI-MS m/z [M+H]+ 444.0.

EXAMPLE 87

N-(5-(6-cyano-5-((2-((cyanomethyl)(2-hydroxy-ethyl)amino)-2-oxoethyl)amino)pyridin-3-yl)pyrazin-2-yl)cyclopropanecarboxamide

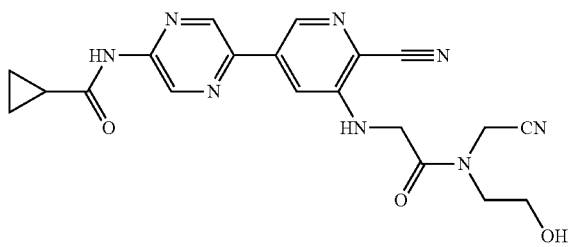 [SMILES: N#CCN(CCO)C(=O)CNc1cc(-c2cnc(NC(=O)C3CC3)cn2)cnc1C#N]

The title compound was prepared in a manner similar to Example 30, except glycine was used, followed by 2-((2-hydroxyethyl)amino)acetonitrile to afford the title compound as a yellow solid (10.5 mg, 21.12% yield). 1H NMR (400 MHz, DMSO-d6) δ ppm 0.91 (s, 4 H) 2.05 (s, 1 H) 3.59 (br. s., 2 H) 3.68 (br. s., 1 H) 4.23-4.49 (m, 4 H) 6.51 (br. s., 1 H) 7.77 (s, 1 H) 8.63 (s, 1 H) 9.08 (s, 1 H) 9.44 (s, 1 H) 11.33 (s, 1 H). ESI-MS m/z [M+H]+ 421.0.

EXAMPLE 88

N-(5-(6-cyano-5-(((S)-1-(((R)-1-cyanoethyl)(methyl)amino)-1-oxopropan-2-yl)amino)pyridin-3-yl)pyrazin-2-yl)cyclopropanecarboxamide

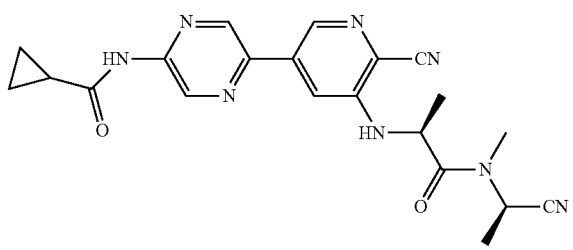 [SMILES: C[C@H](Nc1cc(-c2cnc(NC(=O)C3CC3)cn2)cnc1C#N)C(=O)N(C)[C@H](C)C#N]

The title compound was prepared in a manner similar to Example 30, except (S)-2-aminopropanoic was used, followed by 2-(methylamino)propanenitrile. The product was purified by preparative HPLC (Sunfire™ C18, 5 um, (30×75 mm)) using a gradient of 2-50% ACN (with 0.035% TFA) in water (with 0.05% TFA), followed by 2D preparative SFC/UV (ChiralPak™ IA (20×150 mm)) using an isocratic gradient of 30% IPA in liquid CO2 to afford the title compound as a pale yellow solid (11.1 mg, 10.05% yield). 1H NMR (400 MHz, DMSO-d6) δ ppm 0.91 (s, 4 H) 1.30 (br. s., 3 H) 1.46 (s, 2 H) 2.09 (s, 1 H) 3.20 (s, 2 H) 4.13 (s, 1 H) 4.89 (s, 1 H) 7.84 (s, 1 H) 8.67 (s, 1 H) 9.45 (s, 1 H) 11.35 (s, 1 H). ESI-MS m/z [M+H]+ 419.0.

EXAMPLE 89

N-(5-(6-cyano-5-(((S)-1-(((S)-1-cyanoethyl)(methyl)amino)-1-oxopropan-2-yl)amino)pyridin-3-yl)pyrazin-2-yl)cyclopropanecarboxamide

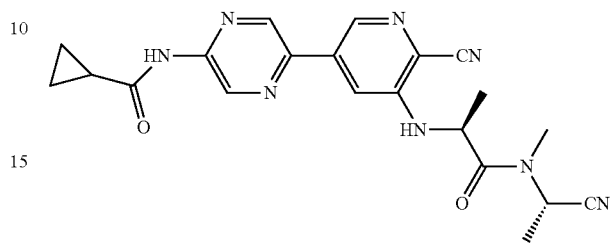

The title compound was prepared in a manner similar to Example 30, except (S)-2-aminopropanoic was used, followed by 2-(methylamino)propanenitrile. The product was purified by preparative HPLC (Waters™ Sunfire™ C18, 5 um, (30×75 mm)) using a gradient of 2-50% ACN (with 0.035% TFA) in water (with 0.05% TFA), followed by 2D preparative SFC/UV (ChiralPak™ IA (20×150 mm)) using an isocratic gradient of 30% IPA in liquid CO2 to afford the title compound as a pale yellow solid (6 mg, 5.43% yield). 1H NMR (400 MHz, DMSO-d6) δ ppm 0.86-0.92 (m, 4 H) 1.24-1.36 (m, 2 H) 1.39 (s, 2 H) 1.47 (s, 2 H) 1.62 (br. s., 1 H) 2.09 (s, 1 H) 3.20 (s, 2 H) 4.13 (s, 1 H) 5.51 (s, 1 H) 6.35 (s, 1 H) 7.71 (s, 1 H) 7.87 (s, 1 H) 8.67 (s, 1 H) 9.13 (s, 1 H) 9.46 (s, 1 H) 11.35 (s, 1 H). ESI-MS m/z [M+H]+ 419.0.

EXAMPLE 90

N-(5-(6-cyano-5-((2-((3-hydroxypropyl)(2,2,2-trifluoroethyl)amino)-2-oxoethyl)amino)pyridin-3-yl)pyrazin-2-yl)cyclopropanecarboxamide

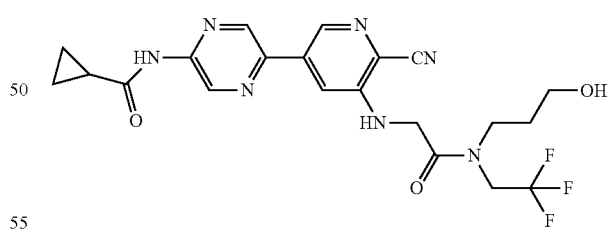

The title compound was prepared in a manner similar to Example 30, except glycine was used, followed by 3-((2,2,2-trifluoroethyl)amino)propan-1-ol to afford the title compound as a pale yellow solid (15.9 mg, 29.3% yield). 1H NMR (400 MHz, DMSO-d6) δ ppm 0.90 (s, 5 H) 1.89 (br. s., 2 H) 2.07 (s, 1 H) 4.17 (s, 2 H) 4.26 (s, 2 H) 6.86 (s, 1 H) 7.80 (s, 1 H) 8.67 (s, 1 H) 9.14 (s, 1 H) 9.44 (s, 1 H) 11.34 (s, 1 H). ESI-MS m/z [M+H]+ 478.0.

EXAMPLE 91

N-(5-(6-cyano-5-(((S)-1-((S)-3-methylmorpholino)-1-oxopropan-2-yl)amino)pyridin-3-yl)pyrazin-2-yl)cyclopropanecarboxamide

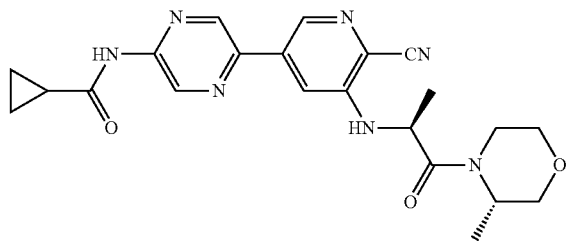 [SMILES: C[C@H](Nc1cc(-c2cnc(NC(=O)C3CC3)cn2)cnc1C#N)C(=O)N1CCOC[C@@H]1C]

The title compound was prepared in a manner similar to Example 30, except (S)-2-aminopropanoic was used, followed by (S)-3-methylmorpholine to afford the title compound as a pale yellow film (8.3 mg, 33.6% yield). 1H NMR (400 MHz, DMSO-d6) δ ppm 0.91 (s, 4 H) 1.16 (s, 1 H) 1.39 (br. s., 3 H) 2.09 (s, 1 H) 3.50 (br. s., 2 H) 3.65 (d, J=11.62 Hz, 1 H) 3.82 (br. s., 2 H) 4.37 (br. s., 1 H) 4.75 (br. s., 1 H) 6.35 (br. s., 1 H) 7.84 (s, 1 H) 8.66 (br. s., 1 H) 9.13 (br. s., 1 H) 9.45 (s, 1 H) 11.36 (s, 1 H). ESI-MS m/z [M+H]+ 436.0.

EXAMPLE 92

N-(5-(6-cyano-5-((2-((1-cyanopropyl)(methyl)amino)-2-oxoethyl)amino)pyridin-3-yl)pyrazin-2-yl)cyclopropanecarboxamide

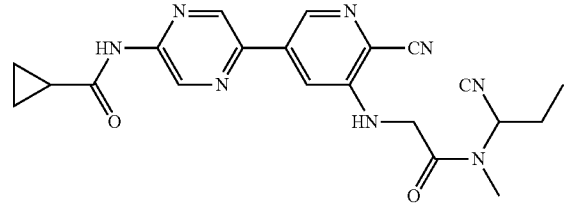

The title compound was prepared in a manner similar to Example 30, except glycine was used, followed by 2-(methylamino)butanenitrile to afford the title compound as a yellow solid (21.4 mg, 49.4% yield). 1H NMR (400 MHz, DMSO-d6) δ ppm 0.91 (s, 6 H) 1.89 (s, 2 H) 2.06 (s, 1 H) 3.10 (s, 3 H) 4.36 (br. s., 2 H) 5.39 (s, 1 H) 6.49 (br. s., 1 H) 7.78 (s, 1 H) 8.65 (s, 1 H) 9.11 (s, 1 H) 9.44 (s, 1 H) 11.34 (s, 1 H). ESI-MS m/z [M+H]+ 419.0.

EXAMPLE 93

(S)-N-(5-(6-cyano-5-((1-((cyanomethyl)(2-hydroxyethyl)amino)-1-oxopropan-2-yl)amino)pyridin-3-yl)pyrazin-2-yl)cyclopropanecarboxamide

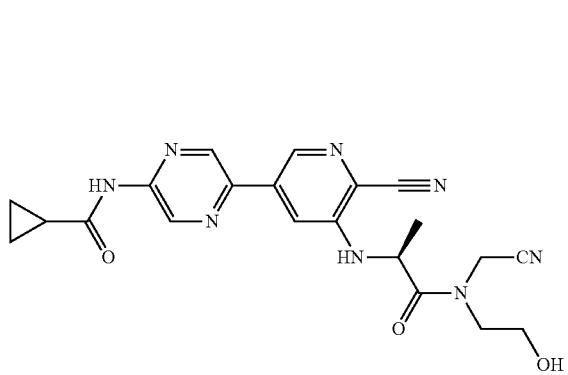 [SMILES: C[C@H](Nc1cc(-c2cnc(NC(=O)C3CC3)cn2)cnc1C#N)C(=O)N(CC#N)CCO]

The title compound was prepared in a manner similar to Example 30, except (S)-2-aminopropanoic was used, followed by 2-((2-hydroxyethyl)amino)acetonitrile to afford the title compound as a yellow solid (13.4 mg, 31.1% yield). 1H NMR (400 MHz, DMSO-d6) δ ppm 1.42 (s, 3 H) 3.56 (br. s., 1 H) 3.68 (br. s., 3 H) 4.43 (s, 2 H) 4.96 (s, 1 H) 6.25 (s, 1 H) 7.92 (s, 1 H) 8.65 (s, 1 H) 9.10 (s, 1 H) 9.45 (s, 1 H) 11.34 (s, 1 H). ESI-MS m/z [M+H]+ 435.0.

EXAMPLE 94

N-(5-(6-cyano-5-((2-oxo-2-(2-(trifluoromethyl)azetidin-1-yl)ethyl)amino)pyridin-3-yl)pyrazin-2-yl)cyclopropanecarboxamide

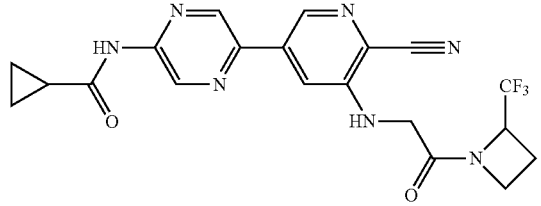 [SMILES: N#Cc1ncc(-c2cnc(NC(=O)C3CC3)cn2)cc1NCC(=O)N1CCC1C(F)(F)F]

The title compound was prepared in a manner similar to Example 30, except glycine was used, followed by 2-(trifluoromethyl)azetidine to afford the title compound as a yellow solid (13.6 mg, 34.4% yield). 1H NMR (400 MHz, DMSO-d6) δ ppm 0.91 (s, 4 H) 2.06 (s, 1 H) 2.29 (br. s., 1 H) 4.21 (d, J=6.57 Hz, 1 H) 4.30 (br. s., 1 H) 4.91 (br. s., 1 H) 6.56 (br. s., 1 H) 7.76 (s, 1 H) 8.64 (s, 1 H) 9.09 (s, 1 H) 9.45 (s, 1 H) 11.35 (s, 1 H). ESI-MS m/z [M+H]+ 446.0.

EXAMPLE 95

(R)-N-(5-(6-cyano-5-((2-oxo-2-(2-(trifluoromethyl)oxazolidin-3-yl)ethyl)amino)pyridin-3-yl)pyrazin-2-yl)cyclopropanecarboxamide

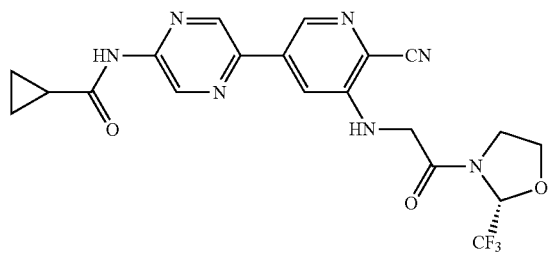 [SMILES: N#Cc1ncc(-c2cnc(NC(=O)C3CC3)cn2)cc1NCC(=O)N1CCO[C@@H]1C(F)(F)F]

The title compound was prepared in a manner similar to Example 30, except glycine was used, followed by 2-(trifluoromethyl)oxazolidine. The product was purified by preparative SFC/MS (ChiralPak™ AS-H C18, 5 um, (20×150 mm)) using an isocratic gradient of 25% IPA (with 0.1% DEA) in liquid CO2 to afford the title compound as a yellow solid (11.9 mg, 12.47% yield). 1H NMR (400 MHz, DMSO-d6) δ ppm 0.88 (s, 3 H) 1.64 (s, 1 H) 2.07 (s, 1 H) 4.14 (s, 2 H) 4.28 (br. s., 1 H) 6.66 (br. s., 1 H) 7.69 (s, 2 H) 7.79 (s, 1 H) 8.64 (s, 1 H) 9.08 (s, 1 H) 9.44 (s, 1 H) 11.35 (s, 1 H). ESI-MS m/z [M+H]+ 462.0.

EXAMPLE 96

(S)-N-(5-(6-cyano-5-((2-oxo-2-(2-(trifluoromethyl)oxazolidin-3-yl)ethyl)amino)pyridin-3-yl)pyrazin-2-yl)cyclopropanecarboxamide

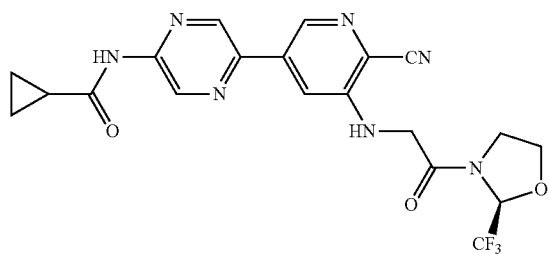 [SMILES: N#Cc1ncc(-c2cnc(NC(=O)C3CC3)cn2)cc1NCC(=O)N1CCO[C@H]1C(F)(F)F]

The title compound was prepared in a manner similar to Example 30, except glycine was used, followed by 2-(trifluoromethyl)oxazolidine. The product was purified by preparative SFC/MS (ChiralPak™ AS-H C18, 5 um, (20×150 mm)) using an isocratic gradient of 25% IPA (with 0.1% DEA) in liquid CO2 to afford the title compound as a yellow solid (12.4 mg, 12.99% yield). 1H NMR (400 MHz, DMSO-d6) δ ppm 0.88 (s, 3 H) 1.36 (s, 1 H) 1.64 (s, 1 H) 2.06 (s, 1 H) 4.11 (s, 3 H) 4.28 (br. s., 1 H) 6.64 (br. s., 1 H) 7.71 (s, 1 H) 7.79 (s, 1 H) 8.65 (s, 1 H) 9.08 (s, 1 H) 9.44 (s, 1 H) 11.35 (s, 1 H). ESI-MS m/z [M+H]+ 462.0.

EXAMPLE 97

N-(5-(6-cyano-5-((2-(4-methylpiperazin-1-yl)-2-oxoethyl)amino)pyridin-3-yl)pyrazin-2-yl)cyclopropanecarboxamide

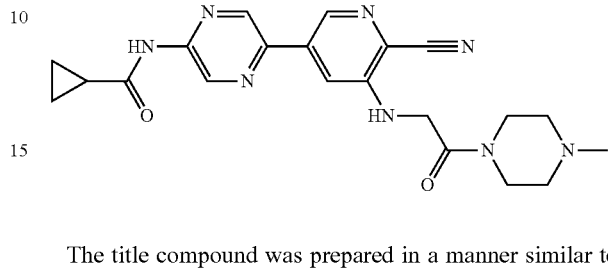

The title compound was prepared in a manner similar to Example 30, except glycine was used, followed by 1-methylpiperazine to afford the title compound as a yellow film (32 mg, 86% yield). 1H NMR (400 MHz, DMSO-d6) δ ppm 0.90 (s, 4 H) 2.10 (s, 1 H) 2.85 (s, 3 H) 3.00 (br. s., 1 H) 3.41 (br. s., 1 H) 3.51 (br. s., 3 H) 4.17 (br. s., 1 H) 4.26 (br. s., 1 H) 4.35 (br. s., 1 H) 4.48 (br. s., 1 H) 6.31 (s, 1 H) 7.85 (s, 1 H) 8.67 (s, 1 H) 9.14 (s, 1 H) 9.46 (s, 1 H) 11.36 (s, 1H). ESI-MS m/z [M+H]+ 421.0.

EXAMPLE 98

N-(5-(6-cyano-5-((2-(4-(2-methoxyethyl)piperazin-1-yl)-2-oxoethyl)amino)pyridin-3-yl)pyrazin-2-yl)cyclopropanecarboxamide

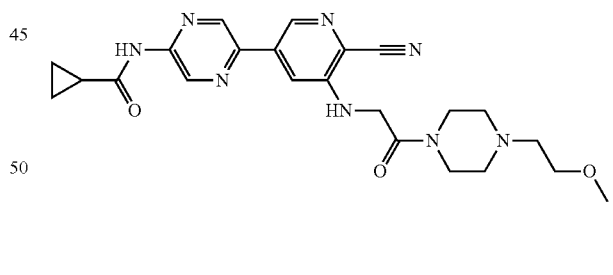

The title compound was prepared in a manner similar to Example 30, except glycine was used, followed by 1-(2-methoxyethyl)piperazine to afford the title compound as a yellow solid (32.7 mg, 79% yield). 1H NMR (400 MHz, DMSO-d6) δ ppm 0.90 (s, 4 H) 2.08 (s, 1 H) 3.16 (br. s., 1 H) 3.34-3.37 (m, 6 H) 3.69 (s, 2 H) 4.16 (br. s., 1 H) 4.27 (br. s., 1 H) 4.36 (br. s., 1 H) 4.42 (br. s., 1 H) 6.31 (s, 1 H) 7.85 (s, 1 H) 8.68 (s, 1 H) 9.14 (s, 1 H) 9.47 (s, 1 H) 11.36 (s, 1H). ESI-MS m/z [M+H]+ 465.0.

EXAMPLE 99

N-(5-(5-((2-(4-acetylpiperazin-1-yl)-2-oxoethyl)amino)-6-cyanopyridin-3-yl)pyrazin-2-yl)cyclopropanecarboxamide

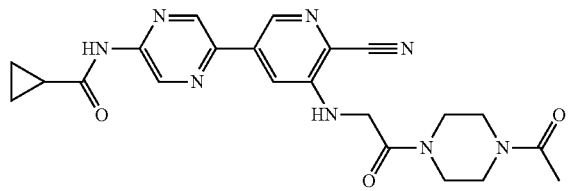 [SMILES: CC(=O)N1CCN(C(=O)CNc2cc(-c3cnc(NC(=O)C4CC4)cn3)cnc2C#N)CC1]

The title compound was prepared in a manner similar to Example 30, except glycine was used, followed by 1-(piperazin-1-yl)ethanone to afford the title compound as a yellow solid (18.9 mg, 47.5% yield). 1H NMR (400 MHz, DMSO-d6) δ ppm 0.91 (s, 4 H) 2.04 (s, 4 H) 3.47 (br. s., 3 H) 3.57 (br. s., 5 H) 3.67 (br. s., 1 H) 4.28 (br. s., 2 H) 6.32 (br. s., 1 H) 7.86 (s, 1 H) 8.65 (s, 1 H) 9.14 (s, 1 H) 9.45 (s, 1 H) 11.35 (s, 1 H). ESI-MS m/z [M+H]+ 449.0.

EXAMPLE 100

N-(5-(6-cyano-5-((2-oxo-2-(2-(trifluoromethyl)morpholino)ethyl)amino)pyridin-3-yl)pyrazin-2-yl)cyclopropanecarboxamide

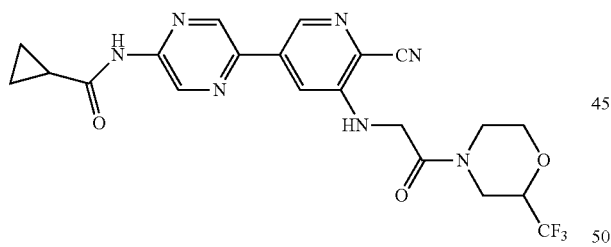

The title compound was prepared in a manner similar to Example 30, except glycine was used, followed by 2-(trifluoromethyl)morpholine, HCl to afford the title compound as a yellow solid (17 mg, 40.3% yield). 1H NMR (400 MHz, DMSO-d6) δ ppm 0.91 (s, 4 H) 2.06 (s, 1 H) 2.96 (br. s., 1 H) 3.35 (br. s., 1 H) 3.94 (br. s., 1 H) 4.04 (br. s., 1 H) 4.24 (br. s., 2 H) 4.39 (br. s., 2 H) 6.35 (br. s., 1 H) 7.84 (s, 1 H) 8.65 (s, 1 H) 9.13 (s, 1 H) 9.46 (s, 1 H) 11.35 (s, 1 H). ESI-MS m/z [M+H]+ 476.0.

EXAMPLE 101

(R)-N-(5-(6-cyano-5-((2-oxo-2-(3-(trifluoromethyl)morpholino)ethyl)amino)pyridin-3-yl)pyrazin-2-yl)cyclopropanecarboxamide

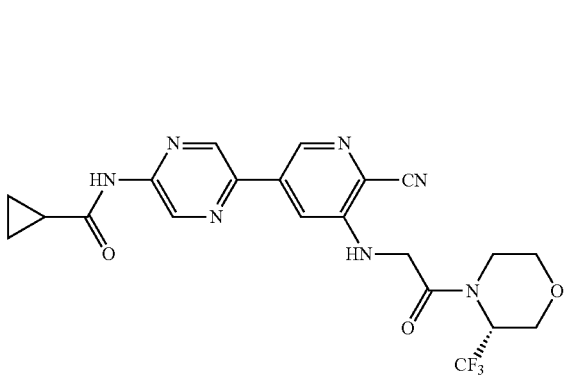 [SMILES: N#Cc1ncc(-c2cnc(NC(=O)C3CC3)cn2)cc1NCC(=O)N1CCOC[C@@H]1C(F)(F)F]

The title compound was prepared in a manner similar to Example 30, except glycine was used, followed by (R)-3-(trifluoromethyl)morpholine to afford the title compound as a brown film (1.5 mg, 3.56% yield). 1H NMR (400 MHz, methanol-d4) δ ppm 0.94 (br. s., 2 H) 1.03 (br. s., 2 H) 1.28 (s, 3 H) 3.62 (s, 1 H) 3.75 (br. s., 2 H) 3.97 (s, 1 H) 4.24 (s, 2 H) 4.45 (s, 1 H) 4.98 (br. s., 2 H) 7.78 (s, 1 H) 8.59 (s, 1 H) 8.93 (s, 1 H) 9.47 (s, 1 H). ESI-MS m/z [M+H]+ 476.0.

EXAMPLE 102

N-(5-(6-cyano-5-((2-(3-cyanopyrrolidin-1-yl)-2-oxoethyl)amino)pyridin-3-yl)pyrazin-2-yl)cyclopropanecarboxamide

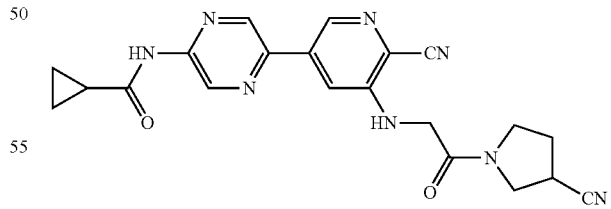

The title compound was prepared in a manner similar to Example 30, except glycine was used, followed by pyrrolidine-3-carbonitrile, HCl to afford the title compound as a yellow solid (2.8 mg, 7.58% yield). 1H NMR (400 MHz, DMSO-d6) δ ppm 1.24 (s, 1 H) 2.06 (s, 1 H) 3.44 (s, 1 H) 3.57 (s, 1 H) 3.67 (s, 1 H) 3.90 (s, 1 H) 4.22 (br. s., 3 H) 6.38 (s, 1 H) 7.81 (s, 1 H) 9.13 (s, 1 H) 11.34 (s, 1 H). ESI-MS m/z [M+H]+ 417.0.

EXAMPLE 103

N-(5-(6-cyano-5-((2-(2-methylmorpholino)-2-oxo-ethyl)amino)pyridin-3-yl)pyrazin-2-yl)cyclopropanecarboxamide

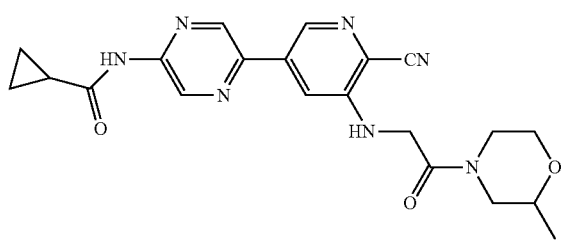 [SMILES: CC1CN(C(=O)CNc2cc(-c3cnc(NC(=O)C4CC4)cn3)cnc2C#N)CCO1]

The title compound was prepared in a manner similar to Example 30, except glycine was used, followed by 2-methylmorpholine to afford the title compound as a yellow solid (13.4 mg, 28.2% yield). 1H NMR (400 MHz, DMSO-d6) δ ppm 0.89 (s, 4 H) 1.11 (s, 1 H) 1.16 (s, 1 H) 2.09 (s, 1 H) 2.83 (s, 1 H) 3.40 (s, 1 H) 3.53 (br. s., 2 H) 3.87 (br. s., 2 H) 4.17 (br. s., 2 H) 4.32 (br. s., 1 H) 6.36 (br. s., 1 H) 7.84 (s, 1 H) 8.65 (s, 1 H) 9.14 (s, 1 H) 9.46 (s, 1 H) 11.35 (s, 1 H). ESI-MS m/z [M+H]+ 422.0.

EXAMPLE 104

N-(5-(6-cyano-5-((2-oxo-2-(2-oxa-6-azaspiro[3.3]heptan-6-yl)ethyl)amino)pyridin-3-yl)pyrazin-2-yl)cyclopropanecarboxamide

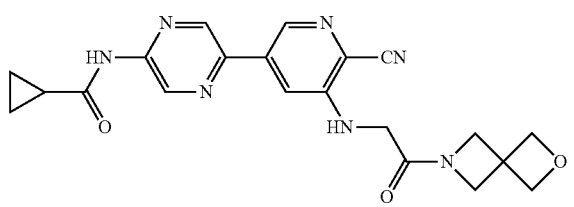 [SMILES: N#Cc1ncc(-c2cnc(NC(=O)C3CC3)cn2)cc1NCC(=O)N1CC2(COC2)C1]

The title compound was prepared in a manner similar to Example 30, except glycine was used, followed by 2-oxa-6-azaspiro[3.3]heptanes to afford the title compound as a yellow film (5.4 mg, 10.89% yield). 1H NMR (400 MHz, DMSO-d6) δ ppm 0.91 (s, 4 H) 2.08 (s, 1 H) 3.51 (br. s., 4 H) 3.76 (d, J=10.36 Hz, 1 H) 3.87-4.04 (m, 2 H) 4.09 (d, J=14.91 Hz, 1 H) 4.55 (s, 1 H) 4.70 (s, 1 H) 6.44 (s, 1 H) 7.75 (s, 1 H) 8.64 (s, 1 H) 9.12 (s, 1 H) 9.46 (s, 1 H) 11.35 (s, 1 H). ESI-MS m/z [M+H]+ 420.0.

EXAMPLE 105

N-(5-(6-cyano-5-((2-(methyl(1-methylazetidin-3-yl)amino)-2-oxoethyl)amino)pyridin-3-yl)pyrazin-2-yl)cyclopropanecarboxamide

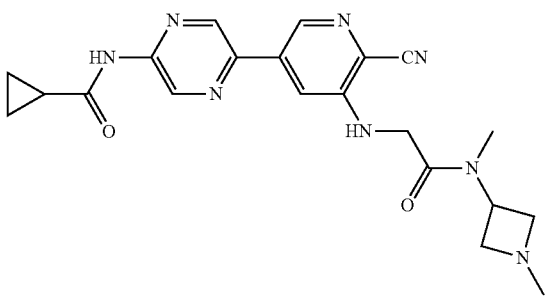 [SMILES: CN1CC(N(C)C(=O)CNc2cc(-c3cnc(NC(=O)C4CC4)cn3)cnc2C#N)C1]

The title compound was prepared in a manner similar to Example 30, except glycine was used, followed by N,1-dimethylazetidin-3-amine, HCl to afford the title compound as a brown/orange solid (18.2 mg, 41.8% yield). 1H NMR (400 MHz, DMSO-d6) δ ppm 0.91 (br. s., 4 H) 2.08 (br. s., 1 H) 2.67 (br. s., 1 H) 2.91 (br. s., 3 H) 3.09 (d, J=14.65 Hz, 2 H) 4.23 (br. s., 1H) 4.29 (br. s., 2 H) 4.48 (br. s., 1 H) 6.34 (br. s., 1 H) 7.83 (br. s., 1 H) 8.65 (s, 1 H) 9.15 (s, 1 H) 9.46 (br. s., 1 H) 11.36 (br. s., 1 H). ESI-MS m/z [M+H]+ 421.0.

EXAMPLE 106

(1S,2S)-N-(5-(6-cyano-5-(((S)-1-(dimethylamino)-1-oxopropan-2-yl)amino)pyridin-3-yl)pyrazin-2-yl)-2-methylcyclopropanecarboxamide

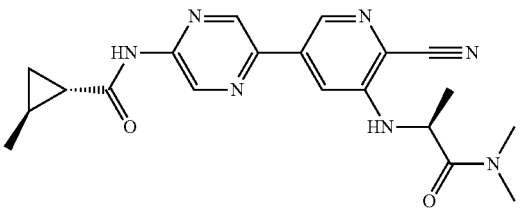

A mixture of 2-methylcyclopropanecarboxylic acid (0.973 mL, 9.99 mmol) and 1-chloro-N,N,2-trimethylprop-1-en-1-amine (1.982 mL, 14.98 mmol) were suspended in anhydrous DCM (100 mL) and stirred at room temperature for 15 minutes. 5-bromopyrazin-2-amine (1.738 g, 9.99 mmol) was then added, followed by DIEA (3.49 mL, 19.98 mmol) and the reaction continued to stir for 2 hours till completion. Diluted in deionized water (50 mL) and extracted with EtOAc (3×25 mL). The organics were combined, washed with brine, dried over magnesium sulfate and dried in vacuo to afford N-(5-bromopyrazin-2-yl)-2-methylcyclopropanecarboxamide (1.953 g, 76% yield).

A mixture of Pd(dppf)2 CHCl3 adduct (30.4 mg, 0.037 mmol), aqueous cesium carbonate solution (2M, 1488 µl, 2.98 mmol), N-(5-bromopyrazin-2-yl)-2-methylcyclopropanecarboxamide (200 mg, 0.781 mmol), and 3-fluoro-5-(4,4,5,5-tetramethyl-1,3,2-dioxaborolan-2-yl)picolinonitrile (184 mg, 0.744 mmol) were dissolved in anhydrous dioxane (3719 µl). The reaction was heated at 95° C. for four hours.

The cooled reaction was diluted into deionized water (30 mL) and the brown solid was collected by vacuum filtration through a Kiriyamarohto SB-60 glass funnel while washing with deionized water followed by hexanes to afford N-(5-(6-cyano-5-fluoropyridin-3-yl)pyrazin-2-yl)-2-methylcyclopropanecarboxamide (268.2 mg, 121% yield).

A mixture of potassium carbonate (349 mg, 2.52 mmol), N-(5-(6-cyano-5-fluoropyridin-3-yl)pyrazin-2-yl)-2-methylcyclopropanecarboxamide (150 mg, 0.505 mmol), and (S)-2-aminopropanoic acid (450 mg, 5.05 mmol) were dissolved in anhydrous DMSO (1261 µl). The reaction was heated at 120° C. for two hours. Diluted in 1N HCl solution (30 mL) and the solid was collected by vacuum filtration through a Kiriyamarohto SB-21 glass funnel while washing with deionized water followed by hexanes to afford (2S)-2-((2-cyano-5-(5-(2-methylcyclopropanecarboxamido)pyrazin-2-yl)pyridin-3-yl)amino)propanoic acid (144 mg, 78% yield).

A mixture of (2S)-2-((2-cyano-5-(5-(2-methylcyclopropanecarboxamido)pyrazin-2-yl)pyridin-3-yl)amino)propanoic acid (144 mg, 0.393 mmol), dimethylamine, HCl (38.5 mg, 0.472 mmol), and DIPEA (205 µl, 1.179 mmol) were dissolved in DMF (786 µl). Reaction was stirred for 30 minutes at room temperature, then HATU (179 mg, 0.472 mmol) was added and the mixture was allowed to continue stirring for 24 hours. Doubled volume in DMF and the product was purified by preparative HPLC (Sunfire™ C18, 5 µM, ID TFA) using a gradient of 35-60% ACN (with 0.035% TFA) in water (with 0.05% TFA) to afford N-(5-(6-cyano-5-(((S)-1-(dimethylamino)-1-oxopropan-2-yl)amino)pyridin-3-yl)pyrazin-2-yl)-2-methylcyclopropanecarboxamide. The product was purified by preparative SFC/MS (ChiralPak™ AD-H C18, 5 uM, (20×150 mm)) using an isocratic gradient of 30% EtOH in liquid CO2 to afford the title compound as a yellow solid (2.6 mg, 1.68% yield). 1H NMR (400 MHz, DMSO-d6) δ ppm 0.86 (br. s., 1 H) 1.05 (s, 1 H) 1.14 (s, 3 H) 1.35 (s, 4 H) 2.09 (s, 1 H) 2.91 (s, 3 H) 3.15 (s, 3 H) 4.91 (s, 1 H) 6.23 (s, 1 H) 7.92 (s, 1 H) 8.63 (s, 1 H) 9.13 (s, 1 H) 9.47 (s, 1 H) 11.25 (s, 1 H). ESI-MS m/z [M+H]+ 394.0.

EXAMPLE 107

(1R,2R)-N-(5-(6-cyano-5-(((S)-1-(dimethylamino)-1-oxopropan-2-yl)amino)pyridin-3-yl)pyrazin-2-yl)-2-methylcyclopropanecarboxamide

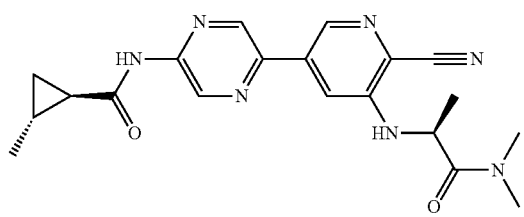

The title compound was prepared in a manner similar to Example 106 to afford the title compound as a yellow solid (1R,2R)-N-(5-(6-cyano-5-(((S)-1-(dimethylamino)-1-oxopropan-2-yl)amino)pyridin-3-yl)pyrazin-2-yl)-2-methylcyclopropanecarboxamide (9.3 mg, 6% yield). 1H NMR (400 MHz, DMSO-d6) δ ppm 0.77 (br. s., 1 H) 1.13 (s, 4 H) 1.35 (s, 3 H) 1.83 (s, 1 H) 2.91 (s, 3 H) 3.14 (s, 3 H) 4.91 (s, 1 H) 6.24 (s, 1 H) 7.93 (s, 1 H) 8.64 (s, 1 H) 9.14 (s, 1 H) 9.45 (s, 1 H) 11.26 (s, 1 H). ESI-MS m/z [M+H]+ 394.0.

EXAMPLE 108

(1R,2S)-N-(5-(6-cyano-5-(((S)-1-(dimethylamino)-1-oxopropan-2-yl)amino)pyridin-3-yl)pyrazin-2-yl)-2-methylcyclopropanecarboxamide

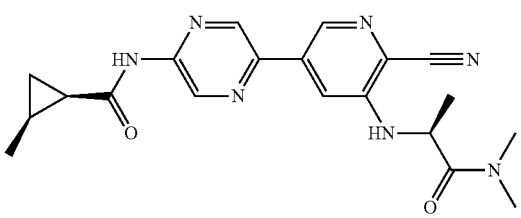

The title compound was prepared in a manner similar to Example 106 to afford the title compound as a yellow solid (4.9 mg, 3.16% yield). 1H NMR (400 MHz, methanol-d4) δ ppm 0.71 (s, 1 H) 1.09 (s, 3 H) 1.16 (s, 2 H) 1.33 (br. s., 1 H) 1.38 (s, 3 H) 1.59 (br. s., 1 H) 2.90 (s, 3 H) 3.14 (s, 3 H) 7.73 (s, 1 H) 8.47 (s, 1 H) 8.84 (s, 1 H) 9.36 (s, 1 H). ESI-MS m/z [M+H]+ 394.0.

EXAMPLE 109

(1S,2R)-N-(5-(6-cyano-5-(((S)-1-(dimethylamino)-1-oxopropan-2-yl)amino)pyridin-3-yl)pyrazin-2-yl)-2-methylcyclopropanecarboxamide

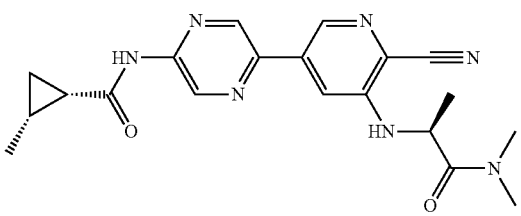

The title compound was prepared in a manner similar to Example 106 to afford the title compound as a yellow solid (1.2 mg, 0.77% yield). 1H NMR (400 MHz, methanol-d4) δ ppm 0.89 (s, 1 H) 0.98 (s, 1 H) 1.10 (s, 3 H) 1.19 (s, 2 H) 1.32 (s, 1 H) 1.38 (s, 3 H) 1.89 (s, 1 H) 2.90 (s, 3 H) 3.14 (s, 3 H) 7.75 (s, 1 H) 8.49 (s, 1 H) 8.85 (s, 1 H) 9.41 (s, 1 H). ESI-MS m/z [M+H]+ 394.0.

EXAMPLE 110

N-(5-(6-cyano-5-((2-((2-hydroxypropyl)(2,2,2-trifluoroethyl)amino)-2-oxoethyl)amino)pyridin-3-yl)pyrazin-2-yl)cyclopropanecarboxamide

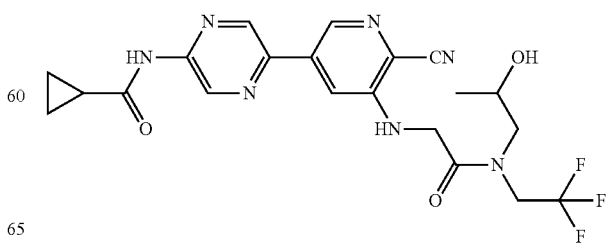

The title compound was prepared in a manner similar to Example 30, except glycine was used, followed by 1-((2,2,2-trifluoroethyl)amino)propan-2-ol to afford the title compound as a yellow solid (8 mg, 16.2% yield). 1H NMR (400 MHz, DMSO-d6) δ ppm 0.89 (s, 4 H) 1.02 (s, 1 H) 1.16 (s, 2 H) 2.08 (br. s., 1 H) 3.49 (br. s., 4 H) 4.10 (s, 1 H) 4.34 (s, 2 H) 4.49 (s, 1 H) 6.58 (br. s., 1 H) 7.71 (s, 1 H) 8.62 (s, 1 H) 9.04 (s, 1 H) 9.44 (s, 1 H) 11.34 (s, 1 H). ESI-MS m/z [M+H]+ 478.0.

EXAMPLE 111

N-(5-(6-cyano-5-((2-((2-hydroxy-2-methylpropyl)(2,2,2-trifluoroethyl)amino)-2-oxoethyl)amino)pyridin-3-yl)pyrazin-2-yl)cyclopropanecarboxamide

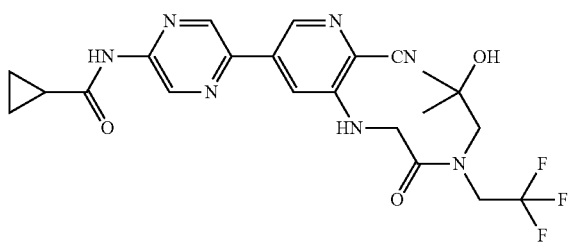 [SMILES: CC(C)(O)CN(CC(F)(F)F)C(=O)CNc1cc(-c2cnc(NC(=O)C3CC3)cn2)cnc1C#N]

The title compound was prepared in a manner similar to Example 30, except glycine was used, followed by 2-methyl-1-((2,2,2-trifluoroethyl)amino)propan-2-ol to afford the title compound as a yellowish-orange solid (12.1 mg, 23.8% yield). 1H NMR (400 MHz, DMSO-d6) δ ppm 0.91 (s, 4 H) 1.04 (s, 3 H) 1.22 (s, 3 H) 3.45-3.51 (m, 2 H) 4.43 (br. s., 3 H) 6.66 (br. s., 1 H) 7.70 (s, 1 H) 8.64 (s, 1 H) 9.05 (s, 1 H) 9.43 (s, 1 H) 11.34 (s, 1 H). ESI-MS m/z [M+H]+ 492.0.

EXAMPLE 112

(S)-N-(5-(6-cyano-5-((1-(ethyl(methyl)amino)-1-oxopropan-2-yl)amino)pyridin-3-yl)pyrazin-2-yl)cyclopropanecarboxamide

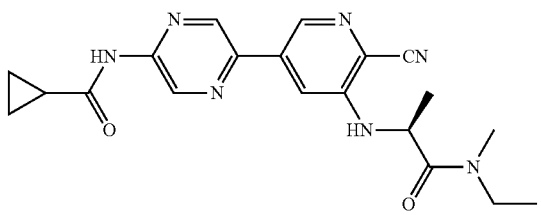 [SMILES: CCN(C)C(=O)[C@H](C)Nc1cc(-c2cnc(NC(=O)C3CC3)cn2)cnc1C#N]

The title compound was prepared in a manner similar to Example 30, except (S)-2-aminopropanoic was used, followed by N-methylethanamine to afford the title compound as a yellow solid (7 mg, 12.54% yield). 1H NMR (400 MHz, DMSO-d6) δ ppm 1.04 (s, 3 H) 1.22 (s, 2 H) 2.08 (s, 1 H) 2.87 (s, 2 H) 3.13 (s, 3 H) 4.85 (s, 1 H) 6.24 (s, 1 H) 8.64 (s, 1 H) 9.15 (s, 1 H) 9.46 (s, 1 H) 11.35 (s, 1 H). ESI-MS m/z [M+H]+ 394.0.

EXAMPLE 113

N-(5-(6-cyano-5-((2-((2S,4R)-4-(hydroxymethyl)-2-(trifluoromethyl)pyrrolidin-1-yl)-2-oxoethyl)amino)pyridin-3-yl)pyrazin-2-yl)cyclopropanecarboxamide

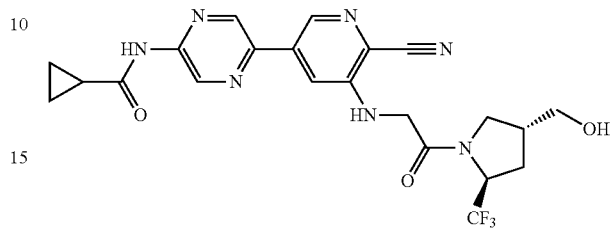

The title compound was prepared in a manner similar to Example 30, except glycine was used, followed by ((3R,5S)-5-(trifluoromethyl)pyrrolidin-3-yl)methanol to afford the title compound as a yellow film (11.7 mg, 20.22% yield). 1H NMR (400 MHz, DMSO-d6) δ ppm 0.92 (s, 4 H) 1.88 (br. s., 1 H) 2.08 (br. s., 2 H) 3.41 (s, 1 H) 3.50 (br. s., 1 H) 3.77 (s, 1 H) 4.27 (br. s., 1 H) 4.83 (s, 1 H) 6.49 (s, 1 H) 7.78 (s, 1 H) 8.66 (s, 1 H) 9.10 (s, 1 H) 9.46 (s, 1 H) 11.36 (s, 1 H). ESI-MS m/z [M+H]+ 490.0.

EXAMPLE 114

(S)-N-(5-(6-cyano-5-((1-((2,2-difluoroethyl)amino)-1-oxopropan-2-yl)amino)pyridin-3-yl)pyrazin-2-yl)cyclopropanecarboxamide

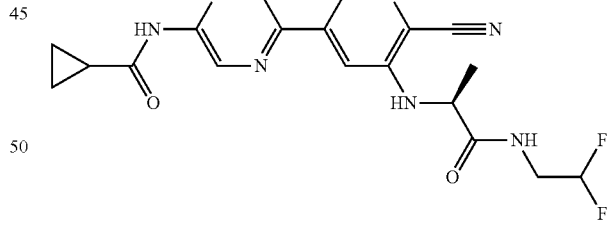

The title compound was prepared in a manner similar to Example 30, except (S)-2-aminopropanoic was used, followed by 2,2-difluoroethanamine to afford the title compound as a pale yellow solid (28 mg, 67.9% yield). 1H NMR (400 MHz, DMSO-d6) δ ppm 0.92 (s, 3 H) 1.48 (s, 3 H) 2.08 (s, 1 H) 3.52 (br. s., 1 H) 4.34 (s, 1 H) 6.40 (s, 1 H) 7.71 (s, 1 H) 8.60 (s, 1 H) 8.69 (s, 1 H) 9.09 (s, 1 H) 9.44 (s, 1 H) 11.36 (s, 1 H). ESI-MS m/z [M+H]+ 416.0.

EXAMPLE 115

N-(5-(6-cyano-5-((1-(dimethylamino)-4-hydroxy-1-oxobutan-2-yl)amino)pyridin-3-yl)pyrazin-2-yl)cyclopropanecarboxamide

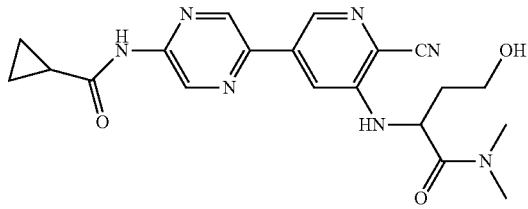 [SMILES: CN(C)C(=O)C(CCO)Nc1cc(-c2cnc(NC(=O)C3CC3)cn2)cnc1C#N]

The title compound was prepared in a manner similar to Example 30, except 2-amino-4-hydroxybutanoic acid was used to afford the title compound as a pale yellow solid (4.3 mg, 32.1% yield). 1H NMR (400 MHz, DMSO-d6) δ ppm 0.91 (s, 4 H) 1.84 (s, 1 H) 2.09 (s, 1 H) 2.89 (s, 3 H) 3.16 (s, 3 H) 3.54 (br. s., 2 H) 4.96 (br. s., 1 H) 6.37 (s, 1 H) 7.93 (s, 1 H) 8.65 (s, 1 H) 9.11 (s, 1 H) 9.46 (s, 1 H) 11.35 (s, 1 H). ESI-MS m/z [M+H]+ 410.0.

EXAMPLE 116

(S)-N-(5-(6-cyano-5-((1-oxo-1-((2,2,2-trifluoroethyl)amino)propan-2-yl)amino)pyridin-3-yl)pyrazin-2-yl)cyclopropanecarboxamide

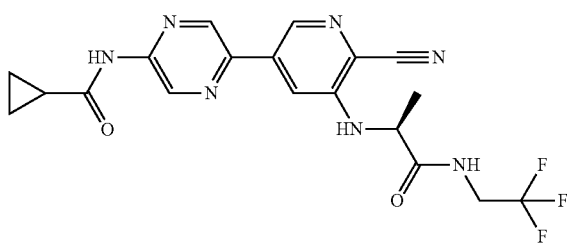 [SMILES: C[C@H](Nc1cc(-c2cnc(NC(=O)C3CC3)cn2)cnc1C#N)C(=O)NCC(F)(F)F]

The title compound was prepared in a manner similar to Example 30, except (S)-2-aminopropanoic was used, followed by 2,2,2-trifluoroethanamine, HCl to afford the title compound as pale yellow solid (24.5 mg, 49.8% yield). 1H NMR (400 MHz, DMSO-d6) δ ppm 0.92 (s, 3 H) 1.47 (s, 2 H) 2.08 (s, 1 H) 3.95 (s, 2 H) 4.37 (s, 1 H) 6.43 (s, 1 H) 7.70 (s, 1 H) 8.70 (s, 1 H) 8.84 (s, 1 H) 9.09 (s, 1 H) 9.44 (s, 1 H) 11.36 (s, 1 H). ESI-MS m/z [M+H]+ 434.0.

EXAMPLE 117

(S)-N-(5-(6-cyano-5-((1-((2,2-difluoropropyl)amino)-1-oxopropan-2-yl)amino)pyridin-3-yl)pyrazin-2-yl)cyclopropanecarboxamide

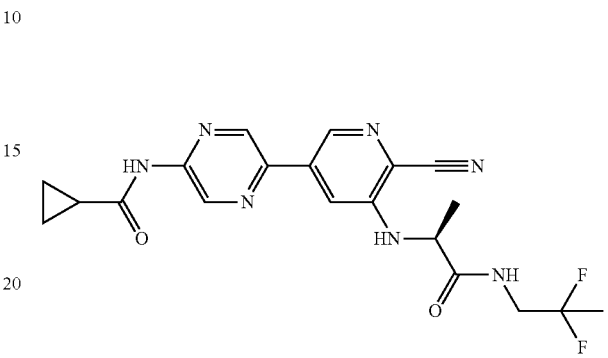

The title compound was prepared in a manner similar to Example 30, except (S)-2-aminopropanoic was used, followed by 2,2-difluoropropan-1-amine, HCl to afford the title compound as a pale yellow solid (16.2 mg, 44.3% yield). 1H NMR (400 MHz, DMSO-d6) δ ppm 0.96 (s, 3 H) 1.53 (s, 5H) 2.11 (s, 1 H) 3.63 (s, 2 H) 4.40 (s, 1 H) 6.43 (s, 1 H) 7.76 (s, 1 H) 8.67 (s, 1 H) 8.74 (s, 1 H) 9.15 (s, 1 H) 9.48 (s, 1 H) 11.41 (s, 1 H). ESI-MS m/z [M+H]+ 430.0.

EXAMPLE 118

N-(5-(6-cyano-5-(((2S)-1-((2,2-difluorocyclopropyl)amino)-1-oxopropan-2-yl)amino)pyridin-3-yl)pyrazin-2-yl)cyclopropanecarboxamide

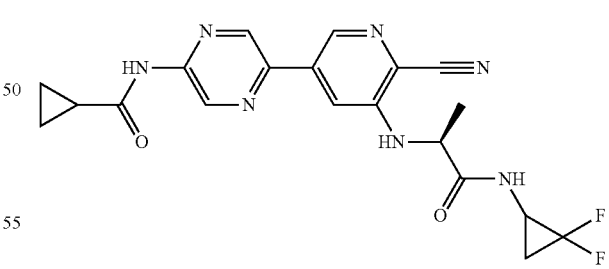

The title compound was prepared in a manner similar to Example 30, except (S)-2-aminopropanoic was used, followed by 2,2-difluorocyclopropanamine, HCl to afford the title compound as a yellow solid (2.3 mg, 6.32% yield). 1H NMR (400 MHz, methanol-d4) δ ppm 0.86 (br. s., 2 H) 0.94 (br. s., 3 H) 1.19 (s, 2 H) 1.32 (s, 1 H) 1.48 (s, 2 H) 1.70 (br. s., 1 H) 2.60 (s, 1 H) 4.16 (s, 1 H) 7.62 (s, 1 H) 8.52 (s, 1 H) 8.80 (br. s., 1 H) 9.37 (br. s., 1 H). ESI-MS m/z [M+H]+ 428.0.

EXAMPLE 119

N-(5-(6-cyano-5-(((2S)-1-((1,1-difluoropropan-2-yl)amino)-1-oxopropan-2-yl)amino)pyridin-3-yl)pyrazin-2-yl)cyclopropanecarboxamide

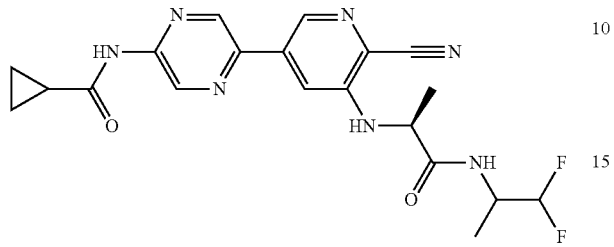

The title compound was prepared in a manner similar to Example 30, except (S)-2-aminopropanoic was used, followed by 1,1-difluoropropan-2-amine, HCl to afford the title compound as a pale yellow solid (18 mg, 49.2% yield). 1H NMR (400 MHz, DMSO-d6) δ ppm 0.92 (s, 3 H) 1.14 (s, 3 H) 1.46 (s, 3 H) 2.09 (s, 1 H) 4.18 (br. s., 1 H) 4.29 (s, 1 H) 6.38 (s, 1 H) 7.70 (s, 1 H) 8.50 (s, 1 H) 8.71 (s, 1 H) 9.11 (s, 1 H) 9.44 (s, 1 H) 11.37 (s, 1 H). ESI-MS m/z [M+H]+ 430.0.

EXAMPLE 120

(S)-N-(5-(6-cyano-5-((1-((2,2-difluoroethyl)amino)-1-oxobutan-2-yl)amino)pyridin-3-yl)pyrazin-2-yl)cyclopropanecarboxamide

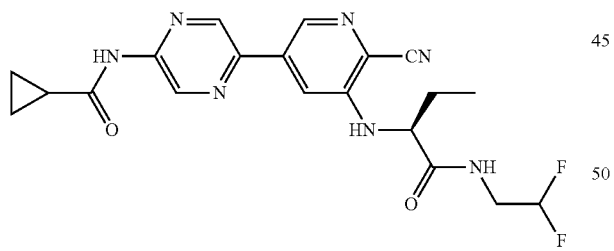

The title compound was prepared in a manner similar to Example 30, except (S)-2-aminobutanoic acid was used, followed by 2,2-difluoroethanamine to afford the title compound as a yellow solid (5 mg, 17.41% yield). 1H NMR (400 MHz, DMSO-d6) δ ppm 0.95 (s, 4 H) 0.92 (s, 4 H) 1.89 (s, 2 H) 2.10 (s, 1 H) 4.23 (s, 1 H) 6.26 (s, 1 H) 7.77 (s, 1 H) 8.69 (s, 2 H) 9.10 (s, 1 H) 9.45 (s, 1 H) 11.36 (s, 1 H). ESI-MS m/z [M+H]+ 430.0.

EXAMPLE 121

N-(5-(5-((2-amino-2-oxoethyl)amino)-6-cyanopyridin-3-yl)pyrazin-2-yl)cyclopropanecarboxamide

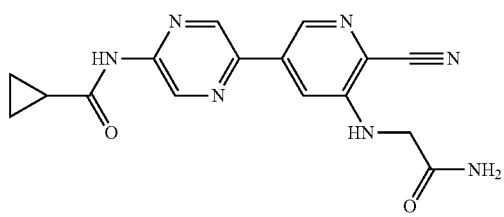 [SMILES: N#Cc1ncc(-c2cnc(NC(=O)C3CC3)cn2)cc1NCC(N)=O]

The title compound was prepared in a manner similar to Example 30, except 2-aminoacetamide hydrochloride was used and subjected to microwave irradiation at 100° C. for 30 minutes to afford the title compound as a tan solid (13 mg, 21.83% yield). 1H NMR (400 MHz, DMSO-d6) δ ppm 0.89 (d, J=5.81 Hz, 4 H) 2.01-2.12 (m, 1 H) 3.92 (d, J=5.81 Hz, 2 H) 6.54 (br. s., 1 H) 6.64 (t, J=5.68 Hz, 1 H) 7.21 (s, 1 H) 7.57 (s, 1 H) 7.66 (d, J=1.52 Hz, 1 H) 8.63 (d, J=1.26 Hz, 1 H) 9.12 (d, J=1.26 Hz, 1 H) 9.43 (d, J=1.26 Hz, 1 H) 11.34 (s, 1 H). ESI-MS m/z [M+H]+ 338.0.

EXAMPLE 122

N-(5-(6-cyano-5-((2-(dimethylamino)-2-oxoethyl)amino)pyridin-3-yl)pyrazin-2-yl)cyclopropanecarboxamide

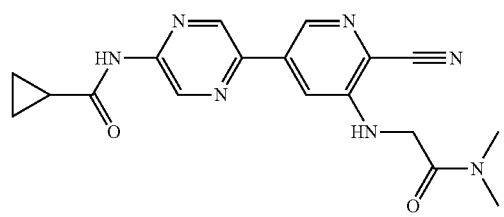

The title compound was prepared in a manner similar to Example 30, except 2-amino-N,N-dimethylacetamide was used and subjected to microwave irradiation at 100° C. for 30 minutes to afford the title compound as a yellow solid (12 mg, 18.61% yield). 1H NMR (400 MHz, DMSO-d6) δ ppm 0.82-0.96 (m, 4 H) 2.07 (quin, J=6.13 Hz, 1 H) 2.91 (s, 3 H) 3.05 (s, 3 H) 4.21 (br. s., 2 H) 6.29 (br. s., 1 H) 7.83 (d, J=1.52 Hz, 1 H) 8.63 (d, J=1.52 Hz, 1 H) 9.14 (d, J=1.26 Hz, 1 H) 9.45 (d, J=1.26 Hz, 1 H) 11.34 (s, 1 H). ESI-MS m/z [M+H]+ 366.0.

EXAMPLE 123

N-(5-(4-cyano-3-((2-(dimethylamino)-2-oxoethyl)amino)phenyl)pyrazin-2-yl)cyclopropanecarboxamide

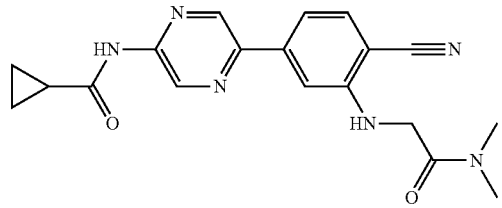 [SMILES: CN(C)C(=O)CNc1cc(-c2cnc(NC(=O)C3CC3)cn2)ccc1C#N]

The title compound was prepared in a manner similar to Example 1, except 2-amino-N,N-dimethylacetamide was used and subjected to microwave irradiation at 100° C. for 1 hour to afford the title compound as a tan solid (8.2 mg, 12.7% yield). 1H NMR (400 MHz, DMSO-d6) δ ppm 0.83-0.95 (m, 4 H) 2.01-2.14 (m, 1 H) 2.92 (s, 3 H) 3.06 (s, 3 H) 4.17 (d, J=3.54 Hz, 2H) 6.07 (br. s., 1 H) 7.38-7.46 (m, 2 H) 7.64 (d, J=8.84 Hz, 1 H) 9.08 (d, J=1.26 Hz, 1 H) 9.41 (d, J=1.26 Hz, 1 H) 11.27 (s, 1 H). ESI-MS m/z [M+H]+ 365.0.

EXAMPLE 124

N-(5-(4-cyano-3-((2-(ethylamino)-2-oxoethyl)amino)phenyl)pyrazin-2-yl)cyclopropanecarboxamide

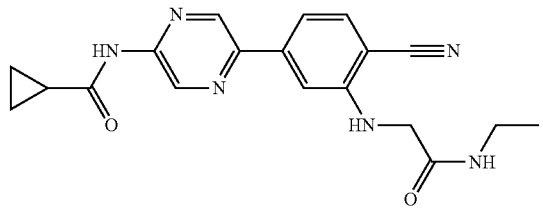 [SMILES: CCNC(=O)CNc1cc(-c2cnc(NC(=O)C3CC3)cn2)ccc1C#N]

The title compound was prepared in a manner similar to Example 1, except 2-amino-N-ethylacetamide was used and subjected to microwave irradiation at 150° C. for one hour to afford the title compound as a white solid (13 mg, 20.14% yield). 1H NMR (400 MHz, DMSO-d6) δ ppm 0.82-0.94 (m, 4 H) 1.00 (t, J=7.20 Hz, 3 H) 2.00-2.10 (m, 1 H) 3.05-3.17 (m, 2 H) 3.89 (d, J=5.05 Hz, 2 H) 6.35 (t, J=5.31 Hz, 1 H) 7.27 (s, 1 H) 7.41 (dd, J=8.08, 1.01 Hz, 1 H) 7.63 (d, J=8.08 Hz, 1 H) 8.11 (t, J=5.56 Hz, 1 H) 8.99 (d, J=1.26 Hz, 1 H) 9.39 (d, J=1.26 Hz, 1 H) 11.27 (s, 1 H). ESI-MS m/z [M+H]+ 365.0.

EXAMPLE 125

N-(5-(4-cyano-3-((2-oxo-2-(pyrrolidin-1-yl)ethyl)amino)phenyl)pyrazin-2-yl)cyclopropanecarboxamide

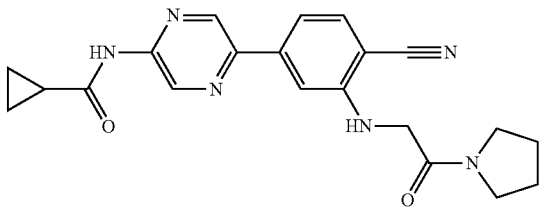 [SMILES: N#Cc1ccc(-c2cnc(NC(=O)C3CC3)cn2)cc1NCC(=O)N1CCCC1]

The title compound was prepared in a manner similar to Example 1, except triethylamine and 2-amino-1-(pyrrolidin-1-yl)ethanone hydrochloride were used and subjected to microwave irradiation at 150° C. for one hour to afford the title compound as a yellow solid (12 mg, 17.35% yield). 1H NMR (400 MHz, DMSO-d6) δ ppm 0.83-0.94 (m, 4 H) 1.77-1.86 (m, 2 H) 1.93 (quin, J=6.69 Hz, 2 H) 2.02-2.13 (m, 1 H) 3.38 (t, J=6.82 Hz, 2 H) 3.52 (t, J=6.69 Hz, 2 H) 4.10 (s, 2 H) 6.08 (br. s., 1 H) 7.37-7.46 (m, 2 H) 7.64 (d, J=8.08 Hz, 1 H) 9.07 (d, J=1.26 Hz, 1 H) 9.41 (d, J=1.26 Hz, 1 H) 11.27 (s, 1 H). ESI-MS m/z [M+H]+ 391.2.

EXAMPLE 126

N-(5-(4-cyano-3-((2-(methyl(2,2,2-trifluoroethyl)amino)-2-oxoethyl)amino)phenyl)pyrazin-2-yl)cyclopropanecarboxamide

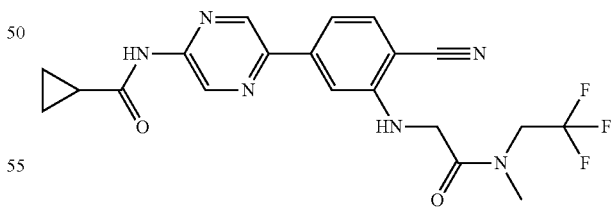

The title compound was prepared in a manner similar to Example 1, except triethylamine and 2-amino-N-methyl-N-(2,2,2-trifluoroethyl)acetamide were used and subjected to microwave irradiation at 150° C. for one hour to afford the title compound as a tan solid (7.5 mg, 9.79% yield). 1H NMR (400 MHz, DMSO-d6) δ ppm 0.89 (d, J=5.31 Hz, 7 H) 2.01-2.14 (m, 1 H) 4.16-4.37 (m, 4 H) 7.34-7.46 (m, 2 H) 7.64 (d, J=7.83 Hz, 1 H) 8.97-9.08 (m, 1 H) 9.37-9.49 (m, 1 H) 11.27 (s, 1 H). ESI-MS m/z [M+H]+ 433.1.

EXAMPLE 127

(S)-N-(5-(5-cyano-4-((1-(dimethylamino)-1-oxobutan-2-yl)amino)pyridin-2-yl)pyrazin-2-yl)cyclopropanecarboxamide

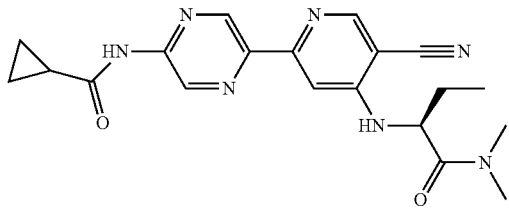 [SMILES: CC[C@H](Nc1cc(-c2cnc(NC(=O)C3CC3)cn2)ncc1C#N)C(=O)N(C)C]

A mixture of 4,6-dichloronicotinonitrile, (S)-2-aminobutanoic acid, and DIPEA were dissolved in anhydrous DMF. The reaction was heated at 80° C. for 2 hours to afford (S)-2-((2-chloro-5-cyanopyridin-4-yl)amino)-N,N-dimethylbutanamide.

A mixture of N-(5-bromopyrazin-2-yl)cyclopropanecarboxamide, tetrakis(triphenylphosphine)palladium(0), and 1,1,1,2,2,2-hexamethyldistannane were heated at 110° C. for 16 hours to afford N-(5-(trimethylstannyl)pyrazin-2-yl)cyclopropanecarboxamide.

A mixture of (S)-2-((2-chloro-5-cyanopyridin-4-yl)amino)-N,N-dimethylbutanamide, N-(5-(trimethylstannyl)pyrazin-2-yl)cyclopropanecarboxamide, and tetrakis(triphenylphosphine)palladium(0) were dissolved in anhydrous toluene. The reaction was heated at 100° C. for 16 hours to afford the title compound as a light pink solid (90.11 mg). 1H NMR (400 MHz, DMSO-d6) δ ppm 0.91 (s, 7 H) 1.85 (m, 2 H) 2.07 (br. s., 1 H) 2.90 (s, 3 H) 3.16 (s, 3 H) 4.96 (br. s., 1 H) 6.92 (s, 1 H) 7.68 (s, 1 H) 8.61 (s, 1 H) 9.23 (s, 1 H) 9.44 (s, 1 H) 11.37 (s, 1 H). ESI-MS m/z [M+H]+ 394.0. ESI-MS m/z [M+H]+ 394.1.

EXAMPLE 128

(S)-N-(5-(6-cyano-5-((1-(dimethylamino)-3-hydroxy-1-oxopropan-2-yl)amino)pyridin-3-yl)pyrazin-2-yl)cyclopropanecarboxamide

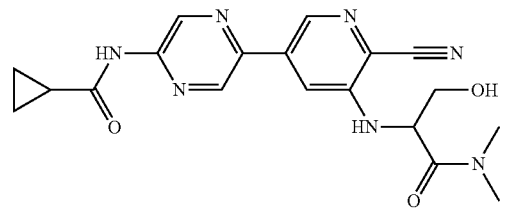 [SMILES: CN(C)C(=O)C(CO)Nc1cc(-c2cnc(NC(=O)C3CC3)cn2)cnc1C#N]

The title compound was prepared in a manner similar to Example 30, except 2-amino-3-hydroxypropanoic acid was used to afford the title compound. 1H NMR (500 MHz, DMSO-d6) δ ppm 0.90 (s, 4 H) 2.07 (s, 1 H) 2.90 (s, 3 H) 3.16 (s, 3 H) 3.63 (br. s., 1 H) 3.73 (br. s., 1 H) 4.96 (s, 1 H) 5.14 (br. s., 1 H) 6.13 (s, 1 H) 7.99 (s, 1 H) 8.62 (s, 1 H) 9.11 (s, 1 H) 9.45 (s, 1 H) 11.32 (s, 1 H). ESI-MS m/z [M+H]+ 396.0.

EXAMPLE 129

(S)-N-(5-(6-cyano-5-((1-(dimethylamino)-1-oxopropan-2-yl)amino)pyridin-3-yl)pyrazin-2-yl)cyclopropanecarboxamide

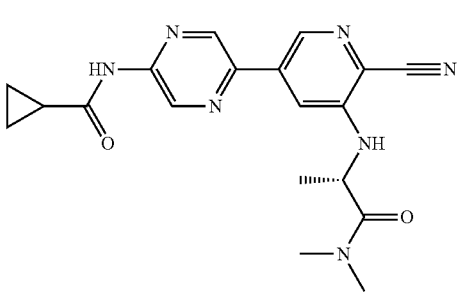 [SMILES: C[C@H](Nc1cc(-c2cnc(NC(=O)C3CC3)cn2)cnc1C#N)C(=O)N(C)C]

The title compound was prepared in a manner similar to Example 30, except (S)-2-amino-N,N-dimethylpropanoic acid was used yielding 15 mg (54% yield) of material. 1H NMR (400 MHz, DMSO-d6) δ ppm 0.85-0.92 (m, 4 H) 1.34 (d, J=6.57 Hz, 3 H) 2.05-2.11 (m, 1 H) 2.90 (s, 3 H) 3.14 (s, 3 H) 4.90 (t, J=6.82 Hz, 1 H) 6.22 (d, J=7.33 Hz, 1 H) 7.92 (d, J=1.77 Hz, 1 H) 8.63 (d, J=1.52 Hz, 1 H) 9.14 (d, J=1.52 Hz, 1 H) 9.45 (d, J=1.26 Hz, 1 H) 11.32 (s, 1 H); ESI-MS m/z [M+H]+ 380.4.

EXAMPLE 130

N-(5-(4-cyano-3-((2-((2-hydroxyethyl)(methyl)amino)-2-oxoethyl)amino)phenyl)pyrazin-2-yl)cyclopropanecarboxamide

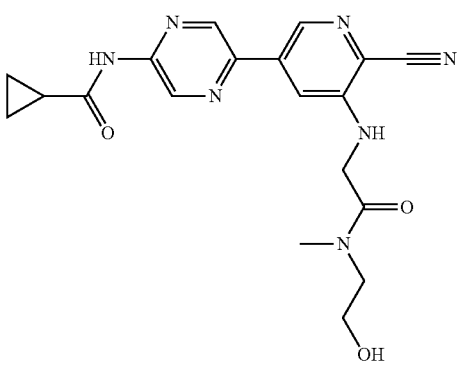 [SMILES: CN(CCO)C(=O)CNc1cc(-c2cnc(NC(=O)C3CC3)cn2)cnc1C#N]

The title compound was prepared in a manner similar to Example 30, except glycine was used followed by 2-(methylamino)ethan-1-ol yielding 15 mg (54% yield) of material. 1H NMR (400 MHz, DMSO-d6) δ ppm 0.86-0.92 (m, 4 H) 1.03 (d, J=6.82 Hz, 1 H) 1.11 (d, J=6.82 Hz, 2H) 2.03-2.09 (m, 1 H) 2.76 (s, 2 H) 2.91 (s, 1 H) 3.41-3.47 (m, 1 H) 4.14 (br. s., 1 H) 4.21 (br. s., 1 H) 6.16 (dt, J=16.23, 4.52 Hz, 1 H) 7.42 (t, J=4.17 Hz, 2 H) 7.64 (d, J=8.34 Hz, 1 H) 9.07 (dd, J=4.29, 1.52 Hz, 1 H) 9.40-9.42 (m, 1 H) 11.24 (s, 1 H); ESI-MS m/z [M+H]+ 394.2.

EXAMPLE 131

(S)-N-(5-(6-cyano-5-((1-(dimethylamino)-4-methoxy-1-oxobutan-2-yl)amino)pyridin-3-yl)pyrazin-2-yl)cyclopropanecarboxamide

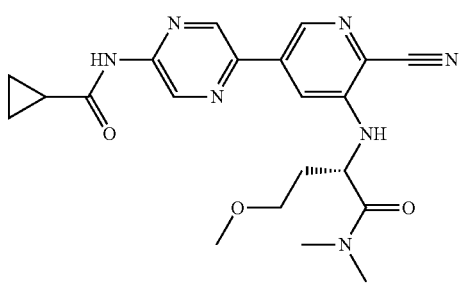 [SMILES: COCC[C@H](Nc1cc(-c2cnc(NC(=O)C3CC3)cn2)cnc1C#N)C(=O)N(C)C]

The title compound was prepared in a manner similar to Example 30, except (S)-2-amino-4-methoxy-N,N-dimethylbutanoic acid was used yielding 2 mg (7% yield) of material. 1H NMR (400 MHz, methanol-d4) δ ppm 0.92-0.97 (m, 2 H) 1.04 (t, J=3.66 Hz, 2 H) 1.93-2.01 (m, 2 H) 2.16-2.24 (m, 1 H) 2.98 (s, 3 H) 3.24 (s, 3 H) 3.35 (s, 3 H) 3.52-3.55 (m, 2 H) 4.92-4.97 (m, 1 H) 7.86 (d, J=1.52 Hz, 1 H) 8.58 (d, J=1.52 Hz, 1 H) 8.93 (br. s., 1 H) 9.48 (br. s., 1H); ESI-MS m/z [M+H]+ 424.5.

EXAMPLE 132

N-(5-(4-cyano-3-((2-(3-hydroxy-3-methylpyrrolidin-1-yl)-2-oxoethyl)amino)phenyl)pyrazin-2-yl)cyclopropanecarboxamide

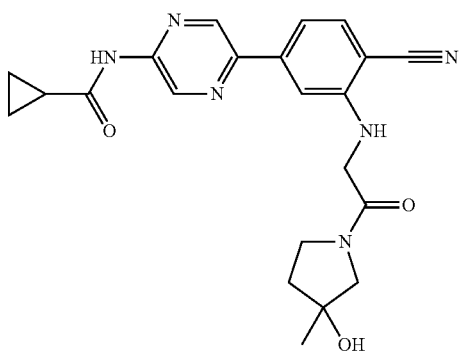 [SMILES: CC1(O)CCN(C(=O)CNc2cc(-c3cnc(NC(=O)C4CC4)cn3)ccc2C#N)C1]

The title compound was prepared in a manner similar to Example 5, except glycine was used followed by 3-methylpyrrolidin-3-ol used yielding 13 mg (40% yield) of material. 1H NMR (400 MHz, DMSO-d6) δ ppm 0.87-0.92 (m, 4 H) 1.33 (d, J=11.37 Hz, 3 H) 1.74-1.93 (m, 2 H) 2.04-2.10 (m, 1 H) 3.38-3.43 (m, 1 H) 3.45-3.54 (m, 2 H) 4.04 (s, 1 H) 4.11 (d, J=10.86 Hz, 1H) 7.39-7.44 (m, 2 H) 7.64 (d, J=8.34 Hz, 1 H) 9.06 (dd, J=4.04, 1.52 Hz, 1 H) 9.41 (t, J=1.39 Hz, 1 H) 11.24 (s, 1 H); ESI-MS m/z [M+H]+ 421.5.

EXAMPLE 133

N-(5-(4-cyano-3-((2-((1-hydroxypropan-2-yl)(methyl)amino)-2-oxoethyl)amino)phenyl)pyrazin-2-yl)cyclopropanecarboxamide

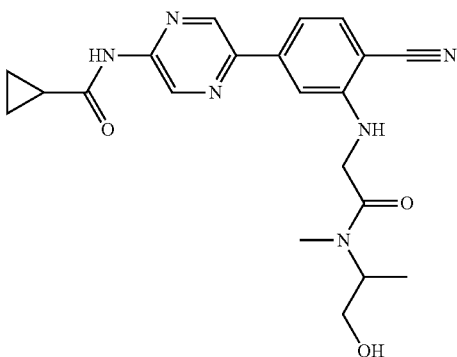 [SMILES: CC(CO)N(C)C(=O)CNc1cc(-c2cnc(NC(=O)C3CC3)cn2)ccc1C#N]

The title compound was prepared in a manner similar to Example 5, except glycine was used followed by 2-(methylamino)propan-1-ol yielding 6 mg (36% yield) of material. 1H NMR (400 MHz, DMSO-d6) δ ppm 0.86-0.92 (m, 4 H) 1.03 (d, J=6.82 Hz, 1 H) 1.11 (d, J=6.82 Hz, 2H) 2.03-2.09 (m, 1 H) 2.76 (s, 2 H) 2.91 (s, 1 H) 3.41-3.47 (m, 1 H) 4.14 (br. s., 1 H) 4.21 (br. s., 1 H) 6.16 (dt, J=16.23, 4.52 Hz, 1 H) 7.42 (t, J=4.17 Hz, 2 H) 7.64 (d, J=8.34 Hz, 1 H) 9.07 (dd, J=4.29, 1.52 Hz, 1 H) 9.40-9.42 (m, 1 H) 11.24 (s, 1 H); ESI-MS m/z [M+H]+ 409.4.

EXAMPLE 134

N-(5-(4-cyano-3-((2-((2-hydroxypropyl)(methyl)amino)-2-oxoethyl)amino)phenyl)pyrazin-2-yl)cyclopropanecarboxamide

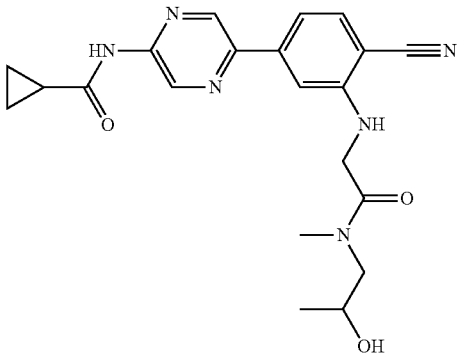 [SMILES: CC(O)CN(C)C(=O)CNc1cc(-c2cnc(NC(=O)C3CC3)cn2)ccc1C#N]

The title compound was prepared in a manner similar to Example 5, except glycine was used followed by 1-(methylamino)propan-1-ol yielding 5 mg (16% yield) of material. 1H NMR (400 MHz, DMSO-d6) δ ppm 0.86-0.92 (m, 5H) 1.03 (d, J=6.32 Hz, 2 H) 1.14 (d, J=6.32 Hz, 2H) 2.07 (quin, J=6.13 Hz, 1 H) 2.92 (s, 2 H) 3.11 (s, 2 H) 3.20 (dd, J=13.26, 5.68 Hz, 1 H) 3.38 (dt, J=13.89, 5.68 Hz, 2 H) 3.84-3.94 (m, 1 H) 4.13-4.23 (m, 2 H) 7.38-7.44 (m, 2 H) 7.63 (dd, J=8.21, 4.17 Hz, 1 H) 9.05 (dd, J=12.88, 1.52 Hz, 1 H) 9.41 (s, 1 H) 11.24 (d, J=2.78 Hz, 1H); ESI-MS m/z [M+H]+ 409.4.

EXAMPLE 135

(S)-N-(5-(6-cyano-5-((1-(dimethylamino)-1-oxopropan-2-yl)amino)pyridin-3-yl)pyrazin-2-yl)cyclopropanecarboxamide

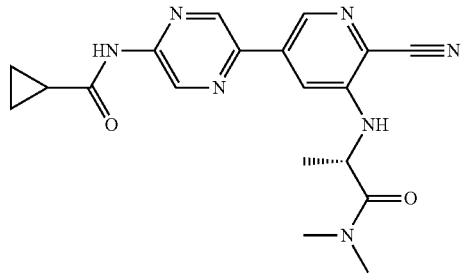 [SMILES: C[C@H](Nc1cc(-c2cnc(NC(=O)C3CC3)cn2)cnc1C#N)C(=O)N(C)C]

The title compound was prepared in a manner similar to Example 30, except L-alanine was used yielding 6 mg (17% yield) of material. 1H NMR (400 MHz, methanol-d4) δ ppm 0.93-0.97 (m, 2 H) 0.99-1.03 (m, 3 H) 1.03-1.05 (m, 2 H) 1.84 (dd, J=14.40, 7.07 Hz, 1 H) 1.93-1.98 (m, 2 H) 2.99 (s, 3 H) 3.25 (s, 3 H) 4.85-4.88 (m, 1 H) 7.88 (d, J=1.52 Hz, 1 H) 8.58 (s, 1 H) 8.95 (br. s., 1 H) 9.49 (br. s., 1 H); ESI-MS m/z [M+H]+ 394.4.

EXAMPLE 136

(S)-N-(5-(4-cyano-3-((1-(dimethylamino)-3-hydroxy-1-oxopropan-2-yl)amino)phenyl)pyrazin-2-yl)cyclopropanecarboxamide

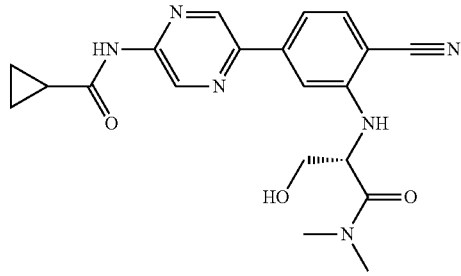 [SMILES: CN(C)C(=O)[C@H](CO)Nc1cc(-c2cnc(NC(=O)C3CC3)cn2)ccc1C#N]

The title compound was prepared in a manner similar to Example 30, except L-alanine was used yielding 13 mg (40% yield) of material. 1H NMR (400 MHz, DMSO-d6) δ ppm 0.86-0.91 (m, 4 H) 2.04-2.11 (m, 1 H) 2.89 (s, 3 H) 3.18 (s, 3 H) 3.65-3.75 (m, 2 H) 4.89-4.95 (m, 1 H) 5.11 (br. s., 1 H) 5.93 (d, J=7.83 Hz, 1 H) 7.41 (dd, J=8.08, 1.52 Hz, 1 H) 7.53-7.56 (m, 1 H) 7.62 (d, J=8.08 Hz, 1 H) 9.04 (d, J=1.52 Hz, 1 H) 9.41 (d, J=1.52 Hz, 1 H) 11.23 (s, 1 H); ESI-MS m/z [M+H]+; ESI-MS m/z [M+H]+ 395.4.

EXAMPLE 137

(S)-N-(5-(4-cyano-3-((1-(dimethylamino)-1-oxopropan-2-yl)amino)-5-fluorophenyl)pyrazin-2-yl)cyclopropanecarboxamide

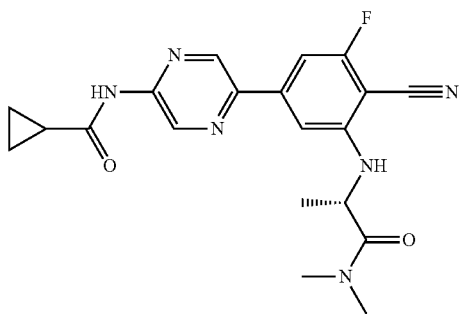 [SMILES: C[C@H](Nc1cc(-c2cnc(NC(=O)C3CC3)cn2)cc(F)c1C#N)C(=O)N(C)C]

The title compound was prepared in a manner similar to Example 1, except N-(5-(4-cyano-3,5-difluorophenyl)pyrazin-2-1)cyclopropanecarboxamide was used yielding 4 mg (6% yield) of material. 1H NMR (400 MHz, DMSO-d6) δ ppm 0.87-0.93 (m, 4 H) 1.35 (d, J=6.57 Hz, 3 H) 2.05-2.09 (m, 1 H) 2.91 (s, 3 H) 3.15 (s, 3 H) 4.86-4.95 (m, 1 H) 6.33 (d, J=7.07 Hz, 1 H) 7.27-7.35 (m, 1 H) 7.37 (s, 1 H) 9.12 (d, J=1.52 Hz, 1 H) 9.43 (d, J=1.52 Hz, 1 H) 11.30 (s, 1 H) ESI-MS m/z [M+H]+ 397.2.

EXAMPLE 138

N-(5-(6-cyano-5-((1-(dimethylamino)-4,4,4-trifluoro-1-oxobutan-2-yl)amino)pyridin-3-yl)pyrazin-2-yl)cyclopropanecarboxamide

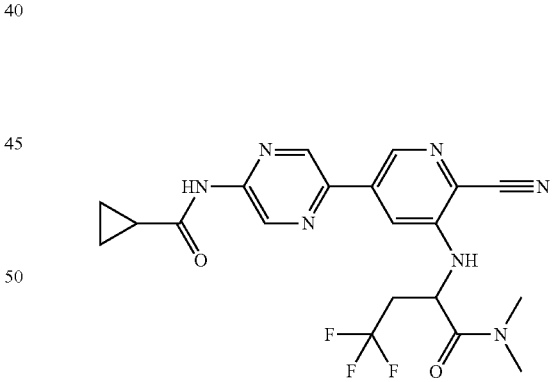

The title compound was prepared in a manner similar to Example 30, except 2-amino-4,4,4-trifluorobutanoic acid was used yielding 10 mg (27% yield) of material. 1H NMR (400 MHz, DMSO-d6) δ ppm 0.90 (d, J=6.32 Hz, 4 H) 2.04-2.12 (m, 1 H) 2.89 (s, 3 H) 2.90-2.97 (m, 2 H) 3.14 (s, 3 H) 5.11-5.19 (m, 1 H) 6.63 (d, J=8.59 Hz, 1 H) 7.95 (d, J=1.77 Hz, 1 H) 8.68 (d, J=1.52 Hz, 1 H) 9.11 (d, J=1.52 Hz, 1 H) 9.45 (d, J=1.52 Hz, 1 H) 11.35 (s, 1 H) ESI-MS m/z [M+H]+ 448.5.

EXAMPLE 139

N-(5-(6-cyano-5-(((S)-1-((S)-3-fluoropyrrolidin-1-yl)-1-oxopropan-2-yl)amino)pyridin-3-yl)pyrazin-2-yl)cyclopropanecarboxamide

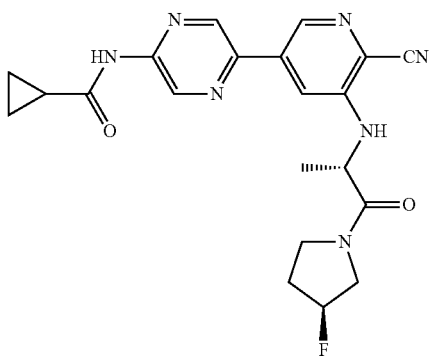 [SMILES: C[C@H](Nc1cc(-c2cnc(NC(=O)C3CC3)cn2)cnc1C#N)C(=O)N1CC[C@H](F)C1]

The title compound was prepared in a manner similar to Example 30, except (S)-2-((2-cyano-5-(5-(cyclopropanecarboxamido)pyrazin-2-yl)pyridin-3-yl)amino)propanoic acid was used followed by (S)-3-fluoropyrrolidine yielding 9 mg (15% yield) of material. 1H NMR (400 MHz, DMSO-d6) δ ppm 0.90 (d, J=5.56 Hz, 4 H) 1.39 (dd, J=16.42, 6.57 Hz, 3 H) 2.03-2.14 (m, 2 H) 2.16 (br. s., 1 H) 2.28 (br. s., 1 H) 3.64-3.85 (m, 3 H) 3.85-3.97 (m, 1 H) 4.66 (dt, J=13.33, 6.85 Hz, 1 H) 6.30 (dd, J=12.76, 7.45 Hz, 1 H) 7.82 (d, J=1.77 Hz, 1 H) 8.66 (d, J=1.01 Hz, 1 H) 9.12 (dd, J=13.89, 1.52 Hz, 1 H) 9.45 (dd, J=3.92, 1.39 Hz, 1 H) 11.35 (s, 1 H) ESI-MS m/z [M+H]+ 424.3.

EXAMPLE 140

N-(5-(6-cyano-5-((2-(1,1-dioxidothiazolidin-3-yl)-2-oxoethyl)amino)pyridin-3-yl)pyrazin-2-yl)cyclopropanecarboxamide

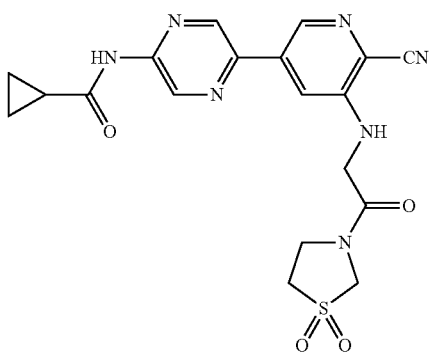 [SMILES: N#Cc1ncc(-c2cnc(NC(=O)C3CC3)cn2)cc1NCC(=O)N1CCS(=O)(=O)C1]

The title compound was prepared in a manner similar to Example 5, except glycine was used followed by thiazolidine 1,1-dioxide yielding 6 mg (10% yield) of material. 1H NMR (400 MHz, DMSO-d6) δ ppm 0.87-0.95 (m, 4 H) 2.02-2.12 (m, 1 H) 3.47 (t, J=7.20 Hz, 1 H) 3.61 (t, J=6.95 Hz, 1 H) 3.91 (t, J=7.20 Hz, 1 H) 4.17 (t, J=7.33 Hz, 1 H) 4.24 (d, J=5.56 Hz, 1 H) 4.39 (d, J=5.31 Hz, 1 H) 4.55 (s, 1 H) 4.87 (s, 1 H) 6.44-6.56 (m, 1 H) 7.73-7.84 (m, 1 H) 8.65 (d, J=1.52 Hz, 1 H) 9.10 (d, J=2.02 Hz, 1 H) 9.45 (d, J=1.52 Hz, 1 H) 11.35 (s, 1 H) ESI-MS m/z [M+H]+ 442.1.

EXAMPLE 141

(R)-N-(5-(6-cyano-5-((2-(2-(difluoromethyl)pyrrolidin-1-yl)-2-oxoethyl)amino)pyridin-3-yl)pyrazin-2-yl)cyclopropanecarboxamide

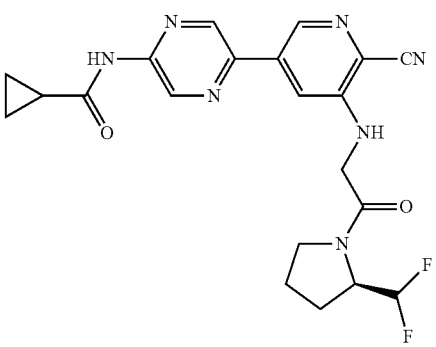 [SMILES: N#Cc1ncc(-c2cnc(NC(=O)C3CC3)cn2)cc1NCC(=O)N1CCC[C@@H]1C(F)F]

The title compound was prepared in a manner similar to Example 5, except glycine was used followed by (R)-2-(difluoromethyl)pyrrolidine yielding 11 mg (28% yield) of material. 1H NMR (400 MHz, DMSO-d6) δ ppm 0.86-0.93 (m, 4 H) 1.93-2.11 (m, 5H) 3.62 (d, J=6.32 Hz, 2 H) 4.25 (d, J=4.29 Hz, 2 H) 6.44 (br. s., 1 H) 7.79 (d, J=1.77 Hz, 1 H) 8.64 (d, J=1.77 Hz, 1 H) 9.11 (d, J=1.52 Hz, 1 H) 9.44 (d, J=1.52 Hz, 1 H) 11.35 (s, 1 H) ESI-MS m/z [M+H]+ 442.3.

EXAMPLE 142

N-(5-(6-cyano-5-((2-(3,3-difluoropyrrolidin-1-yl)-2-oxoethyl)amino)pyridin-3-yl)pyrazin-2-yl)cyclopropanecarboxamide

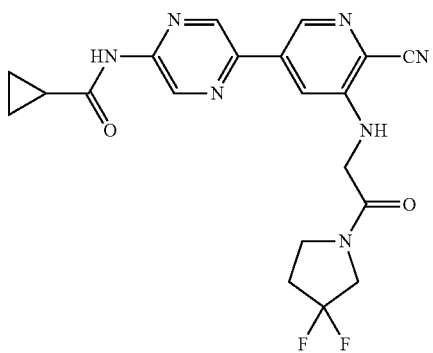 [SMILES: N#Cc1ncc(-c2cnc(NC(=O)C3CC3)cn2)cc1NCC(=O)N1CCC(F)(F)C1]

The title compound was prepared in a manner similar to Example 5, except glycine was used followed by 3,3-difluoropyrrolidine yielding 12 mg (31% yield) of material. 1H NMR (400 MHz, DMSO-d6) δ ppm 0.86-0.94 (m, 4 H) 2.08 (quin, J=6.25 Hz, 1 H) 2.37-2.44 (m, 1 H) 2.55-2.61 (m, 1 H) 3.60 (t, J=7.45 Hz, 1 H) 3.73-3.87 (m, 2 H) 4.08 (t, J=13.01 Hz, 1 H) 4.17 (d, J=5.05 Hz, 1 H) 4.24 (d, J=4.80 Hz, 1 H) 6.39 (br. s., 1 H) 7.80 (dd, J=4.17, 1.64 Hz, 1 H) 8.65 (d, J=1.26 Hz, 1 H) 9.12 (d, J=1.01 Hz, 1 H) 9.45 (t, J=1.39 Hz, 1 H) 11.35 (s, 1 H) ESI-MS m/z [M+H]+ 468.4.

EXAMPLE 143

N-(5-(6-cyano-5-((2-(2-(fluoromethyl)pyrrolidin-1-yl)-2-oxoethyl)amino)pyridin-3-yl)pyrazin-2-yl)cyclopropanecarboxamide

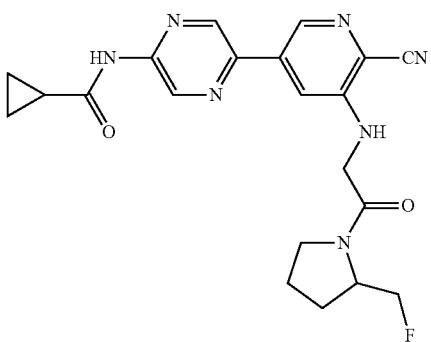 [SMILES: N#Cc1ncc(-c2cnc(NC(=O)C3CC3)cn2)cc1NCC(=O)N1CCCC1CF]

The title compound was prepared in a manner similar to Example 5, except glycine was used, followed by 2-(fluoromethyl)pyrrolidine yielding 2 mg (3% yield) of material. 1H NMR (400 MHz, DMSO-d6) ppm 0.85-0.93 (m, 4 H) 1.82-2.02 (m, 5H) 2.03-2.10 (m, 1 H) 3.57 (d, J=5.31 Hz, 2 H) 4.16-4.23 (m, 2 H) 4.39-4.46 (m, 1 H) 4.55 (dd, J=6.57, 4.04 Hz, 1 H) 6.39 (t, J=4.93 Hz, 1 H) 7.79 (d, J=1.52 Hz, 1 H) 8.64 (d, J=1.52 Hz, 1 H) 9.12 (d, J=1.52 Hz, 1H) 9.44 (d, J=1.52 Hz, 1 H) 11.34 (s, 1 H) ESI-MS m/z [M+H]+ 424.3.

EXAMPLE 144

N-(5-(5-((2-amino-2-oxoethyl)amino)-6-cyanopyridin-3-yl)pyrazin-2-yl)-2-methylcyclopropanecarboxamide

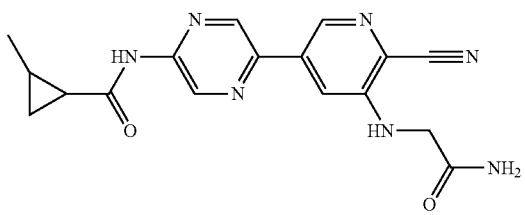 [SMILES: CC1CC1C(=O)Nc1cnc(-c2cnc(C#N)c(NCC(N)=O)c2)cn1]

The title compound was prepared in a manner similar to Example 30, except N-(5-bromopyrazin-2-yl)-2-methylcyclopropanecarboxamide was used, followed by 2-aminoacetamide hydrochloride and using pyridine instead of potassium carbonate. The reaction was subjected to microwave irradiation at 150° C. for 1 hour to afford the title compound as a yellow solid (9.5 mg, 20.1% yield). 1H NMR (500 MHz, DMSO-d6) δ ppm 0.69-0.90 (m, 1 H) 1.00-1.18 (m, 4 H) 1.32 (d, J=2.44 Hz, 1 H) 1.76-2.12 (m, 1 H) 3.92 (d, J=5.37 Hz, 2 H) 6.63 (t, J=5.61 Hz, 1 H) 7.20 (s, 1 H) 7.57 (br. s., 1 H) 7.66 (d, J=1.95 Hz, 1 H) 8.63 (d, J=1.95 Hz, 1H) 9.06-9.13 (m, 1 H) 9.37-9.49 (m, 1 H) 11.19-11.30 (m, 1 H). ESI-MS: m/z [M+H]+ 352.6.

EXAMPLE 145

N-(5-(6-cyano-5-((2-(dimethylamino)-2-oxoethyl)amino)pyridin-3-yl)pyrazin-2-yl)-2-methylcyclopropanecarboxamide

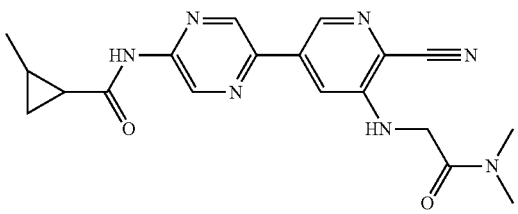

The title compound was prepared in a manner similar to Example 30, except N-(5-bromopyrazin-2-yl)-2-methylcyclopropanecarboxamide was used, followed by 2-amino-N,N-dimethylacetamide. The reaction was subjected to microwave irradiation at 130° C. for 30 minutes to afford the title compound as a light yellow solid (8.8 mg, 17.2% yield). 1H NMR (500 MHz, DMSO-d6) δ ppm 0.71-0.92 (m, 1 H) 1.00-1.18 (m, 4 H) 1.22-1.42 (m, 1 H) 1.83 (dt, J=8.05, 4.27 Hz, 1 H) 2.86-2.95 (m, 3 H) 3.01-3.08 (m, 3 H) 4.21 (d, J=3.42 Hz, 2 H) 6.29 (br. s., 1 H) 7.79-7.86 (m, 1 H) 8.63 (d, J=1.46 Hz, 1 H) 9.10-9.17 (m, 1 H) 9.39-9.49 (m, 1 H) 11.21-11.28 (m, 1 H). ESI-MS: m/z [M+H]+ 380.6.

EXAMPLE 146

N-(5-(6-cyano-5-(((S)-1-((2,2-difluoroethyl)(methyl)amino)-1-oxopropan-2-yl)amino)pyridin-3-yl)pyrazin-2-yl)-2-(hydroxymethyl)cyclopropanecarboxamide

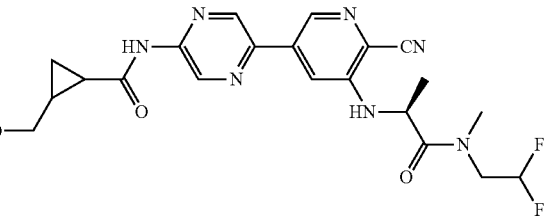

The title compound was prepared in a manner similar to Example 30, except 2-((benzyloxy)methyl)-N-(5-(6-cyano-5-fluoropyridin-3-yl)pyrazin-2-yl)cyclopropanecarboxamide was used, followed by (S)-2-aminopropanoic acid and then 2,2-difluoro-N-methylethanamine hydrochloride to afford 2-((benzyloxy)methyl)-N-(5-(6-cyano-5-(((S)-1-((2,2-difluoroethyl)(methyl)amino)-1-oxopropan-2-yl)amino)pyridin-3-yl)pyrazin-2-yl)cyclopropanecarboxamide (0.835 g, 98% yield). ESI-MS: m/z [M+H]+ 550.4.

A mixture of 2-((benzyloxy)methyl)-N-(5-(6-cyano-5-(((S)-1-((2,2-difluoroethyl)(methyl)amino)-1-oxopropan-2-yl)amino)pyridin-3-yl)pyrazin-2-yl)cyclopropanecarboxamide (0.850 g, 1.547 mmol) was dissolved in anhydrous DCM (30.9 mL), purged with nitrogen, and cooled to −78° C. To this a 1M solution of boron trichloride (9.28 mL, 9.28 mmol) was added dropwise. The reaction was stirred at the same temperature for 1 hour, then allowed to warm to room temperature for one hour till completion. The reaction was concentrated in vacuo, re-dissolved in MeOH/DMF (2:3, 10 mL), filtered through a 12 mL fritted syringe with a Millipore™ (Hydrophilic PTFE 0.45 μm) microfilter. The product was purified by preparative HPLC (Sunfire™ C18, 5 μM, ID NH4HCO3) using a gradient of 30-40% ACN with 20/80 (v/v) water/acetonitrile (containing 10 mmol NH4HCO3)] in water (with 10 mmol NH4HCO3) to afford the title compound as a pale yellow solid (187.5 mg, 26.4% yield). 1H NMR (400 MHz, DMSO-d6) δ ppm 0.83-0.95 (m, 1 H) 1.06 (dt, J=8.78, 4.07 Hz, 1H) 1.30-1.43 (m, 3 H) 1.47-1.63 (m, 1 H) 2.00 (dt, J=8.21, 4.23 Hz, 1 H) 3.20-3.32 (m, 4 H) 3.43-3.55 (m, 1 H) 3.79 (td, J=15.22, 3.92 Hz, 2 H) 4.71 (t, J=5.43 Hz, 1 H) 4.87-5.01 (m, 1 H) 5.96-6.31 (m, 2 H) 7.83-7.96 (m, 1 H) 8.65 (d, J=1.52 Hz, 1 H) 9.07-9.16 (m, 1 H) 9.40-9.50 (m, 1 H) 11.27 (s, 1 H). ESI-MS: m/z [M+H]+ 460.3.

EXAMPLE 147

(S)-N-(5-(6-cyano-5-((1-(dimethylamino)-1-oxobutan-2-yl)amino)pyridin-3-yl)pyrazin-2-yl)-3-hydroxy-3-methylcyclobutanecarboxamide

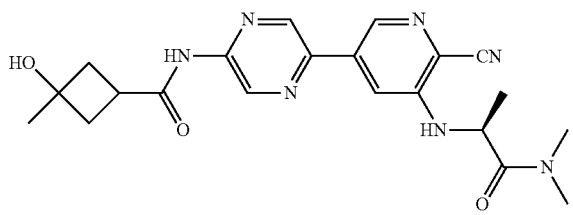 [SMILES: C[C@H](Nc1cc(-c2cnc(NC(=O)C3CC(C)(O)C3)cn2)cnc1C#N)C(=O)N(C)C]

A mixture of 3-hydroxy-3-methylcyclobutanecarboxylic acid (0.748 g, 5.75 mmol) and HATU (3.28 g, 8.62 mmol) were dissolved in anhydrous pyridine (14.37 mL) while under nitrogen. The reaction was stirred at room temperature for 30 minutes, followed by addition of 5-bromopyrazin-2-amine (1 g, 5.75 mmol). The reaction was heated at 55° C. for 12 hours. The residue was purified via normal phase column chromatography on (Thomson™ Single Step 80 g) using a gradient of 20-100% EtOAc/Heptanes on the Teledyne ISCO CombiFlash™ Purification system and dried in vacuo to afford N-(5-bromopyrazin-2-yl)-3-hydroxy-3-methylcyclobutanecarboxamide (2.0467 g) which was used without further purification.

A mixture of Pd(dppf)2 CHCl3 adduct (0.223 g, 0.274 mmol), aqueous cesium carbonate solution (2M, 10.94 mL, 21.89 mmol), N-(5-bromopyrazin-2-yl)-3-hydroxy-3-methylcyclobutanecarboxamide (1.644 g, 5.75 mmol), and 3-fluoro-5-(4,4,5,5-tetramethyl-1,3,2-dioxaborolan-2-yl)picolinonitrile (1.357 g, 5.47 mmol) were dissolved in anhydrous dioxane (18.24 mL). The reaction was heated at 85° C. for 2 hours then cooled. The cooled reaction was diluted into deionized water (200 mL) to give an orange solid which was collected by vacuum filtration through a Kiriyamarohto SB-40 glass funnel while washing with deionized water followed by hexanes to afford N-(5-(6-cyano-5-fluoropyridin-3-yl)pyrazin-2-yl)-3-hydroxy-3-methylcyclobutanecarboxamide (761.8 mg, 42.5% yield).

A mixture of potassium carbonate (63.3 mg, 0.458 mmol), N-(5-(6-cyano-5-fluoropyridin-3-yl)pyrazin-2-yl)-3-hydroxy-3-methylcyclobutanecarboxamide (30 mg, 0.092 mmol), and (S)-2-aminobutanoic acid (95 mg, 0.917 mmol) were dissolved in anhydrous DMSO (229 μl). The reaction was heated at 120° C. for 2 hours. The cooled reaction was diluted into 1N HCl solution (40 mL) to give a brown solid which was collected by vacuum filtration through a Kiriyamarohto SB-21 glass funnel while washing with deionized water followed by hexanes to afford (S)-2-((2-cyano-5-(5-(3-hydroxy-3-methylcyclobutanecarboxamido)pyrazin-2-yl)pyridin-3-yl)amino)butanoic acid (26.9 mg, 71.5% yield).

A mixture of (S)-2-((2-cyano-5-(5-(3-hydroxy-3-methylcyclobutanecarboxamido)pyrazin-2-yl)pyridin-3-yl)amino) butanoic acid (26.9 mg, 0.066 mmol), HATU (29.9 mg, 0.079 mmol) and DIPEA (34.2 μl, 0.197 mmol) were dissolved in anhydrous DMF (164 μl). The reaction was stirred at room temperature for 30 minutes, followed by addition of dimethylamine, HCl (6.41 mg, 0.079 mmol). The reaction continued to stir for 4 hours. The product was purified by preparative HPLC (Sunfire™ C18, 5 μM, ID TFA) using a gradient of 20-80% ACN (with 0.035% TFA) in water (with 0.05% TFA) to afford the title compound as a yellowish orange film (3.3 mg, 11.51% yield). 1H NMR (400 MHz, methanol-d4) δ ppm 0.91 (s, 3 H) 1.19 (br. s., 1 H) 1.23-1.34 (m, 3 H) 1.74 (s, 1 H) 1.85 (br. s., 1 H) 2.18 (br. s., 2 H) 2.28 (br. s., 3 H) 2.83 (br. s., 1 H) 2.89 (s, 2 H) 3.15 (s, 3 H) 7.79 (s, 1 H) 8.49 (br. s., 1 H) 8.84 (br. s., 1 H) 9.44 (br. s., 1 H). ESI-MS m/z [M+H]+ 437.0.

EXAMPLE 148

(S)-N-(5-(6-cyano-5-((1-((2,2-difluoroethyl)(methyl) amino)-1-oxopropan-2-yl)amino)pyridin-3-yl) pyrazin-2-yl)-3-hydroxy-3-methylcyclobutanecarboxamide

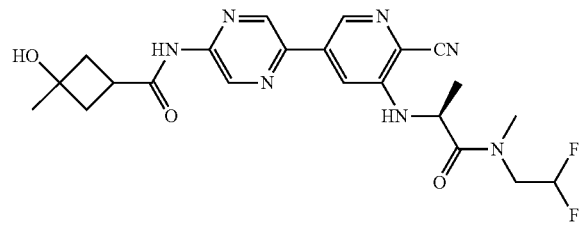 [SMILES: C[C@H](Nc1cc(-c2cnc(NC(=O)C3CC(C)(O)C3)cn2)cnc1C#N)C(=O)N(C)CC(F)F]

The title compound was prepared in a manner similar to Example 147, except 2,2-difluoro-N-methylethanamine, HCl (5.97 mg, 0.045 mmol) was used to afford the title compound as a yellow film (2.6 mg, 14.51% yield). 1H NMR (400 MHz, methanol-d4) δ ppm 1.16-1.28 (m, 3 H) 1.31 (s, 3 H) 1.36-1.45 (m, 4 H) 2.16-2.33 (m, 5 H) 2.83 (t, J=8.46 Hz, 1H) 2.96-3.04 (m, 1 H) 3.24-3.25 (m, 3 H) 3.63-3.78 (m, 2 H) 5.65-6.31 (m, 1 H) 7.67-7.77 (m, 1 H) 8.50 (s, 1 H) 8.73-8.94 (m, 1 H) 9.44 (s, 1 H). ESI-MS m/z [M+H]+ 473.0.

EXAMPLE 149

(S)-N-(5-(6-cyano-5-((1-((2,2-difluoroethyl)(methyl)amino)-1-oxopropan-2-yl)amino)pyridin-3-yl)pyrazin-2-yl)-3-methoxycyclobutanecarboxamide

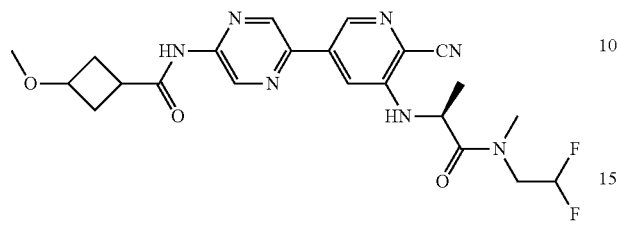

A mixture of 3-methoxycyclobutanecarboxylic acid (180 mg, 1.379 mmol), 5-bromopyrazin-2-amine (200 mg, 1.149 mmol), and pyridine (0.281 mL, 3.45 mmol) were dissolved in anhydrous acetonitrile (1.5 mL). The reaction was stirred at room temperature for 5 minutes, followed by addition of propylphosphonic anhydride solution (50 wt % in EtOAc) (1.367 mL, 2.299 mmol) over the course of 10 minutes. The reaction continued to stir for 12 hours, then the reaction mixture was diluted in deionized water and extracted aqueous with EtOAc (3×). Combined organics and concentrated in vacuo to afford N-(5-bromopyrazin-2-yl)-3-methoxycyclobutanecarboxamide (329 mg, 100% yield).

A mixture of Pd(dppf)2 CHCl3 adduct (44.9 mg, 0.055 mmol), aqueous cesium carbonate solution (2M, 2197 µl, 4.39 mmol), N-(5-bromopyrazin-2-yl)-3-methoxycyclobutanecarboxamide (330 mg, 1.153 mmol), and 3-fluoro-5-(4,4,5,5-tetramethyl-1,3,2-dioxaborolan-2-yl)picolinonitrile (272 mg, 1.098 mmol) were dissolved in anhydrous dioxane (2197 µl). The reaction was heated at 100° C. for 12 hours. The cooled reaction was diluted into deionized water (20 mL) and the orange solid was collected by vacuum filtration through a Kiriyamarohto SB-21 glass funnel while washing with deionized water followed by hexanes to afford N-(5-(6-cyano-5-fluoropyridin-3-yl)pyrazin-2-yl)-3-methoxycyclobutanecarboxamide (378.7 mg) which was used without further purification.

A mixture of potassium carbonate (127 mg, 0.917 mmol), N-(5-(6-cyano-5-fluoropyridin-3-yl)pyrazin-2-yl)-3-methoxycyclobutanecarboxamide (60 mg, 0.183 mmol), and (S)-2-aminopropanoic acid (163 mg, 1.833 mmol) were dissolved in anhydrous DMSO (458 µl). The reaction was heated at 100° C. for one hour. The cooled reaction was diluted into 1N HCl solution (20 mL) to give a brown solid which was collected by vacuum filtration through a Kiriyamarohto SB-21 glass funnel while washing with deionized water followed by hexanes to afford (S)-2-((2-cyano-5-(5-(3-methoxycyclobutanecarboxamido)pyrazin-2-yl)pyridin-3-yl)amino)propanoic acid (25.6 mg, 35.2% yield).

A mixture of (S)-2-((2-cyano-5-(5-(3-methoxycyclobutanecarboxamido)pyrazin-2-yl)pyridin-3-yl)amino)propanoic acid (25.6 mg, 0.065 mmol), HATU (29.5 mg, 0.077 mmol) and DIPEA (33.7 µl, 0.194 mmol) were dissolved in anhydrous DMF (129 µl). The reaction stirred at room temperature for 30 minutes, followed by addition of 2,2-difluoro-N-methylethanamine, HCl (10.19 mg, 0.077 mmol). The reaction continued to stir for 72 hours. The product was purified by preparative HPLC (Sunfire™ C18, 5 µM, ID TFA) using a gradient of 35-60% ACN (with 0.035% TFA) in water (with 0.05% TFA) to afford the title compound as a yellowish orange film (10.7 mg, 35% yield). 1H NMR (400 MHz, DMSO-d6) δ ppm 1.40 (s, 3 H) 2.05 (br. s., 1 H) 2.16 (br. s., 1 H) 2.43 (br. s., 2 H) 2.97 (s, 1 H) 3.15 (s, 3 H) 3.25 (s, 2 H) 3.34 (s, 1 H) 3.81 (d, J=16.17 Hz, 2 H) 3.97 (s, 1 H) 4.03 (s, 1 H) 4.95 (s, 1 H) 6.14 (s, 1 H) 6.29 (br. s., 1 H) 7.88 (s, 1 H) 8.65 (s, 1 H) 9.12 (s, 1 H) 9.49 (br. s., 1 H) 11.01 (s, 1 H). ESI-MS m/z [M+H]+ 473.0.

EXAMPLE 150

(S)-N-(5-(6-cyano-5-((1-((2,2-difluoroethyl)(methyl)amino)-1-oxopropan-2-yl)amino)pyridin-3-yl)pyrazin-2-yl)cyclobutanecarboxamide

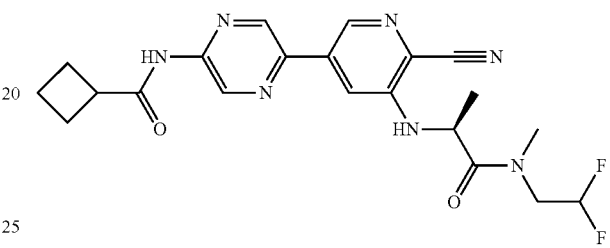

A mixture of 5-bromopyrazin-2-amine (200 mg, 1.149 mmol) was dissolved in anhydrous pyridine (2874 µl) and cooled to 0° C., to which cyclobutanecarbonyl chloride (131 µl, 1.149 mmol) was added dropwise. After 15 minutes diluted in EtOAc and washed with 1N HCl solution (3×). Concentrated in vacuo to afford N-(5-bromopyrazin-2-yl)cyclobutanecarboxamide (294 mg, 100% yield).

A mixture of Pd(dppf)2 CHCl3 adduct (44.6 mg, 0.055 mmol), aqueous cesium carbonate solution (2M, 2187 µl, 4.37 mmol), N-(5-bromopyrazin-2-yl)cyclobutanecarboxamide (294 mg, 1.148 mmol), and 3-fluoro-5-(4,4,5,5-tetramethyl-1,3,2-dioxaborolan-2-yl)picolinonitrile (271 mg, 1.093 mmol) were dissolved in anhydrous dioxane (5467 µl). The reaction was heated at 95° C. for 4 hours. The cooled reaction was diluted into deionized water (40 mL) and the brown solid was collected by vacuum filtration through a Kiriyamarohto SB-60 glass funnel while washing with deionized water followed by hexanes to afford N-(5-(6-cyano-5-fluoropyridin-3-yl)pyrazin-2-yl)cyclobutanecarboxamide (408.5 mg, crude quantitative yield).

A mixture of potassium carbonate (186 mg, 1.346 mmol), N-(5-(6-cyano-5-fluoropyridin-3-yl)pyrazin-2-yl)cyclobutanecarboxamide (80 mg, 0.269 mmol), and (S)-2-aminopropanoic acid (240 mg, 2.69 mmol) were dissolved in anhydrous DMSO (673 µl). The reaction was heated at 120° C. for one hour. The cooled reaction was diluted into 1N HCl solution (20 mL) and the brown solid was collected by vacuum filtration through a Kiriyamarohto SB-21 glass funnel while washing with deionized water followed by hexanes to afford (S)-2-((2-cyano-5-(5-(cyclobutanecarboxamido)pyrazin-2-yl)pyridin-3-yl)amino)propanoic acid (58.8 mg, 59.6% yield).

A mixture of (S)-2-((2-cyano-5-(5-(cyclobutanecarboxamido)pyrazin-2-yl)pyridin-3-yl)amino)propanoic acid (30 mg, 0.082 mmol), HATU (37.4 mg, 0.098 mmol), and DIPEA (42.8 µl, 0.246 mmol) were dissolved in anhydrous DMF (164 µl). The reaction was stirred at room temperature for 30 minutes, followed by addition of 2,2-difluoro-N-methylethanamine, HCl (12.93 mg, 0.098 mmol). The reaction continued to stir for 4 hours. The product was purified by preparative HPLC (Sunfire™ C18, 5 µM, ID TFA) using a gradient of 35-65% ACN (with 0.035% TFA) in water (with 0.05% TFA) to afford the title compound as a pale, yellow film (10.8 mg, 29.7% yield). 1H NMR (500 MHz, DMSO-d6) δ ppm 1.39 (s, 3 H) 1.81 (br. s., 1 H) 1.96 (s, 1 H) 2.13 (br. s., 2 H) 2.25 (br. s., 2 H) 2.96 (s, 1 H) 3.24 (s, 2 H) 3.43 (s, 1 H) 3.75-3.85 (m, 2 H) 4.93 (br. s., 1 H) 6.15 (br. s., 1 H) 6.26 (br. s., 1 H) 7.87 (s, 1 H) 8.65 (s, 1 H) 9.11 (s, 1 H) 9.50 (s, 1 H) 10.87 (s, 1 H). ESI-MS m/z [M+H]+ 443.0.

The compounds of the invention can be administered alone or in the form of a pharmaceutical composition. In practice, the compounds of the invention are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, the present invention provides pharmaceutical compositions comprising: a compound of invention and at least one pharmaceutically acceptable excipient.

In effecting treatment of a patient in need of such treatment, a compound of the invention can be administered in any form and route which makes the compound bioavailable. The compounds of the invention can be administered by a variety of routes, including orally, in particularly by tablets and capsules. The compounds of the invention can be administered parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the invention may be varied depending upon its particular form and may conveniently be between 1% to about 50% of the weight of the unit dose form. The term "pharmaceutically acceptable excipient" refers to those typically used in preparing pharmaceutical compositions and should be pharmaceutically pure and non-toxic in the amounts used. They generally are a solid, semi-solid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dose form, each dose typically containing from about 0.5 mg to about 100 mg of a compounds of the invention. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage, typically on a daily schedule.

In one particular variation, the composition is a pharmaceutical composition adapted for oral administration, such as a tablet or a capsule or a liquid formulation, for example, a solution or suspension, adapted for oral administration. In still another particular variation, the pharmaceutical composition is a liquid formulation adapted for parenteral administration.

In another embodiment, the invention provides methods of treating conditions associated with TBK1, comprising: administering to a patient in need thereof an effective amount of a compound of the invention. In another embodiment, a compound of the invention is provided for use as a medicament. The invention also provides the use of a compound of the invention, including the use for the manufacture of a medicament, to treat the conditions associated with TBK1 described herein. The compounds of the invention are useful as TBK1 inhibitors for a variety of subjects (e.g., humans, non-human mammals and non-mammals).

As used herein terms "condition," "disorder," and "disease" relate to any unhealthy or abnormal state. The term "conditions associated with TBK1" includes conditions, disorders, and diseases in which the inhibition of TBK1 provides a therapeutic benefit, such as immunological disorders, inflammatory disorders, and abnormal cell growth, such as cancer.

The term "conditions associated with TBK1" includes specifically, but is not limited to, autoimmune disorders and conditions include lupus, particularly systemic lupus erythematosus and chilblain lupus, Crohn's disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, Sjögren's syndrome, temporal arteritis, ulcerative colitis, vasculitis, and Wegener's granulomatosis, among others.

Furthermore, the term "conditions associated with TBK1" includes specifically, but is not limited to, inflammatory disorders including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemic inflammatory response syndrome.

The term "conditions associated with TBK1" includes specifically, includes specific diseases that may fall within one or more general category described above, such as arthritis, including rheumatoid arthritis, and other arthritis diseases, including ankylosing spondylitis, avascular necrosis, Bechet's disease, bursitis, calcium pyrophosphate dihydrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, among others.

The term "conditions associated with TBK1" includes specifically, fibrotic diseases of the lungs, kidneys, eyes, heart, liver, and skin, including pulmonary fibrosis, idiopathic pulmonary fibrosis, idiopathic interstitial pneumonias, desquamative pulmonary fibrosis, cryptogenic organizing pneumonia, acute interstitial pneumonia, non-specific interstitial pneumonia, respiratory bronchiolitis associated with interstitial lung disease, cryptogenic organizing pneumonia, lymphocytic interstitial pneumonia, chronic kidney disease, diabetic kidney disease, chronic liver disease, keloidal scarring, and nephrogenic systemic fibrosis.

The term "conditions associated with TBK1" includes specifically, but is not limited to, cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the term "conditions associated with TBK1" includes specifically other diseases related to abnormal cell growth, including non-malignant proliferative diseases such as benign prostatic hypertrophy, restenosis, hyperplasia, synovial proliferation disorder, retinopathy or other neovascular disorders of the eye, among others.

The term "conditions associated with TBK1" includes specifically, but is not limited to, sepsis, septic shock, virally or bacterially induced diseases or infections, mycobateria-induced infections (including opportunistic infections), rejection of transplanted tissues, psoriasis, hemangiomas, diseases with disturbed angiogenesis, especially ischemic or dental diseases, smoker's leg and diabetic ulcers, retinal vasculopathy and cerebral leukodystrophy, systemic sclerosis, glomerulonephritis, dermatomyositis, polymyositis chronic obstructive pulmonary disease, mediating insulin resistance, including as part of the metabolic syndrome, type 2 diabetes mellitus, diabetic dislipidemia, conditions of impaired glucose tolerance, conditions of impaired fasting plasma glucose, metabolic acidosis, ketosis, and appetite regulation, prion diseases, polycystic ovary syndrome, and primary biliary cirrhosis.

In particularly, the term "conditions associated with TBK1" includes primary biliary cirrhosis, ulcerative colitis, and lupus, particularly systemic lupus erythematosus.

The terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present invention, the treatment dosage, is expected to range from 1 mg to 200 mg. Specific amounts can be determined by the skilled person. Although these dosages are based on an average human subject having a mass of about 60 kg to about 70 kg, the physician will be able to determine the appropriate dose for a patient (e.g., an infant) whose mass falls outside of this weight range.

The compounds of the invention may be combined with one or more other pharmacologically active compounds or therapies for the treatment of one or more disorders, diseases or conditions for which TBK1 is indicated may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, a compound of the invention may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, a compound of the invention may be combined with one or more disease modifying antirheumatic drugs (DMARDs), and when treating osteoarthritis, the compounds of formula 1 may be combined with one or more osteoporosis agents.

Particularly useful combinations for treating rheumatoid arthritis include a compound of the invention and methotrexate; a compound of the invention and one or more biological response modifiers, such as lefluonomide, etanercept, adalimumab, and infliximab; or a compound of the invention, methotrexate, and one or more biological response modifiers, such as lefluonomide, etanercept, adalimumab, and infliximab.

The activity of compounds as TBK1 inhibitors may be determined by a variety of methods, including in vitro and in vivo methods.

EXAMPLE A Inhibition of TBK1 Enzyme

Full length human TBK1 with an N-terminal His-tag was cloned into the pFastBacl vector and was transfected into Sf9 cells. 72 hours later the virus was harvested and amplified through two additional rounds of infections. Then 400 mL of the resulting virus stock was used to infect 10 L of Sf9 cells at a density of 2×106 cells/mL. Cell pellets were harvested 48 hours post infection and were lysed by freeze-thaw, homogenization and sonication in binding buffer (25 mM Tris pH7.6, 1 M NaCl, 10 mM imidazole, 0.5 mM TCEP) plus 0.1% Triton X-100 and complete protease inhibitor cocktail. The lysate was spun and the supernatant was purified with a HisTrap FF crude and a Superdex 200 pg column.

TBK1 inhibition is determined using a 384 well μlate format in buffer containing 20 mM Hepes, pH 7.4, 10 mM MgCl2, 1 mM EDTA, 0.01% Brij-L23, 1 mM DTT. Each test compound is prepared in DMSO using 2.5-fold serial dilutions for 11 data points, which are added to the buffer so that each dilution contains 1% DMSO. To each well is added 2 μL of 1 μM 5FAM-DRHDSGLDSMKDE-NH2 (in buffer), 2 μL of diluted test compound (1% DMSO in buffer), and 5 μL of 3 nM TBK1 and 25 μM ATP (in buffer). The reaction mixture is incubated at RT for 60 min, and quenched by adding 20 mM Hepes, pH 7.4, 10 mM MgCl2, 1 mM EDTA, 0.01% Brij-L23, 1 mM DTT+25 mM EDTA. To quantify the fluorescent-labeled substrate and product following reaction, the test plate is loaded on a Caliper LC-3000, which measures percent of conversion by microfluidic-based separation. Corresponding $IC_{50}$ values are calculated by non-linear curve fitting of the compound concentrations and percent of inhibition to the standard $IC_{50}$ equation and reported as $pIC_{50}$, i.e., $-\log(IC_{50})$, where $IC_{50}$ is the molar concentration.

Table A provides results for exemplified compounds in Example A.

TABLE A

TBK1 Inhibition ($pIC_{50}$) for Example (Ex) Compounds

| EX | $pIC_{50}$ | EX | $pIC_{50}$ | EX | $pIC_{50}$ | EX | $pIC_{50}$ | EX | $pIC_{50}$ |
|---|---|---|---|---|---|---|---|---|---|
| 1 | 8.1 | 2 | 7.1 | 3.0 | 7.9 | 4.0 | 7.1 | 5 | 7.3 |
| 6 | 8.1 | 7 | 8.2 | 8.0 | 8.1 | 9.0 | 6.7 | 10 | 7.3 |
| 11 | 6.7 | 12 | 8.0 | 13 | 6.3 | 14 | 6.9 | 15 | 5.8 |
| 16 | 6.3 | 17 | 7.1 | 18 | 7.5 | 19 | 7.7 | 20 | 7.4 |
| 21 | 6.6 | 22 | 6.0 | 23 | 7.7 | 24 | 6.8 | 25 | 7.4 |
| 26 | 8.5 | 27 | 6.9 | 28 | 6.9 | 29 | 7.8 | 30 | 5.8 |
| 31 | 6.3 | 32 | 6.8 | 33 | 5.9 | 34 | 8.2 | 35 | 6.9 |
| 36 | 7.3 | 37 | 6.9 | 38 | 5.8 | 39 | 7.0 | 40 | 7.5 |
| 41 | 7.8 | 42 | 6.8 | 43 | 7.7 | 44 | 6.2 | 45 | 7.5 |
| 46 | 8.0 | 47 | 7.7 | 48 | 8.2 | 49 | 7.2 | 50 | 7.9 |
| 51 | 7.4 | 52 | 6.5 | 53 | 8.6 | 54 | 8.0 | 55 | 7.6 |
| 56 | 7.7 | 57 | 7.2 | 58 | 7.3 | 59 | 6.7 | 60 | 7.4 |
| 61 | 6.0 | 62 | 6.6 | 63 | 7.2 | 64 | 7.5 | 65 | 6.9 |
| 66 | 6.6 | 67 | 6.3 | 68 | 7.4 | 69 | 7.7 | 70 | 7.1 |
| 71 | 6.6 | 72 | 7.8 | 73 | 7.0 | 74 | 5.5 | 75 | 6.9 |
| 76 | 5.3 | 77 | 7.2 | 78 | 6.6 | 79 | 6.8 | 80 | 7.4 |
| 81 | 7.8 | 82 | 7.8 | 83 | 7.0 | 84 | 7.2 | 85 | 7.1 |
| 86 | 8.4 | 87 | 7.2 | 88 | 7.6 | 89 | 7.9 | 90 | 5.6 |
| 91 | 7.7 | 92 | 6.2 | 93 | 6.8 | 94 | 7.3 | 95 | 6.2 |
| 96 | 7.8 | 97 | 5.5 | 98 | 5.1 | 99 | 6.0 | 100 | 6.5 |
| 101 | 6.7 | 102 | 6.6 | 103 | 6.8 | 104 | 5.4 | 105 | 5.6 |
| 106 | 7.4 | 107 | 7.8 | 108 | 7.7 | 109 | 7.2 | 110 | 7.5 |
| 111 | 6.6 | 112 | 7.7 | 113 | 7.6 | 114 | 7.7 | 115 | 6.9 |

TABLE A-continued

TBK1 Inhibition ($pIC_{50}$) for Example (Ex) Compounds

| EX | $pIC_{50}$ | EX | $pIC_{50}$ | EX | $pIC_{50}$ | EX | $pIC_{50}$ | EX | $pIC_{50}$ |
|---|---|---|---|---|---|---|---|---|---|
| 116 | 7.3 | 117 | 7.0 | 118 | 6.8 | 119 | 8.1 | 120 | 7.2 |
| 121 | 5.6 | 122 | 7.0 | 123 | 7.2 | 124 | 6.5 | 125 | 7.3 |
| 126 | 7.6 | 127 | 7.0 | 128 | 7.1 | 129 | 7.6 | 130 | 7.1 |
| 131 | 7.1 | 132 | 6.2 | 133 | 7.3 | 134 | 6.9 | 135 | 7.7 |
| 136 | 7.6 | 137 | 7.6 | 138 | 6.2 | 139 | 7.7 | 140 | 7.0 |
| 141 | 8.3 | 142 | 7.2 | 143 | 7.0 | 144 | 5.6 | 145 | 7.1 |
| 146 | 8.1 | 147 | 6.4 | 148 | 7.1 | 149 | 7.5 | 150 | 7.8 |

EXAMPLE B Inhibition of ConA Induced Hepatitis

Orally administer compound into normal C57/BL6 mice at several doses. After 1 hr, inject i.v. with ConA 15 mg/kg, (N=5). Post 8-24 hrs, collect plasma and liver. Measure plasma ALT enzyme level. An $ED_{50}$ is determined as the amount of test compound that reduces ConA induced increase in plasma ALT level by 50%.

In the assay of Example C, the compound of Example 1 gave $ED_{50}$=5 mg/kg.

What is claimed is:

1. A compound of formula 1:

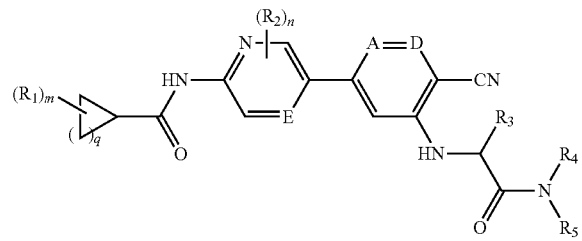

or a pharmaceutically acceptable salt thereof, wherein
m is selected from 0, 1, and 2;
n is selected from 0, 1, and 2;
q is selected from 1, 2, and 3;
$R_1$, each time taken, is independently selected from the group consisting of fluoro, hydroxymethyl, and $C_{1-4}$ alkyl;
$R_2$, each time taken, is independently selected from the group consisting of cyano, halo, hydroxy, amino, $C_{1-4}$ alkyl, $C_{1-4}$ alkoxy, hydroxymethyl, and trifluoromethyl;
$R_3$ is selected from the group consisting of hydrogen and optionally substituted $C_{1-4}$ alkyl;
$R_4$ is selected from the group consisting of hydrogen and optionally substituted $C_{1-4}$ alkyl;
$R_5$ is selected from the group consisting of hydrogen, optionally substituted $C_{1-6}$ alkyl, optionally substituted $C_{3-8}$ cycloalkyl, optionally substituted $C_{1-10}$ heteroaryl, and optionally substituted $C_{3-6}$ heterocyclyl;
or
$R_4$ and $R_5$ together with the nitrogen to which they are attached form a 4 to 8 membered, saturated, monocyclic or bicyclic ring optionally having an additional ring heteroatom selected from the group N, O, and $S(O)_p$ wherein p is selective from 0, 1, and 2 and optionally substituted on ring carbons with 1 to 5 substituents independently selected from the group consisting of cyano, halo, hydroxy, amino, $C_{1-9}$ amide, $C_{1-4}$ alkyl, $C_{1-4}$ alkoxy, hydroxymethyl, fluoromethyl, difluoromethyl, and trifluoromethyl and any additional ring nitrogen is optionally substituted with a substituent selected from the group consisting of hydrogen, —C(O)—C$_{1-4}$ alkyl and optionally substituted C$_{1-4}$ alkyl;

E is selected from the group consisting of N and CR$_2$;
A is selected from the group consisting of N and CR$_6$;
D is selected from the group consisting of N and CR$_7$;
R$_6$ is selected from the group consisting of hydrogen, cyano, halo, C$_{1-4}$ alkyl, C$_{1-4}$ alkoxy, and trifluoromethyl; and
R$_7$ is selected from the group consisting of hydrogen, cyano, halo, C$_{1-4}$ alkyl, C$_{1-4}$ alkoxy, and trifluoromethyl.

2. The compound or pharmaceutically acceptable salt according to claim 1, wherein the compound is substantially enantiomerically pure and has the following configuration:

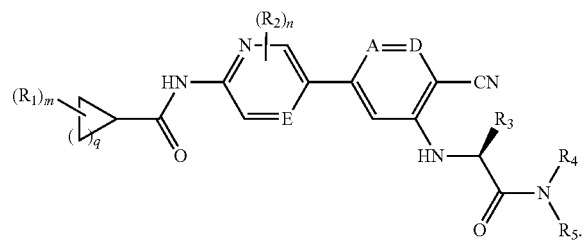

3. The compound or pharmaceutically acceptable salt according to claim 1, wherein m is 0.
4. The compound or pharmaceutically acceptable salt according to claim 1, wherein m is 1 and R$_1$ is methyl.
5. The compound or pharmaceutically acceptable salt according to claim 1, wherein n is 0.
6. The compound or pharmaceutically acceptable salt according to claim 1, wherein q is 1.
7. The compound or pharmaceutically acceptable salt according to claim 1, wherein E is N.
8. The compound or pharmaceutically acceptable salt according to claim 1, wherein R$_3$ is hydrogen.
9. The compound or pharmaceutically acceptable salt according to claim 1, wherein R$_3$ is C$_{1-4}$ alkyl.
10. The compound or pharmaceutically acceptable salt according to claim 1, wherein R$_4$ is hydrogen.
11. The compound or pharmaceutically acceptable salt according to claim 1, wherein R$_4$ is C$_{1-4}$ alkyl.
12. The compound or pharmaceutically acceptable salt according to claim 1, wherein R$_5$ is optionally substituted C$_{1-6}$ alkyl.
13. The compound or pharmaceutically acceptable salt according to claim 1, wherein R$_5$ is C$_{1-6}$ alkyl.
14. The compound according to claim 1, which is selected from the following compounds:

N-(5-(4-cyano-3-((2-(dimethylamino)-2-oxoethyl)amino)phenyl)pyrazin-2-yl)-2-methylcyclopropanecarboxamide;
N-(5-(4-cyano-3-((2-(ethyl(methyl)amino)-2-oxoethyl)amino)phenyl)pyrazin-2-yl)cyclopropanecarboxamide;
N-(5-(3-((2-(azetidin-1-yl)-2-oxoethyl)amino)-4-cyanophenyl)pyrazin-2-yl)cyclopropanecarboxamide;
N-(5-(4-cyano-3-((2-(3-methoxyazetidin-1-yl)-2-oxoethyl)amino)phenyl)pyrazin-2-yl)cyclopropanecarboxamide;
N-(5-(4-cyano-3-((2-(3,3-difluoroazetidin-1-yl)-2-oxoethyl)amino)phenyl)pyrazin-2-yl)cyclopropanecarboxamide;
N-(5-(4-cyano-3-((2-(cyclopropyl(methyl)amino)-2-oxoethyl)amino)phenyl)pyrazin-2-yl)cyclopropanecarboxamide;
N-(5-(4-cyano-3-((2-(3-hydroxypyrrolidin-1-yl)-2-oxoethyl)amino)phenyl)pyrazin-2-yl)cyclopropanecarboxamide;
N-(5-(6-cyano-5-((2-(methyl(2,2,2-trifluoroethyl)amino)-2-oxoethyl)amino)pyridin-3-yl)pyrazin-2-yl)cyclopropanecarboxamide;
N-(5-(6-cyano-5-((2-(2-cyanopyrrolidin-1-yl)-2-oxoethyl)amino)pyridin-3-yl)pyrazin-2-yl)cyclopropanecarboxamide;
(N-(5-(6-cyano-5-((2-oxo-2-(2-(trifluoromethyl)pyrrolidin-1-yl)ethyl)amino)pyridin-3-yl)pyrazin-2-yl)cyclopropanecarboxamide;
N-(5-(6-cyano-5-((2-((cyanomethyl)(methyl)amino)-2-oxoethyl)amino)pyridin-3-yl)pyrazin-2-yl)cyclopropanecarboxamide;
N-(5-(6-cyano-5-((2-((1-cyanoethyl)amino)-2-oxoethyl)amino)pyridin-3-yl)pyrazin-2-yl)cyclopropanecarboxamide;
N-(5-(6-cyano-5-((2-(3-cyanomorpholino)-2-oxoethyl)amino)pyridin-3-yl)pyrazin-2-yl)cyclopropanecarboxamide;
N-(5-(6-cyano-5-(2-oxo-2-(2-(trifluoromethyl)oxazolidin-3-yl)ethyl)amino)pyridin-3-yl)pyrazin-2-yl)cyclopropanecarboxamide;
N-(5-(6-cyano-5-((2-((2-cyanoethyl)(methyl)amino)-2-oxoethyl)amino)pyridin-3-yl)pyrazin-2-yl)cyclopropanecarboxamide;
N-(5-(6-cyano-5-((2-(methyl(2-(methylsulfonyl)ethyl)amino)-2-oxoethyl)amino)pyridin-3-yl)pyrazin-2-yl)cyclopropanecarboxamide;
N-(5-(6-cyano-5-((2-(methyl(tetrahydrofuran-3-yl)amino)-2-oxoethyl)amino)pyridin-3-yl)pyrazin-2-yl)cyclopropanecarboxamide;
N-(5-(6-cyano-5-((2-((2,2-difluoroethyl)(2-hydroxyethyl)amino)-2-oxoethyl)amino)pyridin-3-yl)pyrazin-2-yl)cyclopropanecarboxamide;
N-(5-(6-cyano-5-((2-(3-(fluoromethyl)morpholino)-2-oxoethyl)amino)pyridin-3-yl)pyrazin-2-yl)cyclopropanecarboxamide;
N-(5-(6-cyano-5-((2-(methyl(pyrazin-2-ylmethyl)amino)-2-oxoethyl)amino)pyridin-3-yl)pyrazin-2-yl)cyclopropanecarboxamide;
N-(5-(6-cyano-5-((2-((2-methoxyethyl)(2,2,2-trifluoroethyl)amino)-2-oxoethyl)amino)pyridin-3-yl)pyrazin-2-yl)cyclopropanecarboxamide;
N-(5-(6-cyano-5-((2-((2,2-difluoroethyl)(2-methoxyethyl)amino)-2-oxoethyl)amino)pyridin-3-yl)pyrazin-2-yl)cyclopropanecarboxamide;
N-(5-(6-cyano-5-((2-(3-methylmorpholino)-2-oxoethyl)amino)pyridin-3-yl)pyrazin-2-yl)cyclopropanecarboxamide;
N-(5-(6-cyano-5-((2-((cyanomethyl)(2-hydroxyethyl)amino)-2-oxoethyl)amino)pyridin-3-yl)pyrazin-2-yl)cyclopropanecarboxamide;
N-(5-(6-cyano-5-((2-((3-hydroxypropyl)(2,2,2-trifluoroethyl)amino)-2-oxoethyl)amino)pyridin-3-yl)pyrazin-2-yl)cyclopropanecarboxamide;
N-(5-(6-cyano-5-((2-((1-cyanopropyl)(methyl)amino)-2-oxoethyl)amino)pyridin-3-yl)pyrazin-2-yl)cyclopropanecarboxamide;
N-(5-(6-cyano-5-((2-oxo-2-(2-(trifluoromethyl)azetidin-1-yl)ethyl)amino)pyridin-3-yl)pyrazin-2-yl)cyclopropanecarboxamide;

N-(5-(6-cyano-5-((2-oxo-2-(2-(trifluoromethyl)oxazolidin-3-yl)ethyl)amino)pyridin-3-yl)pyrazin-2-yl)cyclopropanecarboxamide;
N-(5-(6-cyano-5-((2-(4-methylpiperazin-1-yl)-2-oxoethyl)amino)pyridin-3-yl)pyrazin-2-yl)cyclopropanecarboxamide;
N-(5-(6-cyano-5-((2-(4-(2-methoxyethyl)piperazin-1-yl)-2-oxoethyl)amino)pyridin-3-yl)pyrazin-2-yl)cyclopropanecarboxamide;
N-(5-(5-((2-(4-acetylpiperazin-1-yl)-2-oxoethyl)amino)-6-cyanopyridin-3-yl)pyrazin-2-yl)cyclopropanecarboxamide;
N-(5-(6-cyano-5-((2-oxo-2-(2-(trifluoromethyl)morpholino)ethyl)amino)pyridin-3-yl)pyrazin-2-yl)cyclopropanecarboxamide;
(R)-N-(5-(6-cyano-5-((2-oxo-2-(3-(trifluoromethyl)morpholino)ethyl)amino)pyridin-3-yl)pyrazin-2-yl)cyclopropanecarboxamide;
N-(5-(6-cyano-5-((2-(3-cyanopyrrolidin-1-yl)-2-oxoethyl)amino)pyridin-3-yl)pyrazin-2-yl)cyclopropanecarboxamide;
N-(5-(6-cyano-5-((2-(2-methylmorpholino)-2-oxoethyl)amino)pyridin-3-yl)pyrazin-2-yl)cyclopropanecarboxamide;
N-(5-(6-cyano-5-((2-oxo-2-(2-oxa-6-azaspiro[3.3]heptan-6-yl)ethyl)amino)pyridin-3-yl)pyrazin-2-yl)cyclopropanecarboxamide;
N-(5-(6-cyano-5-((2-(methyl(1-methylazetidin-3-yl)amino)-2-oxoethyl)amino)pyridin-3-yl)pyrazin-2-yl)cyclopropanecarboxamide;
N-(5-(6-cyano-5-((2-((2-hydroxypropyl)(2,2,2-trifluoroethyl)amino)-2-oxoethyl)amino)pyridin-3-yl)pyrazin-2-yl)cyclopropanecarboxamide;
N-(5-(6-cyano-5-((2-((2-hydroxy-2-methylpropyl)(2,2,2-trifluoroethyl)amino)-2-oxoethyl)amino)pyridin-3-yl)pyrazin-2-yl)cyclopropanecarboxamide;
N-(5-(6-cyano-5-((2-((4-(hydroxymethyl)-2-(trifluoromethyl)pyrrolidin-1-yl)-2-oxoethyl)amino)pyridin-3-yl)pyrazin-2-yl)cyclopropanecarboxamide;
N-(5-(5-((2-amino-2-oxoethyl)amino)-6-cyanopyridin-3-yl)pyrazin-2-yl)cyclopropanecarboxamide;
N-(5-(6-cyano-5-((2-(dimethylamino)-2-oxoethyl)amino)pyridin-3-yl)pyrazin-2-yl)cyclopropanecarboxamide;
N-(5-(4-cyano-3-((2-(dimethylamino)-2-oxoethyl)amino)phenyl)pyrazin-2-yl)cyclopropanecarboxamide;
N-(5-(4-cyano-3-((2-(ethylamino)-2-oxoethyl)amino)phenyl)pyrazin-2-yl)cyclopropanecarboxamide;
N-(5-(4-cyano-3-((2-oxo-2-(pyrrolidin-1-yl)ethyl)amino)phenyl)pyrazin-2-yl)cyclopropanecarboxamide;
N-(5-(4-cyano-3-((2-(methyl(2,2,2-trifluoroethyl)amino)-2-oxoethyl)amino)phenyl)pyrazin-2-yl)cyclopropanecarboxamide;
N-(5-(4-cyano-3-((2-((2-hydroxyethyl)(methyl)amino)-2-oxoethyl)amino)phenyl)pyrazin-2-yl)cyclopropanecarboxamide;
N-(5-(4-cyano-3-((2-(3-hydroxy-3-methylpyrrolidin-1-yl)-2-oxoethyl)amino)phenyl)pyrazin-2-yl)cyclopropanecarboxamide;
N-(5-(4-cyano-3-((2-((1-hydroxypropan-2-yl)(methyl)amino)-2-oxoethyl)amino)phenyl)pyrazin-2-yl)cyclopropanecarboxamide;
N-(5-(4-cyano-3-((2-((2-hydroxypropyl)(methyl)amino)-2-oxoethyl)amino)phenyl)pyrazin-2-yl)cyclopropanecarboxamide;
N-(5-(6-cyano-5-((2-(1,1-dioxidothiazolidin-3-yl)-2-oxoethyl)amino)pyridin-3-yl)pyrazin-2-yl)cyclopropanecarboxamide;
N-(5-(6-cyano-5-((2-(3,3-difluoropyrrolidin-1-yl)-2-oxoethyl)amino)pyridin-3-yl)pyrazin-2-yl)cyclopropanecarboxamide;
N-(5-(6-cyano-5-((2-(2-(fluoromethyl)pyrrolidin-1-yl)-2-oxoethyl)amino)pyridin-3-yl)pyrazin-2-yl)cyclopropanecarboxamide;
N-(5-(5-((2-amino-2-oxoethyl)amino)-6-cyanopyridin-3-yl)pyrazin-2-yl)-2-methylcyclopropanecarboxamide;
N-(5-(6-cyano-5-((2-(dimethylamino)-2-oxoethyl)amino)pyridin-3-yl)pyrazin-2-yl)-2-methylcyclopropanecarboxamide; and a pharmaceutically acceptable salt of any one of the above-mentioned compounds.

15. The compound according to claim 1, which is selected from the following compounds:
N-(5-(4-cyano-3-((1-(dimethylamino)-1-oxopropan-2-yl)amino)phenyl)pyrazin-2-yl)cyclopropanecarboxamide;
N-(5-(4-cyano-3-((1-(dimethylamino)-3-methyl-1-oxobutan-2-yl)amino)phenyl)pyrazin-2-yl)cyclopropanecarboxamide;
N-(5-(4-cyano-3-((1-(dimethylamino)-1-oxobutan-2-yl)amino)phenyl)pyrazin-2-yl)cyclopropanecarboxamide;
N-(5-(4-cyano-3-((1-(dimethylamino)-4-methoxy-1-oxobutan-2-yl)amino)phenyl)pyrazin-2-yl)cyclopropanecarboxamide;
N-(5-(4-cyano-3-((1-(dimethylamino)-4,4-difluoro-1-oxobutan-2-yl)amino)phenyl)pyrazin-2-yl)cyclopropanecarboxamide;
N-(5-(3-((1-(azetidin-1-yl)-1-oxopropan-2-yl)amino)-4-cyanophenyl)pyrazin-2-yl)cyclopropanecarboxamide;
N-(5-(4-cyano-3-((1-oxo-1-(pyrrolidin-1-yl)propan-2-yl)amino)phenyl)pyrazin-2-yl)cyclopropanecarboxamide;
N-(5-(4-cyano-3-((1-(3-hydroxyazetidin-1-yl)-1-oxopropan-2-yl)amino)phenyl)pyrazin-2-yl)cyclopropanecarboxamide;
N-(5-(4-cyano-3-((1-(ethyl(methyl)amino)-1-oxopropan-2-yl)amino)phenyl)pyrazin-2-yl)cyclopropanecarboxamide;
N-(5-(4-cyano-3-((1-((2-hydroxyethyl)amino)-1-oxopropan-2-yl)amino)phenyl)pyrazin-2-yl)cyclopropanecarboxamide;
N-(5-(4-cyano-3-((1-(isopropylamino)-1-oxopropan-2-yl)amino)phenyl)pyrazin-2-yl)cyclopropanecarboxamide;
N-(5-(4-cyano-3-((1-((2-methoxyethyl)amino)-1-oxopropan-2-yl)amino)phenyl)pyrazin-2-yl)cyclopropanecarboxamide;
N-(5-(4-cyano-3-((1-(3-methoxyazetidin-1-yl)-1-oxopropan-2-yl)amino)phenyl)pyrazin-2-yl)cyclopropanecarboxamide;
N-(5-(4-cyano-3-((1-((2-methoxyethyl)(methyl)amino)-1-oxopropan-2-yl)amino)phenyl)pyrazin-2-yl)cyclopropanecarboxamide;
N-(5-(4-cyano-3-((1-(dimethylamino)-3-hydroxy-1-oxopropan-2-yl)amino)phenyl)pyrazin-2-yl)cyclopropanecarboxamide;
N-(5-(4-cyano-3-((1-((2-hydroxyethyl)(methyl)amino)-1-oxopropan-2-yl)amino)phenyl)pyrazin-2-yl)cyclopropanecarboxamide;
N-(5-(4-cyano-3-((1-(dimethylamino)-4-hydroxy-1-oxobutan-2-yl)amino)phenyl)pyrazin-2-yl)cyclopropanecarboxamide;
N-(5-(4-cyano-3-((1-((2-hydroxyethyl)(methyl)amino)-1-oxobutan-2-yl)amino)phenyl)pyrazin-2-yl)cyclopropanecarboxamide;

N-(5-(6-cyano-5-((1-(dimethylamino)-3-hydroxy-1-oxobutan-2-yl)amino)pyridin-3-yl)pyrazin-2-yl)cyclopropanecarboxamide;

N-(5-(6-cyano-5-((1-((2-hydroxyethyl)(methyl)amino)-1-oxobutan-2-yl)amino)pyridin-3-yl)pyrazin-2-yl)cyclopropanecarboxamide;

N-(5-(6-cyano-5-((1-(cyclopropyl(methyl)amino)-1-oxobutan-2-yl)amino)pyridin-3-yl)pyrazin-2-yl)cyclopropanecarboxamide;

N-(5-(6-cyano-5-((1-(methyl(2,2,2-trifluoroethyl)amino)-1-oxopropan-2-yl)amino)pyridin-3-yl)pyrazin-2-yl)cyclopropanecarboxamide;

N-(5-(6-cyano-5-((1-(dimethylamino)-3-methoxy-1-oxopropan-2-yl)amino)pyridin-3-yl)pyrazin-2-yl)cyclopropanecarboxamide;

N-(5-(6-cyano-5-((1-((cyanomethyl)(methyl)amino)-1-oxopropan-2-yl)amino)pyridin-3-yl)pyrazin-2-yl)cyclopropanecarboxamide;

N-(5-(6-cyano-5-((3-cyano-1-(dimethylamino)-1-oxopropan-2-yl)amino)pyridin-3-yl)pyrazin-2-yl)cyclopropanecarboxamide;

N-(5-(6-cyano-5-((1-((2,2-difluoroethyl)(methyl)amino)-1-oxopropan-2-yl)amino)pyridin-3-yl)pyrazin-2-yl)cyclopropanecarboxamide;

N-(5-(6-cyano-5-((1-((2-fluoroethyl)(methyl)amino)-1-oxopropan-2-yl)amino)pyridin-3-yl)pyrazin-2-yl)cyclopropanecarboxamide;

(N-(5-(6-cyano-5-((2-oxo-2-(2-(trifluoromethyl)pyrrolidin-1-yl)ethyl)amino)pyridin-3-yl)pyrazin-2-yl)cyclopropanecarboxamide;

N-(5-(6-cyano-5-((1-((cyanomethyl)(methyl)amino)-1-oxobutan-2-yl)amino)pyridin-3-yl)pyrazin-2-yl)cyclopropanecarboxamide;

N-(5-(6-cyano-5-((1-((2-hydroxyethyl)(methyl)amino)-4-methoxy-1-oxobutan-2-yl)amino)pyridin-3-yl)pyrazin-2-yl)cyclopropanecarboxamide;

N-(5-(6-cyano-5-(((S)-1-((R)-2-cyanopyrrolidin-1-yl)-1-oxopropan-2-yl)amino)pyridin-3-yl)pyrazin-2-yl)cyclopropanecarboxamide;

N-(5-(6-cyano-5-((1-((2-fluoroethyl)(methyl)amino)-1-oxobutan-2-yl)amino)pyridin-3-yl)pyrazin-2-yl)cyclopropanecarboxamide;

N-(5-(6-cyano-5-((1-((2,2-difluoroethyl)(methyl)amino)-3-hydroxy-1-oxopropan-2-yl)amino)pyridin-3-yl)pyrazin-2-yl)cyclopropanecarboxamide;

N-(5-(6-cyano-5-(1-oxo-1-(2-(trifluoromethyl)oxazolidin-3-yl)propan-2-ylamino)pyridin-3-yl)pyrazin-2-yl)cyclopropanecarboxamide;

N-(5-(6-cyano-5-(1-oxo-1-(2-(trifluoromethyl)oxazolidin-3-yl)propan-2-ylamino)pyridin-3-yl)pyrazin-2-yl)cyclopropanecarboxamide;

N-(5-(6-cyano-5-((1-((1-cyanoethyl)amino)-1-oxopropan-2-yl)amino)pyridin-3-yl)pyrazin-2-yl)cyclopropanecarboxamide;

N-(5-(6-cyano-5-((1-((2-(dimethylamino)ethyl)(methyl)amino)-1-oxopropan-2-yl)amino)pyridin-3-yl)pyrazin-2-yl)cyclopropanecarboxamide;

N-(5-(6-cyano-5-((1-(dimethylamino)-4,4-difluoro-1-oxobutan-2-yl)amino)pyridin-3-yl)pyrazin-2-yl)cyclopropanecarboxamide;

N-(5-(6-cyano-5-(1-((1-cyanoethyl)(methyl)amino)-1-oxopropan-2-yl)amino)pyridin-3-yl)pyrazin-2-yl)cyclopropanecarboxamide;

N-(5-(6-cyano-5-((1-((cyclopropylmethyl)(methyl)amino)-1-oxopropan-2-yl)amino)pyridin-3-yl)pyrazin-2-yl)cyclopropanecarboxamide;

N-(5-(6-cyano-5-((1-(methyl(pyridin-3-yl)amino)-1-oxopropan-2-yl)amino)pyridin-3-yl)pyrazin-2-yl)cyclopropanecarboxamide;

N-(5-(6-cyano-5-((1-((2,2-difluoroethyl)(2-hydroxyethyl)amino)-1-oxopropan-2-yl)amino)pyridin-3-yl)pyrazin-2-yl)cyclopropanecarboxamide;

N-(5-(6-cyano-5-(((S)-1-((S)-3-cyanomorpholino)-1-oxopropan-2-yl)amino)pyridin-3-yl)pyrazin-2-yl)cyclopropanecarboxamide;

N-(5-(6-cyano-5-((4,4-difluoro-1-((2-fluoroethyl)(methyl)amino)-1-oxobutan-2-yl)amino)pyridin-3-yl)pyrazin-2-yl)cyclopropanecarboxamide;

N-(5-(6-cyano-5-(((S)-1-((2,2-difluoroethyl)(methyl)amino)-1-oxopropan-2-yl)amino)pyridin-3-yl)pyrazin-2-yl)-2-methylcyclopropanecarboxamide;

N-(5-(6-cyano-5-((1-((1-cyanoethyl)(methyl)amino)-1-oxopropan-2-yl)amino)pyridin-3-yl)pyrazin-2-yl)cyclopropanecarboxamide;

N-(5-(6-cyano-5-((1-(3-methylmorpholino)-1-oxopropan-2-yl)amino)pyridin-3-yl)pyrazin-2-yl)cyclopropanecarboxamide;

N-(5-(6-cyano-5-((1-((cyanomethyl)(2-hydroxyethyl)amino)-1-oxopropan-2-yl)amino)pyridin-3-yl)pyrazin-2-yl)cyclopropanecarboxamide;

(R)-N-(5-(6-cyano-5-((2-oxo-2-(3-(trifluoromethyl)morpholino)ethyl)amino)pyridin-3-yl)pyrazin-2-yl)cyclopropanecarboxamide;

(S)-N-(5-(6-cyano-5-((2-oxo-2-(3-(trifluoromethyl)morpholino)ethyl)amino)pyridin-3-yl)pyrazin-2-yl)cyclopropanecarboxamide;

N-(5-(6-cyano-5-((1-(dimethylamino)-1-oxopropan-2-yl)amino)pyridin-3-yl)pyrazin-2-yl)-2-methylcyclopropanecarboxamide;

N-(5-(6-cyano-5-(((S)-1-(dimethylamino)-1-oxopropan-2-yl)amino)pyridin-3-yl)pyrazin-2-yl)-2-methylcyclopropanecarboxamide;

N-(5-(6-cyano-5-((1-(ethyl(methyl)amino)-1-oxopropan-2-yl)amino)pyridin-3-yl)pyrazin-2-yl)cyclopropanecarboxamide;

N-(5-(6-cyano-5-((1-((2,2-difluoroethyl)amino)-1-oxopropan-2-yl)amino)pyridin-3-yl)pyrazin-2-yl)cyclopropanecarboxamide;

N-(5-(6-cyano-5-((1-(dimethylamino)-4-hydroxy-1-oxobutan-2-yl)amino)pyridin-3-yl)pyrazin-2-yl)cyclopropanecarboxamide;

N-(5-(6-cyano-5-((1-oxo-1-((2,2,2-trifluoroethyl)amino)propan-2-yl)amino)pyridin-3-yl)pyrazin-2-yl)cyclopropanecarboxamide;

N-(5-(6-cyano-5-((1-((2,2-difluoropropyl)amino)-1-oxopropan-2-yl)amino)pyridin-3-yl)pyrazin-2-yl)cyclopropanecarboxamide;

N-(5-(6-cyano-5-((1-((2,2-difluorocyclopropyl)amino)-1-oxopropan-2-yl)amino)pyridin-3-yl)pyrazin-2-yl)cyclopropanecarboxamide;

N-(5-(6-cyano-5-((1-((1,1-difluoropropan-2-yl)amino)-1-oxopropan-2-yl)amino)pyridin-3-yl)pyrazin-2-yl)cyclopropanecarboxamide;

N-(5-(6-cyano-5-((1-((2,2-difluoroethyl)amino)-1-oxobutan-2-yl)amino)pyridin-3-yl)pyrazin-2-yl)cyclopropanecarboxamide;

N-(5-(5-cyano-4-((1-(dimethylamino)-1-oxobutan-2-yl)amino)pyridin-2-yl)pyrazin-2-yl)cyclopropanecarboxamide;

N-(5-(6-cyano-5-((1-(dimethylamino)-3-hydroxy-1-oxopropan-2-yl)amino)pyridin-3-yl)pyrazin-2-yl)cyclopropanecarboxamide;

N-(5-(6-cyano-5-((1-(dimethylamino)-1-oxopropan-2-yl)amino)pyridin-3-yl)pyrazin-2-yl)cyclopropanecarboxamide;

N-(5-(6-cyano-5-((1-(dimethylamino)-4-methoxy-1-oxobutan-2-yl)amino)pyridin-3-yl)pyrazin-2-yl)cyclopropanecarboxamide;

N-(5-(4-cyano-3-((1-(dimethylamino)-1-oxopropan-2-yl)amino)-5-fluorophenyl)pyrazin-2-yl)cyclopropanecarboxamide;

N-(5-(6-cyano-5-((1-(dimethylamino)-4,4,4-trifluoro-1-oxobutan-2-yl)amino)pyridin-3-yl)pyrazin-2-yl)cyclopropanecarboxamide;

N-(5-(6-cyano-5-((1-(3-fluoropyrrolidin-1-yl)-1-oxopropan-2-yl)amino)pyridin-3-yl)pyrazin-2-yl)cyclopropanecarboxamide;

N-(5-(6-cyano-5-(((S)-1-((2,2-difluoroethyl)(methyl)amino)-1-oxopropan-2-yl)amino)pyridin-3-yl)pyrazin-2-yl)-2-(hydroxymethyl)cyclopropanecarboxamide;

N-(5-(6-cyano-5-((1-(dimethylamino)-1-oxobutan-2-yl)amino)pyridin-3-yl)pyrazin-2-yl)-3-hydroxy-3-methylcyclobutanecarboxamide;

N-(5-(6-cyano-5-((1-((2,2-difluoroethyl)(methyl)amino)-1-oxopropan-2-yl)amino)pyridin-3-yl)pyrazin-2-yl)-3-hydroxy-3-methylcyclobutanecarboxamide;

N-(5-(6-cyano-5-((1-((2,2-difluoroethyl)(methyl)amino)-1-oxopropan-2-yl)amino)pyridin-3-yl)pyrazin-2-yl)-3-methoxycyclobutanecarboxamide;

N-(5-(6-cyano-5-((1-((2,2-difluoroethyl)(methyl)amino)-1-oxopropan-2-yl)amino)pyridin-3-yl)pyrazin-2-yl)cyclobutanecarboxamide; and a pharmaceutically acceptable salt of any one of the above-mentioned compounds.

16. The compound according to claim 1, which is selected from the following compounds:

(S)-N-(5-(4-cyano-3-((1-(dimethylamino)-1-oxopropan-2-yl)amino)phenyl)pyrazin-2-yl)cyclopropanecarboxamide;

(S)-N-(5-(4-cyano-3-((1-(dimethylamino)-3-methyl-1-oxobutan-2-yl)amino)phenyl)pyrazin-2-yl)cyclopropanecarboxamide;

(S)-N-(5-(4-cyano-3-((1-(dimethylamino)-4-methoxy-1-oxobutan-2-yl)amino)phenyl)pyrazin-2-yl)cyclopropanecarboxamide;

(S)-N-(5-(4-cyano-3-((1-(dimethylamino)-4,4-difluoro-1-oxobutan-2-yl)amino)phenyl)pyrazin-2-yl)cyclopropanecarboxamide;

(S)-N-(5-(3-((1-(azetidin-1-yl)-1-oxopropan-2-yl)amino)-4-cyanophenyl)pyrazin-2-yl)cyclopropanecarboxamide;

(S)-N-(5-(4-cyano-3-((1-oxo-1-(pyrrolidin-1-yl)propan-2-yl)amino)phenyl)pyrazin-2-yl)cyclopropanecarboxamide;

(S)-N-(5-(4-cyano-3-((1-(3-hydroxyazetidin-1-yl)-1-oxopropan-2-yl)amino)phenyl)pyrazin-2-yl)cyclopropanecarboxamide;

(S)-N-(5-(4-cyano-3-((1-(ethyl(methyl)amino)-1-oxopropan-2-yl)amino)phenyl)pyrazin-2-yl)cyclopropanecarboxamide;

(S)-N-(5-(4-cyano-3-((1-((2-hydroxyethyl)amino)-1-oxopropan-2-yl)amino)phenyl)pyrazin-2-yl)cyclopropanecarboxamide ;

(S)-N-(5-(4-cyano-3-((1-(isopropylamino)-1-oxopropan-2-yl)amino)phenyl)pyrazin-2-yl)cyclopropanecarboxamide;

(S)-N-(5-(4-cyano-3-((1-((2-methoxyethyl)amino)-1-oxopropan-2-yl)amino)phenyl)pyrazin-2-yl)cyclopropanecarboxamide;

(S)-N-(5-(4-cyano-3-((1-(3-methoxyazetidin-1-yl)-1-oxopropan-2-yl)amino)phenyl)pyrazin-2-yl)cyclopropanecarboxamide;

(S)-N-(5-(4-cyano-3-((1-((2-methoxyethyl)(methyl)amino)-1-oxopropan-2-yl)amino)phenyl)pyrazin-2-yl)cyclopropanecarboxamide;

(S)-N-(5-(4-cyano-3-((1-(dimethylamino)-3-hydroxy-1-oxopropan-2-yl)amino)phenyl)pyrazin-2-yl)cyclopropanecarboxamide;

(S)-N-(5-(4-cyano-3-((1-((2-hydroxyethyl)(methyl)amino)-1-oxopropan-2-yl)amino)phenyl)pyrazin-2-yl)cyclopropanecarboxamide;

(S)-N-(5-(4-cyano-3-((1-(dimethylamino)-1-oxobutan-2-yl)amino)phenyl)pyrazin-2-yl)cyclopropanecarboxamide;

(S)-N-(5-(4-cyano-3-((1-(dimethylamino)-4-hydroxy-1-oxobutan-2-yl)amino)phenyl)pyrazin-2-yl)cyclopropanecarboxamide;

(S)-N-(5-(4-cyano-3-((1-((2-hydroxyethyl)(methyl)amino)-1-oxobutan-2-yl)amino)phenyl)pyrazin-2-yl)cyclopropanecarboxamide;

(S)-N-(5-(6-cyano-5-((1-(dimethylamino)-1-oxopropan-2-yl)amino)pyridin-3-yl)pyrazin-2-yl)cyclopropanecarboxamide;

(S)-N-(5-(6-cyano-5-((1-(dimethylamino)-1-oxobutan-2-yl)amino)pyridin-3-yl)pyrazin-2-yl)cyclopropanecarboxamide;

N-(5-(6-cyano-5-(((2S,3R)-1-(dimethylamino)-3-hydroxy-1-oxobutan-2-yl)amino)pyridin-3-yl)pyrazin-2-yl)cyclopropanecarboxamide;

(S)-N-(5-(6-cyano-5-((1-((2-hydroxyethyl)(methyl)amino)-1-oxopropan-2-yl)amino)pyridin-3-yl)pyrazin-2-yl)cyclopropanecarboxamide;

(S)-N-(5-(6-cyano-5-((1-(cyclopropyl(methyl)amino)-1-oxobutan-2-yl)amino)pyridin-3-yl)pyrazin-2-yl)cyclopropanecarboxamide;

N-(5-(6-cyano-5-(((2R,3R)-1-(dimethylamino)-3-hydroxy-1-oxobutan-2-yl)amino)pyridin-3-yl)pyrazin-2-yl)cyclopropanecarboxamide;

N-(5-(6-cyano-5-(((2R,3S)-1-(dimethylamino)-3-hydroxy-1-oxobutan-2-yl)amino)pyridin-3-yl)pyrazin-2-yl)cyclopropanecarboxamide;

N-(5-(6-cyano-5-(((2S,3S)-1-(dimethylamino)-3-hydroxy-1-oxobutan-2-yl)amino)pyridin-3-yl)pyrazin-2-yl)cyclopropanecarboxamide;

(S)-N-(5-(6-cyano-5-((1-(methyl(2,2,2-trifluoroethyl)amino)-1-oxopropan-2-yl)amino)pyridin-3-yl)pyrazin-2-yl)cyclopropanecarboxamide;

(S)-N-(5-(6-cyano-5-((1-(dimethylamino)-3-methoxy-1-oxopropan-2-yl)amino)pyridin-3-yl)pyrazin-2-yl)cyclopropanecarboxamide;

(S)-N-(5-(6-cyano-5-((1-((cyanomethyl)(methyl)amino)-1-oxopropan-2-yl)amino)pyridin-3-yl)pyrazin-2-yl)cyclopropanecarboxamide;

(S)-N-(5-(6-cyano-5-((3-cyano-1-(dimethylamino)-1-oxopropan-2-yl)amino)pyridin-3-yl)pyrazin-2-yl)cyclopropanecarboxamide;

(S)-N-(5-(6-cyano-5-((1-((2,2-difluoroethyl)(methyl)amino)-1-oxopropan-2-yl)amino)pyridin-3-yl)pyrazin-2-yl)cyclopropanecarboxamide;

(S)-N-(5-(6-cyano-5-((1-((2-fluoroethyl)(methyl)amino)-1-oxopropan-2-yl)amino)pyridin-3-yl)pyrazin-2-yl)cyclopropanecarboxamide;

(S)-N-(5-(6-cyano-5-((1-((cyanomethyl)(methyl)amino)-1-oxobutan-2-yl)amino)pyridin-3-yl)pyrazin-2-yl)cyclopropanecarboxamide;

(S)-N-(5-(6-cyano-5-((1-((2-hydroxyethyl)(methyl)
amino)-4-methoxy-1-oxobutan-2-yl)amino)pyridin-3-
yl)pyrazin-2-yl)cyclopropanecarboxamide;
(S)-N-(5-(6-cyano-5-(((S)-1-((R)-2-cyanopyrrolidin-1-
yl)-1-oxopropan-2-yl)amino)pyridin-3-yl)pyrazin-2-
yl)cyclopropanecarboxamide;
(S)-N-(5-(6-cyano-5-((1-((2-fluoroethyl)(methyl)amino)-
1-oxobutan-2-yl)amino)pyridin-3-yl)pyrazin-2-yl)cy-
clopropanecarboxamide;
(S)-N-(5-(6-cyano-5-((1-(dimethylamino)-3-hydroxy-1-
oxopropan-2-yl)amino)pyridin-3-yl)pyrazin-2-yl)cy-
clopropanecarboxamide;
(S)-N-(5-(6-cyano-5-((1-((2,2-difluoroethyl)(methyl)
amino)-3-hydroxy-1-oxopropan-2-yl)amino)pyridin-3-
yl)pyrazin-2-yl)cyclopropanecarboxamide;
N-(5-(6-cyano-5-((S)-1-oxo-1-((R)-2-(trifluoromethyl)
oxazolidin-3-yl)propan-2-ylamino)pyridin-3-yl)
pyrazin-2-yl)cyclopropanecarboxamide;
N-(5-(6-cyano-5-((S)-1-oxo-1-((S)-2-(trifluoromethyl)
oxazolidin-3-yl)propan-2-ylamino)pyridin-3-yl)
pyrazin-2-yl)cyclopropanecarboxamide;
N-(5-(6-cyano-5-(((2S)-1-((1-cyanoethyl)amino)-1-oxo-
propan-2-yl)amino)pyridin-3-yl)pyrazin-2-yl)cyclo-
propanecarboxamide;
(S)-N-(5-(6-cyano-5-((1-((2-(dimethylamino)ethyl)
(methyl)amino)-1-oxopropan-2-yl)amino)pyridin-3-yl)
pyrazin-2-yl)cyclopropanecarboxamide;
(S)-N-(5-(6-cyano-5-((1-(dimethylamino)-4,4-difluoro-
1-oxobutan-2-yl)amino)pyridin-3-yl)pyrazin-2-yl)cy-
clopropanecarboxamide;
N-(5-(6-cyano-5-(((2S)-1-((1-cyanoethyl)(methyl)
amino)-1-oxopropan-2-yl)amino)pyridin-3-yl)pyrazin-
2-yl)cyclopropanecarboxamide;
(S)-N-(5-(6-cyano-5-((1-((cyclopropylmethyl)(methyl)
amino)-1-oxopropan-2-yl)amino)pyridin-3-yl)pyrazin-
2-yl)cyclopropanecarboxamide;
(S)-N-(5-(6-cyano-5-((1-(methyl(pyridin-3-yl)amino)-1-
oxopropan-2-yl)amino)pyridin-3-yl)pyrazin-2-yl)cy-
clopropanecarboxamide;
(S)-N-(5-(6-cyano-5-((1-((2,2-difluoroethyl)(2-hydroxy-
ethyl)amino)-1-oxopropan-2-yl)amino)pyridin-3-yl)
pyrazin-2-yl)cyclopropanecarboxamide;
(S)-N-(5-(6-cyano-5-(((S)-1-((S)-3-cyanomorpholino)-1-
oxopropan-2-yl)amino)pyridin-3-yl)pyrazin-2-yl)cy-
clopropanecarboxamide;
(S)-N-(5-(6-cyano-5-((4,4-difluoro-1-((2-fluoroethyl)
(methyl)amino)-1-oxobutan-2-yl)amino)pyridin-3-yl)
pyrazin-2-yl)cyclopropanecarboxamide;
(S)-N-(5-(6-cyano-5-(((S)-1-((2,2-difluoroethyl)(methyl)
amino)-1-oxopropan-2-yl)amino)pyridin-3-yl)pyrazin-
2-yl)-2-methylcyclopropanecarboxamide;
N-(5-(6-cyano-5-(((S)-1-(((R)-1-cyanoethyl)(methyl)
amino)-1-oxopropan-2-yl)amino)pyridin-3-yl)pyrazin-
2-yl)cyclopropanecarboxamide;
N-(5-(6-cyano-5-(((S)-1-(((S)-1-cyanoethyl)(methyl)
amino)-1-oxopropan-2-yl)amino)pyridin-3-yl)pyrazin-
2-yl)cyclopropanecarboxamide;
N-(5-(6-cyano-5-(((S)-1-((S)-3-methylmorpholino)-1-
oxopropan-2-yl)amino)pyridin-3-yl)pyrazin-2-yl)cy-
clopropanecarboxamide;
(S)-N-(5-(6-cyano-5-((1-((cyanomethyl)(2-hydroxyethyl)
amino)-1-oxopropan-2-yl)amino)pyridin-3-yl)pyrazin-
2-yl)cyclopropanecarboxamide;
(S)-N-(5-(5-((2-(4-acetylpiperazin-1-yl)-2-oxoethy-
pamino)-6-cyanopyridin-3-yl)pyrazin-2-yl)cyclopro-
panecarboxamide;
(S)-N-(5-(6-cyano-5-((2-(3-cyanopyrrolidin-1-yl)-2-oxo-
ethyl)amino)pyridin-3-yl)pyrazin-2-yl)cyclopropan-
ecarboxamide;
(1S,2S)-N-(5-(6-cyano-5-(((S)-1-(dimethylamino)-1-
oxopropan-2-yl)amino)pyridin-3-yl)pyrazin-2-yl)-2-
methylcyclopropanecarboxamide;
(1R,2R)-N-(5-(6-cyano-5-(((S)-1-(dimethylamino)-1-
oxopropan-2-yl)amino)pyridin-3-yl)pyrazin-2-yl)-2-
methylcyclopropanecarboxamide;
(1R,2S)-N-(5-(6-cyano-5-(((S)-1-(dimethylamino)-1-
oxopropan-2-yl)amino)pyridin-3-yl)pyrazin-2-yl)-2-
methylcyclopropanecarboxamide;
(1S,2R)-N-(5-(6-cyano-5-(((S)-1-(dimethylamino)-1-
oxopropan-2-yl)amino)pyridin-3-yl)pyrazin-2-yl)-2-
methylcyclopropanecarboxamide;
(S)-N-(5-(6-cyano-5-((1-(ethyl(methyl)amino)-1-oxopro-
pan-2-yl)amino)pyridin-3-yl)pyrazin-2-yl)cyclopro-
panecarboxamide;
N-(5-(6-cyano-5-((2-((2S,4R)-4-(hydroxymethyl)-2-(trif-
luoromethyl)pyrrolidin-1-yl)-2-oxoethyl)amino)pyri-
din-3-yl)pyrazin-2-yl)cyclopropanecarboxamide;
(S)-N-(5-(6-cyano-5-((1-((2,2-difluoroethyl)amino)-1-
oxopropan-2-yl)amino)pyridin-3-yl)pyrazin-2-yl)cy-
clopropanecarboxamide;
(S)-N-(5-(6-cyano-5-((1-(dimethylamino)-4-hydroxy-1-
oxobutan-2-yl)amino)pyridin-3-yl)pyrazin-2-yl)cyclo-
propanecarboxamide;
(S)-N-(5-(6-cyano-5-((1-oxo-1-((2,2,2-trifluoroethyl)
amino)propan-2-yl)amino)pyridin-3-yl)pyrazin-2-yl)
cyclopropanecarboxamide;
(S)-N-(5-(6-cyano-5-((1-((2,2-difluoropropyl)amino)-1-
oxopropan-2-yl)amino)pyridin-3-yl)pyrazin-2-yl)cy-
clopropanecarboxamide;
N-(5-(6-cyano-5-(((2S)-1-((2,2-difluorocyclopropyl)
amino)-1-oxopropan-2-yl)amino)pyridin-3-yl)pyrazin-
2-yl)cyclopropanecarboxamide;
N-(5-(6-cyano-5-(((2S)-1-((1,1-difluoropropan-2-yl)
amino)-1-oxopropan-2-yl)amino)pyridin-3-yl)pyrazin-
2-yl)cyclopropanecarboxamide;
(S)-N-(5-(6-cyano-5-((1-((2,2-difluoroethyl)amino)-1-
oxobutan-2-yl)amino)pyridin-3-yl)pyrazin-2-yl)cyclo-
propanecarboxamide;
(S)-N-(5-(5-cyano-4-((1-(dimethylamino)-1-oxobutan-2-
yl)amino)pyridin-2-yl)pyrazin-2-yl)cyclopropanecar-
boxamide;
(S)-N-(5-(6-cyano-5-((1-(dimethylamino)-4-methoxy-1-
oxobutan-2-yl)amino)pyridin-3-yl)pyrazin-2-yl)cyclo-
propanecarboxamide
(S)-N-(5-(4-cyano-3-((1-(dimethylamino)-1-oxopropan-
2-yl)amino)-5-fluorophenyl)pyrazin-2-yl)cyclopropan-
ecarboxamide;
(S)-N-(5-(6-cyano-5-((1-(dimethylamino)-4,4,4-trif-
luoro-1-oxobutan-2-yl)amino)pyridin-3-yl)pyrazin-2-
yl)cyclopropanecarboxamide;
N-(5-(6-cyano-5-(((S)-1-((S)-3-fluoropyrrolidin-1-yl)-1-
oxopropan-2-yl)amino)pyridin-3-yl)pyrazin-2-yl)cy-
clopropanecarboxamide;
N-(5-(6-cyano-5-(((S)-1-((2,2-difluoroethyl)(methyl)
amino)-1-oxopropan-2-yl)amino)pyridin-3-yl)
pyrazin-2-yl)-2-(hydroxymethyl)cyclopropanecarbox-
amide;
(S)-N-(5-(6-cyano-5-((1-(dimethylamino)-1-oxobutan-2-
yl)amino)pyridin-3-yl)pyrazin-2-yl)-3-hydroxy-3-
methylcyclobutanecarboxamide;

(S)-N-(5-(6-cyano-5-((1-((2,2-difluoroethyl)(methyl) amino)-1-oxopropan-2-yl)amino)pyridin-3-yl) pyrazin-2-yl)-3-hydroxy-3-methylcyclobutanecarboxamide;

(S)-N-(5-(6-cyano-5-((1-((2,2-difluoroethyl)(methyl) amino)-1-oxopropan-2-yl)amino)pyridin-3-yl)pyrazin-2-yl)-3-methoxycyclobutanecarboxamide;

(S)-N-(5-(6-cyano-5-((1-((2,2-difluoroethyl)(methyl) amino)-1-oxopropan-2-yl)amino)pyridin-3-yl)pyrazin-2-yl)cyclobutanecarboxamide; and a pharmaceutically acceptable salt of any one of the above-mentioned compounds.

17. A pharmaceutical composition comprising a compound or pharmaceutically acceptable salt as defined in claim 1, and a pharmaceutically acceptable excipient.

18. A method of treating a condition associated with TBK1 in a subject having said condition, the method comprising administering to the subject a compound or pharmaceutically acceptable salt as defined in claim 1, wherein the condition is selected from autoimmune disorder, inflammatory disorders, fibrotic conditions, cancer, and sepsis.

* * * * *